(12) United States Patent
Barf et al.

(10) Patent No.: US 8,772,286 B2
(45) Date of Patent: Jul. 8, 2014

(54) MK2 INHIBITORS

(75) Inventors: Tjeerd Andries Barf, Ravenstein (NL); Arthur Oubrie, Wychen (NL); Carsten Schultz-Fademrecht, Pomezia (IT); Eduard Willem Zwart, Oss (NL); Niels Hoogenboom, Ryen (NL); Sander Martijn De Wilde, Oss (NL); Allard Kaptein, Zaltbommel (NL)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 13/514,865

(22) PCT Filed: Dec. 13, 2010

(86) PCT No.: PCT/EP2010/069465
§ 371 (c)(1),
(2), (4) Date: Jun. 8, 2012

(87) PCT Pub. No.: WO2011/073119
PCT Pub. Date: Jun. 23, 2011

(65) Prior Publication Data
US 2012/0245175 A1    Sep. 27, 2012

Related U.S. Application Data

(60) Provisional application No. 61/286,091, filed on Dec. 14, 2009.

(30) Foreign Application Priority Data

Dec. 14, 2009  (EP) .................................... 09179043

(51) Int. Cl.
*A61K 31/535* (2006.01)

(52) U.S. Cl.
USPC ........ 514/234.5; 514/256; 514/275; 514/278; 544/71; 544/230; 546/18

(58) Field of Classification Search
USPC ......... 514/234.5, 256, 275, 278; 544/230, 71; 546/18
See application file for complete search history.

(56) References Cited

U.S. PATENT DOCUMENTS 7,528,143 B2 *  5/2009  Noronha et al. .............. 514/275
2004/0209897 A1 * 10/2004  Vernier et al. .............. 514/259.2

FOREIGN PATENT DOCUMENTS

| WO | 2004058762 A1 | 7/2004 |
| WO | 2005013986 A1 | 2/2005 |
| WO | 2005014572 A1 | 2/2005 |
| WO | 2009010488 A1 | 1/2009 |

OTHER PUBLICATIONS

A.M. Traynor et al., Drugs of Today, 40(8), 697-710 (2004).*

S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
M. Kobel et al., PLoS Medicine, 5(12) 1749-1760 (2008).*
A.J. Tiltman, Best Practice & Research Clinical Obstetrics & Gynaecology, 485-500, 19(4) (2005).*
J. L. Raizer, Journal of Neuro-Oncology, 74(1), 77-86 (2005).*
R.G.W. Verhaak et al., Cancer Cell, 17(1), 1-24 (2010).*
S.K. Libutti, Colon Cancer in, 1 Cancer Principles & Practice of Oncology 1232, 1243 (V.T. DeVita, Jr. et al. eds., 8th ed., 2008).*
L. Pusztai, Histopathologic and Molecular Markers of Prognosis and Response to Therapy, in Breast Cancer 324, 326-328 (Kelly k. Hunt et al., ed., 2nd ed., 2008).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
F.F. De Arruda, et al., Int. J. Radiation Oncology Biol. Phys., 64(2), 363-373 (2006).*
B.C. Bastian, Genetic Progression, in From Melanocytes to Melanoma the Progression to Malignancy 197, 201 (V. J. Hearing et al., eds., 2006).*

(Continued)

*Primary Examiner* — Deepak Rao
*Assistant Examiner* — Alexander R Pagano
(74) *Attorney, Agent, or Firm* — Maria V. Marucci; Valerie J. Camara

(57) ABSTRACT

The present invention relates to compounds of general Formula (I) or a pharmaceutically acceptable salt thereof. The compounds can be used in the treatment of immune, autoimmune, inflammatory diseases, cardiovascular diseases, infectious diseases, bone resorption disorders, neurodegenerative diseases or proliferative diseases.

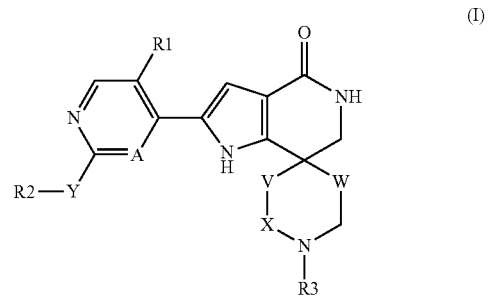

16 Claims, No Drawings

(56) References Cited

OTHER PUBLICATIONS

J. Tsai et al., 105 PNAS 3041-3046, 3041 (2008).*
T. Carling et al., Thyroid Tumors in, 2 Cancer Principles & Practice of Oncology 1503 (V.T. DeVita, Jr. et al. eds., 8th ed., 2008).*
B Testa et al., Prodrug Design in, 5 Encyclopedia of Pharmaceutical Technology, 3008-3014 (J. Swarbrick ed., 3rd ed., 2007).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
K. Odunsi et al, Molecular Biology of Gynecological Cancers, in 2 Cancer Principles & Practice of Oncology 1487, 1492 (V.T. DeVita, Jr. et al. eds., 8th ed., 2008).*
K.P. Olive et al., Clinical Cancer Research 12, 5277-5287 (2006).*
A-M Bleau et al., 8 Cell Cycle 2937-2945 (2009).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
Turko et al., Pharmacological Reviews, 619-634 (2002).*
F.A. Scappaticci et al., 99 Journal of the National Cancer Institute, 1232-1239 (2007).*
Ha et al., 104 The American Journal of Gastroenterology, 1445-1451 (2009).*
D. D'Ambrosio et al., 273 Journal of Immunological Methods 3-13 (2003).*
J.H. Poupaert, Drug Design: Basic Principles and Applications, in 2 Encyclopedia of Pharmaceutical Technology 1362-1369 (James Swarbrick ed., 3rd ed., 2007).*
L.I. Zon et al., Nature Reviews Drug Discovery 4 (2005).*
G. M Cleator et al., Herpes Simplex in, Principles and Practice of Clinical Virology 27-51(Arie J. Zuckerman et al., eds., 5th ed., 2004).*
Duraisamy et al., 12 Expert Opinion Therapeutic Targets 921-936 (2008).*
Z. Xiong et al., 18 Bioorganic & Medicinal Chemistry Letters 1994-1999 (2008).*
M Hegan et al., 177 The Journal of Immunology, 1913-1917 (2006).*
S. Duraisamy et al. 12 Expert Opinion in therapeutic Targets, 921-936 (2008).*
Duraisamy, et al., "MK2: a novel molecular target for anti-inflammatory therapy," Expert Opin. Ther. Targets, vol. 12, 2008, pp. 921-936.
Felix, et al., "SAGE analysis highlights the importance of p53csv, ddx5, mapkapk2 and ranbp2 to multiple myeloma tumorigenesis," Cancer Letters, vol. 278, 2009, pp. 41-48.
Gaestel, "MAPKAP kinases—MKs—two's company, three's a crowd," Nat. Rev. Mol. Cell Biol., vol. 7, Feb. 2006, pp. 120-130.
Hideshima, et al., "p38 MAPK inhibition enhances PS-341 (bortezomib)-induced cytotoxicity against multiple myeloma cells," Oncogene, 2004, vol. 23, pp. 8766-8776.
Johansen, et al., "MK2 regulates the early stages of skin tumor promotion," Carcinogenesis, 2009, vol. 30, pp. 2100-2108.
Kumar, et al., "p38 Mitogen-Activated Protein Kinase-Driven MAPKAPK2 Regulates Invasion of Bladder Cancer by Modulation of MMP-2 and MMP-9 Activity," Cancer Res., 2010, vol. 70, pp. 832-841.
Manke, et al., "MAPKAP Kinase-2 Is a Cell Cycle Checkpoint Kinase that Regulates the G2/M Transition and S Phase Progression in Response to UV Irradiation," Molecular Cell, 2005, vol. 17, pp. 37-48.
Reinhardt, et al., "p53-Deficient Cells Rely on ATM- and ATR-Mediated Checkpoint Signaling through the p38MAPK/MK2 Pathway for Survival after DNA Damage," Cancer Cell, 2007, vol. 11, pp. 175-189.
Xu, et al., "MAPKAPK2 and HSP27 are downstream effectors of p38 MAP kinase-mediated matrix metalloproteinase type 2 activation and cell invasion in human prostate cancer," Oncogene, 2006, vol. 25, pp. 2987-2998.

* cited by examiner

MK2 INHIBITORS

CROSS REFERENCE TO RELATED APPLICATIONS

This application is a U.S. National Phase application under 35 U.S.C. §371 of PCT Application No. PCT/EP2010/069465, filed Dec. 13, 2010, which claims priority under 35 U.S.C. §119(e) from U.S. Provisional Application Ser. No. 61/286,091, filed Dec. 14, 2009.

The present invention relates to pyrrolo[3,2-c]pyridin]-4' (1'H)-one derivatives, to pharmaceutical compositions comprising the same and to the use of said compounds for the manufacture of medicaments for the treatment of immunological disorders and oncology.

Regulation of pro-inflammatory cytokine production and release plays an important role in the instigation and propagation of inflammatory processes. Excessive release of these inflammatory cytokines is a prominent feature of many autoimmune diseases. In rheumatoid arthritis (RA), the importance of modulation of the action of pro-inflammatory cytokines such as TNFα and IL-6 is shown by the effectiveness of the anti-TNFα therapy and the anti-IL-6R therapy. In addition, anti-TNFα treatment is also effective in inflammatory bowel disease (IBD) and Psoriasis.

Because of the reported efficacy for anti-TNFα and anti-IL-6R therapy, low-molecular weight drugs that interfere with the production of pro-inflammatory cytokines such as TNFα and IL-6 are being developed. Modulation of the p38/MK2 pathway is seen as an attractive approach to control the production of these pro-inflammatory cytokines.

There are numerous observations highlighting the potential for MK2 (mitogen activated protein kinase activated protein kinase-2, MAPKAPK2) as a drug target. The MK2 knockout mice are almost completely resistant to LPS-induced endotoxic shock [Kotlyarov et al, Nat. Cell Biol. (1999) 1, 94-97]. Furthermore, spleen cells of MK2 knockout versus wild-type mice secrete only 10-20% of TNFα and IL-6 after an LPS challenge [Kotlyarov et al, Nat. Cell Biol. (1999) 1, 94-97]. In addition, MK2 knockout mice in the CIA model show a strong reduction (75%) in disease incidence and disease severity score. A clear reduction in the disease severity score was also observed for the MK2 heterozygote mice (50%) [Hegen et al, J. Immunol. (2006) 177, 1913-1917]. The latter finding suggests that complete depletion of MK2 activity may not be essential to see a regulatory effect for MK2.

That indeed the kinase activity of MK2 is required for the effects observed is supported by the finding that LPS-induced TNFα production in bone marrow derived macrophages (BMDMs) from MK2 knockout mice can be restored by the expression of full length MK2 or the catalytic domain of MK2 but not by a kinase inactive mutant of MK2 [Kotlyarov et al, Moll. Cell. Biol. (2002) 22, 4825-4835]. MK2 is suggested to regulate TNFα expression in lesional psoriatic skin at a posttranslational level [Johansen et al, J. Immunol. (2006) 176, 1431-1438], and reduced oxazolone-induced skin inflammation was observed in MK2 knockout mice [Funding et al, J. Invest. Dermatol. (2009) 129, 891-898].

Systemic deficiency of MK2 reduced atherosclerosis in hypercholesterolemic mice, and decreased aortic expression of key macrophage recruitment mediators VCAM-1 and MCP-1 [Jagavelu et al, Circ. Res. (2007) 101, 1104-1112]. MK2 is also shown to modulate key biological pathways associated with osteoarthritis (OA) disease pathology [Jones et al, Osteoarthritis & Cartilage (2009), 17, 124-131]. MK2 is active in OA human articular cartilage and in isolated primary human chondrocytes, and MK2 mediates the release of PGE2, MMP3 and MMP13.

Furthermore, MK2 mediates posttranscriptional regulation by p38 of TNFα-induced ICAM-1 and IL-8 in human lung microvascular endothial cells [Su et al, Biochim. Biophycica Acta (2008) 1783, 1623-1631], suggestive of a role in pulmonary inflammatory responses, and acute lung injury. Elimination of MK2 prevents neuronal cell death by reducing neuroinflammation. In the 1-methyl-4-phenyl-1,2,3,6-tetrahydropyridine (MPTP) mouse model for Parkinson's disease, MK2-deficient mice show reduced degeneration of dopaminergic neurons in the substantia nigra [Thomas et al, J Neurochem. (2008) 105, 2039-2052]

It is also shown that pancreatitis in mice with deletion of the MK2 gene is less severe as compared to wild-type mice, and is accompanied by reduced serum levels of TNFα and IL-6 [Tietz et al, Am. J. Physiol. Gastrointest. Liver Physiol. (2006) 290, G1298-1306]. Finally, MK2 deficiency protect the brain from neurological deficits and ischemic injury in mice [Wang et al, J. Biol. Chem. (2002) 277, 43968-43972].

Pyrrolopyridine compounds that inhibit MK2 have been disclosed in WO2005014572 and WO2004058762.

There clearly is a need for compounds that inhibit the mitogen activated protein kinase activated protein kinase-2 (MK2, MAPKAPK2).

To that aim, the present invention provides pyrrolo[3,2-c]pyridin]-4'(1'H)-one derivatives.

More specifically, the present invention provides pyrrolo[3,2-c]pyridin]-4'(1'H)-one compounds according to formula I

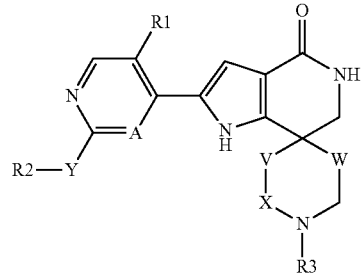

Formula I or a pharmaceutically acceptable salt thereof.

In this Formula R1 through R9, A, V, W X and Y have the following definitions:
A is CH or N;
X is a bond, —CH$_2$— or —CH$_2$CH$_2$—;
Y is a bond or —C(O)NH— with R2 attached to the carbonyl;
V is —CH$_2$—, O, C(O), —CHF—, or —CF$_2$—, with the proviso that if V is O, X is —CH$_2$CH$_2$— and that if V is C(O), X is —CH$_2$—;
W is a bond or —CH2-;
R1 is hydrogen or F;
R2 is a (1-12C)heteroaryl or (6-10C)aryl both optionally substituted with one or more groups independently selected from R4;
R3 is a hydrogen; (3-6C)cycloalkyl; (1-6C)alkyl, —(CH2)mOR5; —(CH2)mNR5R6; or —C(O)CH$_2$NR5R6;
R4 through R6 as defined in R2 and R3 have the following meanings:
R4 is taken from halogen; OH; SH; nitrile, nitro, NH2; (3-6C) cycloalkyl, (3-6C)cycloalkoxy, (1-6C)alkoxy or (1-6C) alkyl, all optionally substituted with one or more halogen;

phenoxy; —O(CH$_2$)$_m$OR5, —O(CH$_2$)$_m$NR7R8, —OC(O)R7 with the proviso that R7 is not hydrogen, —O(1-12C)heteroaryl), —S(1-6C)alkyl); —S(3-6C) cycloalkyl)—; NR7R8; —NR9(CH$_2$)$_m$OR7, —NR9(CH$_2$)$_m$NR7R8; (1-6C) alkylcarbonyl; (3-6C)cycloalkylcarbonyl; —C(O) NR7R8; —C(O)NR9(CH$_2$)$_m$NR7R8, —C(O)NR9(CH$_2$)$_m$OR7, —C(O)OR7, —SO$_2$(1-6C)alkyl), —SO$_2$(3-6C)cycloalkyl); —O(1-6C)alkyl)O— where the oxygens are attached to the (1-12C) heteroaryl or (6-10C)aryl ring on two neighboring carbons; phenyl or (1-12C) heteroaryl;

R5 is hydrogen (3-6C)cycloalkyl; or (1-6C)alkyl;

R6 is hydrogen; (3-6C)cycloalkyl; (1-6C)alkyl; or (1-6C)alkylcarbonyl.

Finally R7 through R9 in R4 have the following meanings.

R7 is hydrogen, (1-6C)alkyl or (3-6C)cycloalkyl;

R8 is hydrogen; (3-6C)cycloalkyl; (1-6C)alkyl; or (1-6C)alkylcarbonyl; or

R7 and R8 together with the nitrogen to which they are bonded in NR7R8 can form a 5-7-membered nitrogen containing (4-6C)heterocyclyl ring, which members consist of one nitrogen and 4-6 carbon atoms and in addition to the nitrogen atom optionally contains one heteroatom selected from N, O or S;

R9 is hydrogen; (1-6C)alkyl or (3-6)cycloalkyl; and m is 2 or 3.

The compounds of the present invention have a good solubility and a good inhibitory effect (EC$_{50}$).

Thus, in one embodiment the invention provides compounds according to Formula I which have an improved solubility and a better inhibitory effect (pEC$_{50}$).

The term (1-6C)alkyl as used in the definition means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-3C)alkyl being the most preferred.

The term (1-12C)heteroaryl means an aromatic group having 1-12 carbon atoms and 1-4 heteroatoms selected from N, O and S, like benzofuranyl, dibenzofuranyl, quinolinyl, isoquinolyl, quinazolinyl, quinoxalinyl, cinnolinyl, phthalazinyl, pyridinyl, benzothienyl, benzothiazolyl, benzoxazolyl, benzimidazolyl, benzotriazolyl, indazolyl, indolyl, thiazolyl, thiadiazolyl, pyrimidinyl, pyrazinyl, pyridazinyl, triazinyl, tetrazolyl, imidazolyl, thienyl, oxazolyl, isoxazolyl, oxadiazolyl, triazolyl, imidazolyl, pyrrolyl, pyrazolyl or furyl. Preferred number of heteroatoms is one or two. Preferred heteroaryl groups are benzofuranyl, quinolinyl, pyridinyl, benzothiophenyl, benzothiazolyl, thiazolyl, pyrimidinyl, thienyl, pyrimidinyl, and furyl. Most preferred are benzofuranyl, quinolinyl, pyridinyl, or pyrimidinyl. The (1-12C)heteroaryl group may be attached via a carbon atom or a nitrogen, if feasible.

The term (1-5C)heteroaryl means an aromatic group having 1-5 carbon atoms and 1-4 heteroatoms selected from N, O and S, like thiazolyl, thiadiazolyl, pyrimidinyl, pyrazinyl, pyridazinyl, triazinyl, tetrazolyl, imidazolyl, thienyl, oxazolyl, isoxazolyl, oxadiazolyl, triazolyl, imidazolyl, pyrrolyl, pyrazolyl or furyl. Preferred number of heteroatoms is one or two. Preferred heteroaryl groups are pyridinyl, thiazolyl, pyrimidinyl, thienyl, pyrimidinyl, and furyl. Most preferred are pyridinyl or pyrimidinyl. The (1-5C)heteroaryl group may be attached via a carbon atom or a nitrogen, if feasible.

The term (4-6C)heterocyclyl means a N-containing cycloalkyl group which contains 4-6 carbon atoms and optionally in addition one heteroatom selected from N, O or S such as pyrolidyl and morphonylyl. Preferred is a cycloalkyl group with one N heteroatom.

The term (6-10C)aryl means an aryl group having 6-10 carbon atoms such as phenyl and naphthyl. Preferred is phenyl.

The term (3-6C)cycloalkylcarbonyl means a cycloalkylcarbonyl group, the cycloalkyl group of which contains 3-6 carbon atoms with the same meaning as previously defined.

The term (3-6C)cycloalkyl means a cycloalkyl group having 3-6 carbon atoms, such as cyclopropyl, ethylcyclopropyl, cyclobutyl, methylcyclobutyl, cyclopentyl and cyclohexyl.

The term (1-6C)alkoxy means an alkoxy group having 1-6 carbon atoms, the alkyl moiety having the same meaning as previously defined. (1-3C)Alkoxy groups are preferred.

The term (1-6C)alkylcarbonyl means an alkylcarbonyl group, the alkyl group of which as the above identified meaning.

The term halogen means fluorine, chlorine, bromine or iodine.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group unless the attachment point is indicated by a dash.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In another embodiment the invention provides compounds according to Formula I as defined here above wherein V is —CH$_2$— or O, with the proviso that if V is O, X is —CH$_2$CH$_2$—; and R4 is taken from halogen; OH; NH$_2$; (3-6C)cycloalkyl or (1-6C)alkyl, both optionally substituted with one or more halogen; (3-6C)cycloalkoxy; (1-6C)alkoxy; phenoxy; —NR7R8; (1-6C)alkylcarbonyl; (3-6C)cycloalkylcarbonyl; —C(O)NR7R8; —O(1-6C) alkyl)O— where the oxygens are attached to the (1-12C)heteroaryl or (6-10C)aryl ring on two neighboring carbons; phenyl or (1-12C)heteroaryl.

In another aspect the invention relates to compounds according to Formula I wherein R7 and R8 together with the nitrogen to which they are bonded in NR7R8 can form a 5-7-membered (4-6C)heterocyclyl ring with no further heteroatom.

In another aspect the invention relates to compounds according to Formula I wherein R4 is taken from halogen; OH; SH; nitrile, nitro, NH2; (3-6C)cycloalkyl or (1-6C)alkyl, both optionally substituted with one or more halogen; (3-6C) cycloalkoxy; (1-6C)alkoxy; phenoxy; —O(CH$_2$)$_m$OR5, —O(CH$_2$)$_m$NR7R8, —OC(O)R7 with the proviso that R7 is not hydrogen, —O(1-12C)heteroaryl), —S(1-6C)alkyl); —S(3-6C)cycloalkyl)-; NR7R8; —NR9(CH$_2$)$_m$OR7, —NR9(CH$_2$)$_m$NR7R8; (1-6C)alkylcarbonyl; (3-6C) cycloalkylcarbonyl; —C(O)NR7R8; —C(O)NR9 (CH$_2$)$_m$NR7R8, —C(O)NR9(CH$_2$)$_m$OR7, —C(O)OR7, —SO$_2$(1-6C)alkyl), —SO$_2$(3-6C)cycloalkyl); —O(1-6C) alkyl)O— where the oxygens are attached to the (1-12C) heteroaryl or (6-10C)aryl ring on two neighboring carbons; phenyl or (1-12C)heteroaryl.

In another aspect the invention relates to compounds according to Formula I wherein R7 is hydrogen or (3-6C) cycloalkyl.

In yet another embodiment the invention provides compounds according to Formula I wherein V is —CH$_2$—.

In another aspect the invention relates to compounds of formula I wherein W is —CH$_2$—.

In another aspect the invention relates to compounds of formula I wherein X is —CH$_2$—.

In another aspect the invention relates to compounds of formula I wherein R2 is (1-5C) heteroaryl optionally substituted with one or more groups independently selected from R4 wherein R4 is selected from —NR7R8; NH$_2$ or (1-6C) alkoxy.

In another aspect the invention relates to compounds of formula I wherein R2 is phenyl optionally substituted with one or more groups independently selected from R4, wherein R4 is taken from halogen; OH; (3-6C)cycloalkyl or (1-6C) alkyl, both optionally substituted with one or more halogen; (1-6C)alkoxy; phenoxy; (1-6C) alkylcarbonyl; (3-6C)cycloalkylcarbonyl; —C(O)NR7R8; —O(1-6C)alkyl)O— where the oxygens are attached to the (hetero)aryl ring on two neighboring carbons or phenyl.

In yet another aspect the invention relates to compounds of formula I wherein R3 is hydrogen; —(CH$_2$)$_m$NR5R6, or —C(O)CH$_2$NR5R6.

In another aspect the invention relates to compounds of formula I wherein R3 is hydrogen.

In another aspect the invention relates to compounds of formula I wherein R3 is methyl, and Y=—C(O)NH—.

In yet another aspect the invention relates to compounds of formula I wherein Y is a bond.

The invention also relates to those compounds wherein all specific definitions for R1 through R9, and V, W, X and Y in the various aspects of the invention as defined here above occur in any combination within the definition of the pyrrolo [3,2-c]pyridin]-4'(1'H)-one compound of formula I.

In another aspect the invention relates to compounds according to Formula I wherein the spiro group attached to the pyrrolo[3,2-c]pyridin]-4'(1'H)-one skeleton form a 5, 6 or 7-membered ring. Preferably this ring is a 5 or 6-membered ring.

In another aspect the invention relates to compounds according to Formula I which have a solubility of at least 20 mg/L.

In yet another aspect the invention relates to compounds according to Formula I which have a pEC50 of at least 6.5.

In another aspect the invention relates to compounds according to Formula I which have a relationship between solubility and pEC50 wherein solubility (in mg/L)+ 20*pEC50 is at least 180.

In still another aspect the invention relates to compounds according to Formula I which have a solubility of at least 20 mg/L, a pEC50 of at least 6.5 and a relationship between solubility and pEC50 wherein solubility+20*pEC50 is at least 180.

With the term solubility we mean the following: Solubility of solids is defined as the concentration of the compound in a solution that is in equilibrium with solid phase at the specified temperature and one atmosphere pressure. (Handbook of Chemistry and Physics. 95$^{th}$ Edition, 2004-2005). Solubility is commonly expressed as a concentration, either by mass (g of solute per kg of solvent, g per dL (100 mL) of solvent), molarity, molality, mole fraction or other similar descriptions of concentration. The maximum equilibrium amount of solute that can dissolve per amount of solvent is the solubility of that solute in that solvent under the specified conditions.

The term pEC$_{50}$ means the absolute value of the log(EC$_{50}$) wherein EC$_{50}$ is the concentration of the test compound that elicits half-maximal (50%) effect compared to the compound's maximally attainable effect. The values can be determined e.g. as described in example 14. Values can be determined using a software program such as Graphpad Prism 4.03 (GraphPad, San Diego, Calif.).

The compounds of the present invention, represented by formula (I) can generally prepared via an art-known Hantzsch condensation reaction of (II) and piperidine-2,4-dione derivative (III) using ammonium acetate wherein Q=Br, Cl, or another appropriate leaving group. This step can be performed as a one-pot reaction (Hantzsch), or in two steps via C-alkylation on (III) using an appropriate base and solvent such as potassium carbonate and acetonitrile, subsequently followed by the condensation with ammonium acetate (Paal-Knorr).

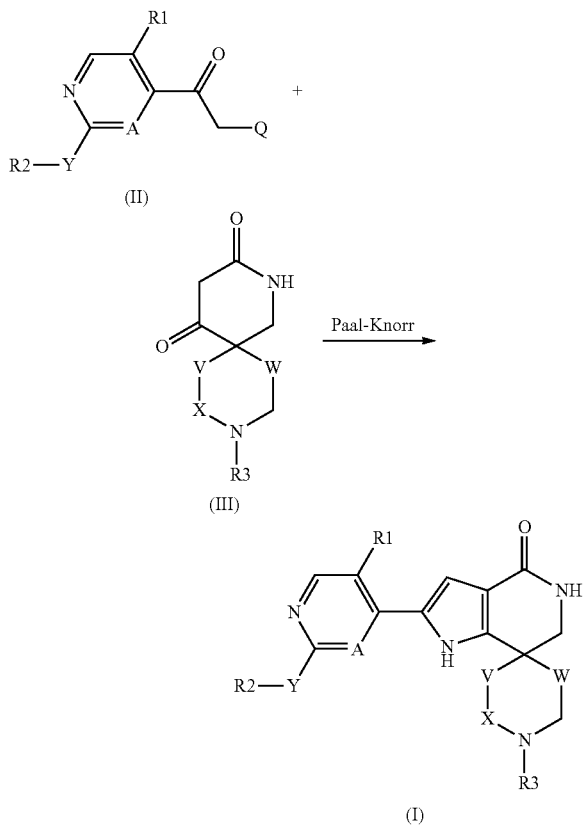

With certain decorations, R2 has to be introduced after the Hantzsch or Paal-Knorr condensation reaction with an art-known Suzuki, Stille (when Y is a bond) or Buchwald (when Y is —C(O)NH—) coupling utilizing Pd-catalyzed chemistry and a chlorine as the leaving group as in (IV).

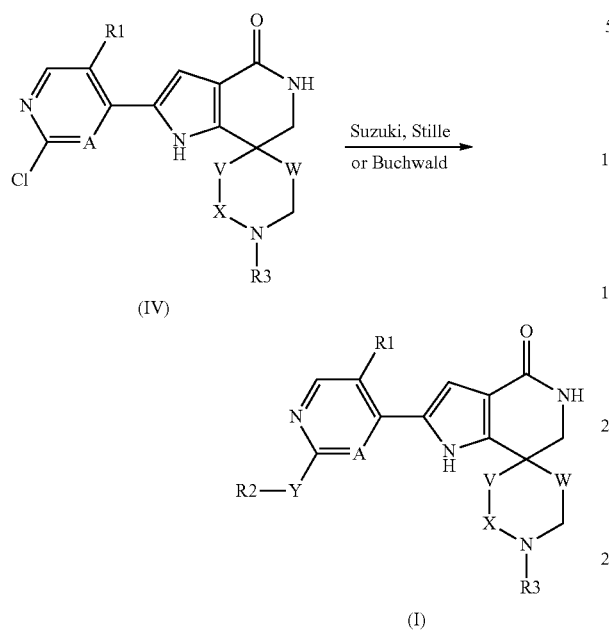

The preparation of intermediates (II) depends on the R1 and A groups. When A=CH, (II) can be prepared as described by Anderson et al [J. Med. Chem. (2007), 50, 2647-2654]. With A=N, and R1=hydrogen or F, the general synthesis below can be utilized. In the first step, a Stille coupling with (1-ethoxyethenyl)tributyltin is performed on a di-chloro-pyrimidine derivative (Va) [Langli et al, Tetrahedron (1996), 52, 5625-38]. The resulting enol ether derivative (VIa) can be brominated to α-bromoketone derivative (IIa) as described by Vanotti et al [J. Med. Chem. (2008), 51, 487-501]. Intermediates of the type (II) can be readily used in the Hantzsch or Paal-Knorr condensation reaction.

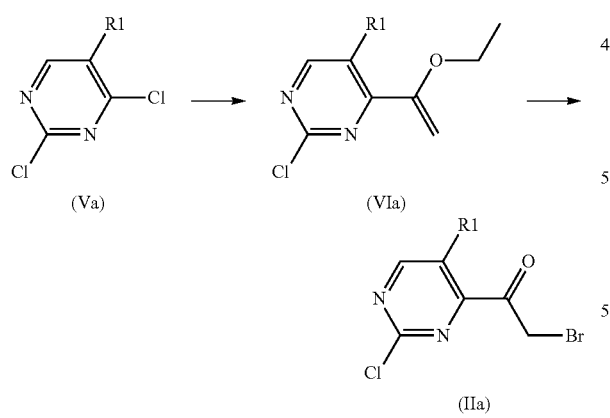

Type (III) intermediates can generally be prepared via acylation of (VIIa) with (chloroformyl)acetic acid esters and cyclization via a Dieckmann condensation to (VIII). Subsequent hydrolysis of the ester to the carboxylic acid and decarboxylation can be performed in acetonitrile/water mixtures at elevated temperatures [WO 2005013986]. Introduction of appropriate N-protecting groups (P), can be beneficial [Greene & Wuts, Protective Groups in Organic Synthesis, 3$^{rd}$ edition]. When R3=Boc, and P=PMB, DMB or TMB are utilized, protecting groups can be removed at any stage of the synthesis under acidic conditions such as TFA in DCM, or pure TFA at elevated temperatures [Vasse et al, Tetrahedron (2003), 59, 4911-4921].

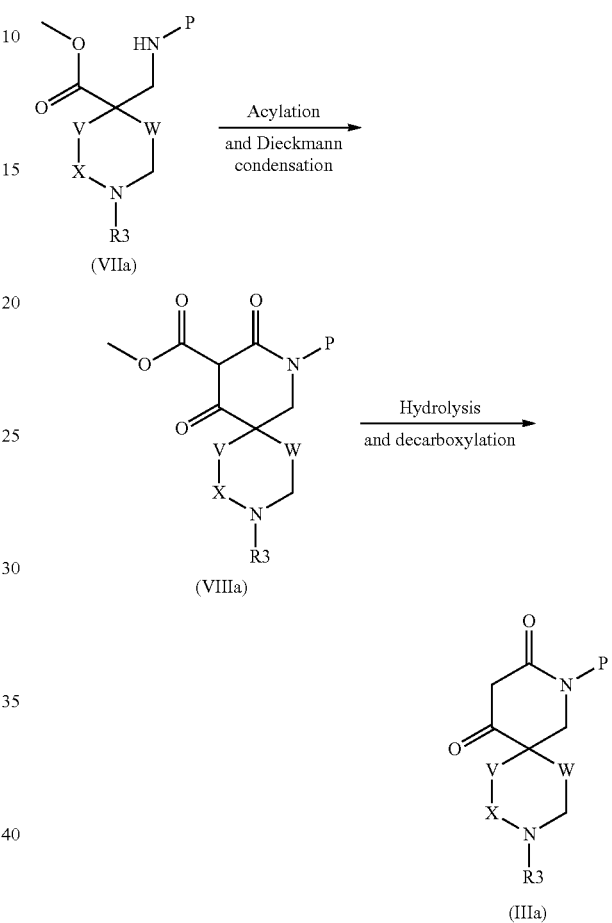

Protecting groups, such as PMB, DMB or TMB can be introduced via a reductive amination with (IX) and the prerequisite substituted benzaldehyde and sodium cyanoborohydride in MeOH. Alternatively, a nucleophilic substitution with (X) and the prerequisite benzylamine in acetonitrile at reflux can be effected to yield intermediate of type (VII). In this case, Q can be iodine, bromine, OTosyl or another appropriate leaving group.

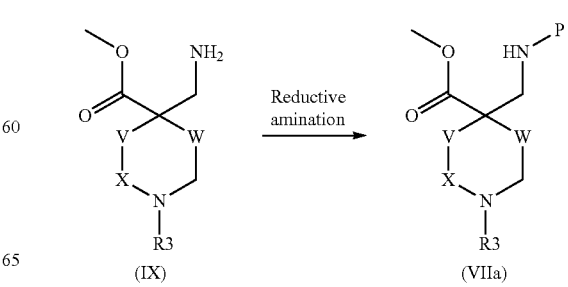

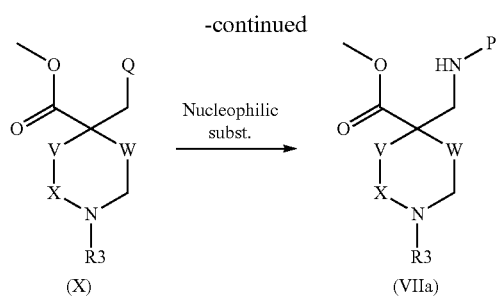

Intermediates of the type (VIII) are either commercially available, or the methylamino group can be introduced on (XI) via diiodomethane and an appropriate base such as LDA [Lombart et al, Bioorg. Med. Chem. Letters (2007), 17, 4333-4337]. Subsequent nucleophilic substitution with ammonia affords (VIII). Alternatively, sodium azide can be used as the nucleophile in the second step, followed by reduction to the primary amine.

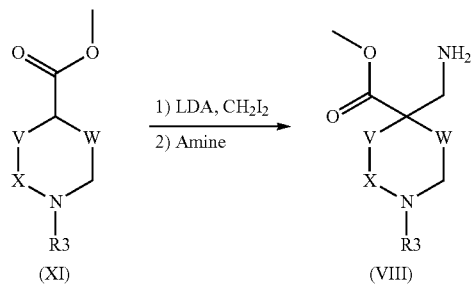

Intermediates of the type (VIII) can also be prepared via methylalcohol derivative (XII). This can be effected using LHMDS in THF and SEM chloride [Eichelberger et al, Tetrahedron (2002) 58, 545-559]. The SEM-group can be removed under acidic conditions such as TFA in DCM. Introduction of the appropriate leaving group and nucleophilic substitution as described above will afford (VIII).

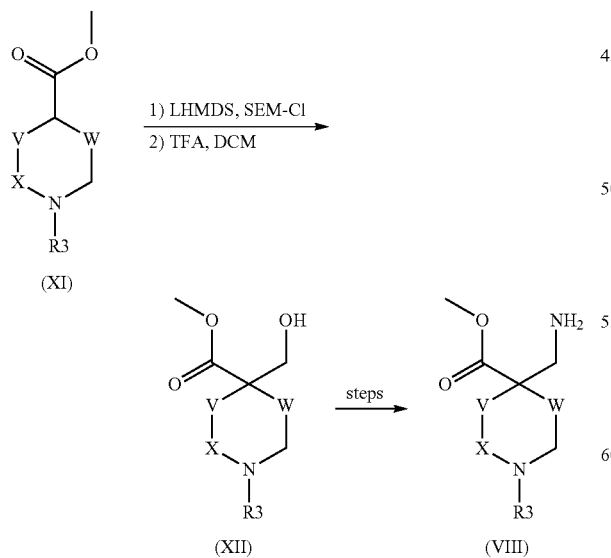

When V=CF$_2$, (XIb) can be prepared starting with commercially available (XIa) via fluorination with art known agents such as dialkylaminosulfur trifluorides (DAST, Deoxofluor®) directly on the ketone [Zhang et al, Bioorg. Med. Chem. Letters (2009) 19, 1101-1104]. Derivatives with V=CHF can be prepared via reduction of the ketone to the alcohol (XIc), followed by fluorination with the above mentioned fluorination agents [Bio et al, Synthesis (2008) 6, 891-896].

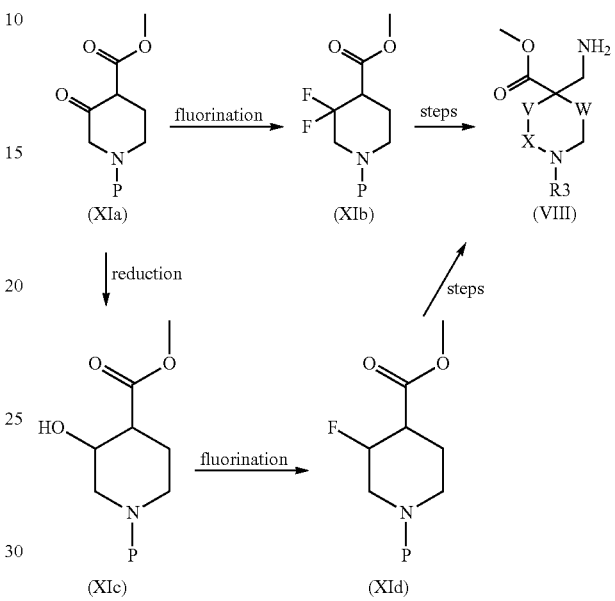

Yet another alternative for the preparation of intermediates of the type (VIII) is the use of a 1,3-dipole addition on electron-poor olefines. The construction of pyrrolidine ring can be effected by treating cyanoacrylate (XIII) with N-protected 1-methoxy-N-((trimethylsilyl)methyl) methanamine in TFA and DCM [Hosomi et al, Chem. Letters (1984) 7, 1117-1120]. Reduction of the resulting (XIV) can be done with hydrogen (gas) in MeOH using Ra—Ni as the catalyst.

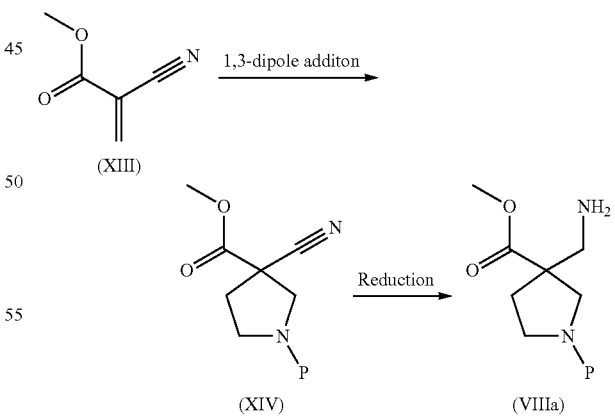

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The pyrrolo[3,2-c]pyridin]-4'(1'H)-one compounds of the invention were found to inhibit MK2. Methods to determine MK2 kinase inhibition as well as in vitro and in vivo assays to determine biological activity are well known. In one possible assay MK2 kinase is incubated with the compound to be tested and inhibition of phosphorylation of one of the proteins in the kinase pathway is measured.

In another assay the MK2 kinase activity can be determined by using an IMAP assay (Immobilized Metal Assay for Phosphochemicals—based coupled assay). IMAP is a homogeneous fluorescence polarization (FP) assay based on affinity capture of phosphorylated peptide substrates. IMAP uses fluorescein-labeled peptide substrates that, upon phosphorylation by a protein kinase, bind to so called IMAP nanoparticles, which are derivatized with trivalent metal complexes. Such binding causes a change in the rate of the molecular motion of the peptide, and results in an increase in the FP value observed for the fluorescein label attached to the substrate peptide. In such an assay, MK2 phosphorylates a fluorescein-labeled peptide substrate (see example 14).

The MK2 activity can also be determined in monocytic cell lines such as THP1 cells or in primary cell assays, e.g PBMC or whole blood from human rat or mouse Inhibition of MK2 activity can be investigated measuring LPS-induced TNFα and IL-6 production or phosphorylation of Hsp27 and TTP (Tristetraprolin). E.g. THP1 cells are stimulated with LPS, culture medium is collected after a 4 to 24 h incubation and cytokine production is quantified by ELISA.

Activity of MK2 inhibitors in vivo can be investigated in mouse and rat measuring the LPS-induced production of TNFcc and IL-6. In a typical experiment TNFcc and IL-6 are measured in blood of the animals 1.5 h and 4 h, respectively following LPS injection. TNFα and IL-6 levels are quantified by ELISA.

The solubility can be determined using the Automated Kinetic Aqueous Solubility (AKASol) method, which is an HPLC-UV based method. The method is derived from the classical saturated shake-flask solubility method which has been adapted to the 96-well microtitre plate format, allowing the use of DMSO stock solutions. The solubility is determined by measuring the amount of compound in a saturated aqueous solution, quantified by an external calibration curve of the compound dissolved in DMSO. The solubility (mg/L) is measured at pH 7.4, at room temperature and the final concentration of DMSO in the sample solution is 1%.

In another aspect the invention relates to a pharmaceutical composition which comprises a compound of formula I as previously described or a pharmaceutically acceptable salt thereof and one or more pharmaceutically acceptable excipients and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: The Science and Practice of Pharmacy [20th Edition., Lippincott Williams & Wilkins, 2000, see especially Part 5: Pharmaceutical Manufacturing], the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.1-1000 mg per kg body weight, preferably between 10-300 mg per kg body weight. The desired dose may be presented as one dose or as multiple subdoses administered at appropriate intervals throughout the day. The actual dosage employed may be varied depending on the requirements of the patient and the severity of the condition being treated by judgement of the skilled clinician Another aspect of the present invention relates to a method of treating or preventing a disease selected from immune, autoimmune and inflammatory diseases, cardiovascular diseases, infectious diseases, bone resorption disorders, neurodegenerative diseases and proliferative diseases, in a subject in the need thereof, especially a human being, which comprises administering to said subject a therapeutically effective amount of a compound of formula (I) or a pharmaceutically acceptable salt, solvate or prodrug thereof.

As mentioned previously, the compounds of the present invention act as MK2 inhibitors, inducing reduction of proinflammatory cytokines Therefore, these compounds are expected to be useful to treat or prevent diseases in which MK2 plays a role. This includes diseases where overproduction of cytokines such as TNFα, MCP-1, IL-1, IL-6 or IL-8, play a key regulatory role in disease initiation and/or progression. These diseases include, but are not limited to, immune, autoimmune and inflammatory diseases, cardiovascular diseases, infectious diseases, bone resorption disorders, neurodegenerative diseases and proliferative diseases. In particular, the compounds of the present invention are useful in the treatment of these diseases. More in particular, the compounds of the present invention are useful in the treatment of immune, autoimmune and inflammatory diseases.

Immune, autoimmune and inflammatory diseases that can be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), autoimmune hematologic disorders (e.g. hemolytic anemia, aplasic anemia, idiopathic thrombocytopenia, and neutropenia), autoimmune gastritis, and autoimmune inflammatory bowel diseases (e.g. ulcerative colitis and Crohn's disease), host versus graft disease, allograft rejection, chronic thyroiditis, Graves' disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, contact dermatitis, eczema, skin sunburns, vasculitis (e.g. Behcet's disease) chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Cardiovascular diseases that can be treated or prevented include, among others, myocardial infarction, cardiac hypertrophy, cardiac insufficiency, ischaemia-reperfusion disorders, thrombosis, thrombin-induced platelet aggregation, acute coronary syndromes, atherosclerosis and cerebrovascular accidents.

Infectious diseases that can be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that can be treated or prevented include osteoporosis, osteoarthritis, traumatic arthritis, gouty arthritis and bone disorders related with multiple myeloma, among others.

Neurodegenerative diseases that can be treated or prevented include, among others, Alzheimer's disease, Parkinson's disease, cerebral ischaemia, and traumatic neurodegenerative disease.

Proliferative diseases that can be treated or prevented include, among others, endometriosis, solid tumors, acute and chronic myeloid leukemia, Kaposi sarcoma, multiple myeloma, metastatic melanoma and angiogenic disorders such as ocular neovascularisation and infantile haemangioma.

The compounds according to the invention can be used in therapy. They can be used for the treatment of the above described disorders. In particular, they can be used for the treatment of rheumatoid arthritis, psoriasis or chronic obstructive pulmonary disease (COPD).

The MK2 inhibitory treatment defined hereinabove may be applied as a sole therapy or may involve, in addition to the compound of the invention, co-administration with other agent, including but not limited to inflammatory and immune modulating and analgesic agent; either small molecule or biologic.

The invention is illustrated by the following examples:

EXAMPLES

Abbreviations

Boc=t-butyl-carbamate
DCM=dichloromethane
DMB=2,4-dimethoxylbenzyl
DMF=dimethylformamide
DMSO=dimethyl sulfoxide
EtOAc=ethyl acetate
EtOH=ethanol
HPLC=High Performance Liquid Chromatography
$K_2CO_3$=potassium carbonate
LDA=lithium diisopropylamide
LHMDS=lithium hexamethyldisilazide
$MgSO_4$=magnesium sulfate
MeOH=methanol
NaCl=sodium chloride
$NaHCO_3$=sodium bicarbonate
$Na_2SO_4$=sodium sulfate
$NH_4O$=ammonium chloride
$NH_4OAc$=ammonium acetate
NMP=N-methylpyrrolidone
PMB=4-methoxybenzyl
SCX (−2)=Strong Cation Exchange SEM chloride=trimethylsilylethoxymethyl chloride
TBTU=O-(Benzotriazol-1-yl)-N,N,N',N'-1,1,3,3-tetramethyluronium tetrafluoroborate
TFA=trifluoroacetic acid
THF=tetrahydrofuran
TMB=2,4,6-trimethoxybenzyl
UPLC=Ultra High Performance Liquid Chromatography Purification If not stated otherwise, pure samples of the examples mentioned below were obtained using standard semi-preparative HPLC procedures denoted method A (acidic procedure) or B (basic procedure):

Method A:

A Gilson-system equipped with a Luna C-18 (150×21.2 mm, 5 μm) column. The used method was a 25-minute run, that consists of continuous flow of 0.3% TFA-solution in water combined with a 10-80% or 10-100% gradient of acetonitrile with water as the counter eluent.

Method B:

A Waters-system equipped with a XTerra MS C-18 (10×50 mm, 5 μm) column. The used method was a 7-minute run with a 10-100% gradient of acetonitrile with an aqueous 5 mM solution of ammonium bicarbonate as the counter eluent.

Analysis

If not stated otherwise, all synthesized intermediates and examples below, were analysed with LC-MS using the following standard method:

A Waters-LCMS-system equipped with an XBridge (C18, 3.5 μm, 4.6×20 mm) column. The used method was a 5-minute run with a 0-100% gradient of acetonitrile in water with a continuous flow of 0.05% TFA.

The names of the final products described in the examples were generated using the ChemDraw Ultra 9.0.7 program (version: 9.0.7.1009, CambridgeSoft Corp.

Example 1 1

Synthesis of 2'-(2-(benzofuran-2-yl)pyrimidin-4-yl)-5',6'-dihydrospiro[piperidine-4,7'-pyrrolo[3,2-c]pyridin]-4(1'H)-one Derivatives (A7)

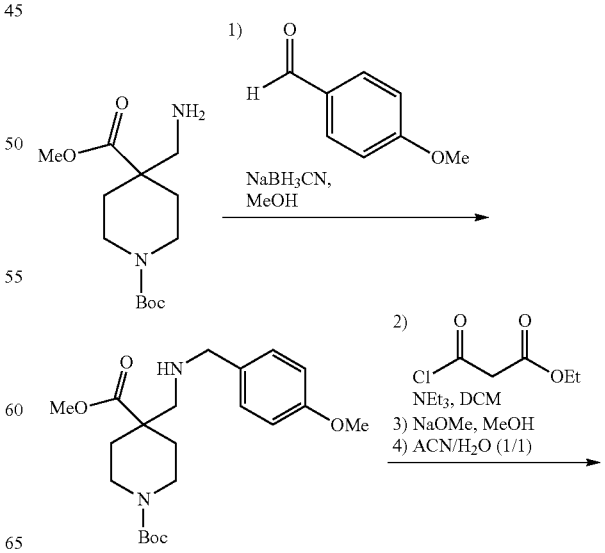

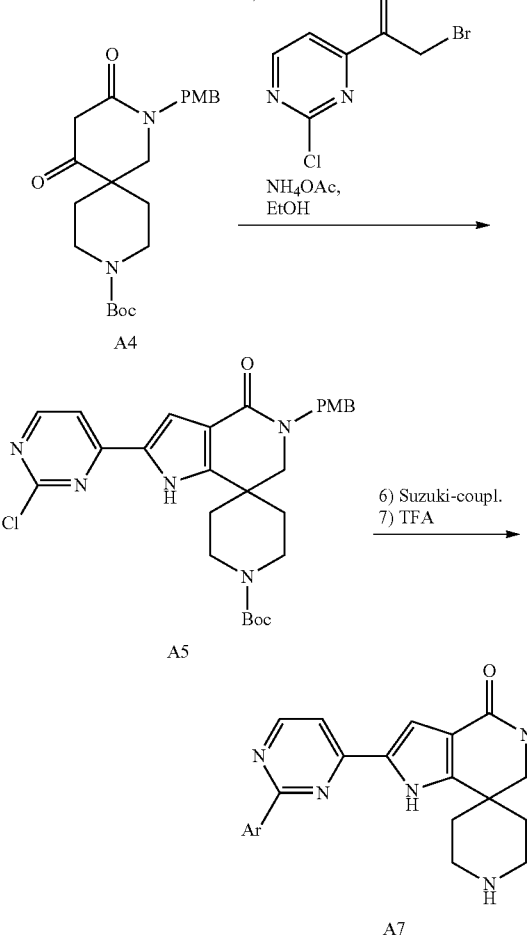

Step 1: 1-tert-butyl 4-methyl 4-((4-methoxybenzylamino)methyl)piperidine-1,4-dicarboxylate (A1)

Commercial available 1-tert-butyl 4-methyl 4-(aminomethyl)piperidine-1,4-dicarboxylate (10.10 mmol, 2.75 g) and 4-methoxybenzaldehyde (15.15 mmol, 2.062 g) in anhydrous MeOH (40 mL) were stirred for 2 h at rt. After addition of sodium cyanoborohydride (20.19 mmol, 1.269 g) the reaction was stirred overnight at 45° C. The mixture was evaporated in vacuo, and solved in EtOAc and sat. aq. bicarb. After separation of the organic phase, the aq. phase was extracted with EtOAc. The combined organic phase was dried over MgSO$_4$ and evaporated in vacuo. The crude was purified by flash chromatography (heptane/EtOAc: 10 to 100%) yielding 2.3 g oil (58%). $^1$H NMR (400 MHz, CDCl$_3$, 300K): δ=1.40 (2H, s), 1.45 (9H, s), 2.07 (2H, dt, J=13.3 Hz, J=3.4 Hz), 2.66 (2H, m), 2.94 (2H, m), 3.68 (2H, s), 3.70 (3H, s), 3.76 (2H, m), 3.79 (3H, s), 6.85 (2H, d, J=8.3 Hz), 7.19 (2H, d, J=8.3 Hz). $^{13}$C NMR (100 MHz, CDCl$_3$, 300K): δ=28.8, 31.9, 47.3, 52.3, 53.9, 55.7, 57.3, 79.8, 114.0, 129.4, 132.8, 155.2, 159.0, 176.1. MS (ES) C$_{21}$H$_{32}$N$_2$O$_5$ requires: 392. found: 393.3 [M+H]$^+$.

Step 2: 1-tert-butyl 4-methyl 4((3-ethoxy-N-(4-methoxybenzyl)-3-oxopropanamido)methyl)piperidine-1,4-dicarboxylate (A2)

A1 (5.61 mmol, 2.2 g), 4-dimethylaminopyridine (0.561 mmol, 0.068 g) and pyridine (16.82 mmol, 1.357 mL, 1.330 g) were dissolved in anhydrous DCM (25 mL), then (chloroformyl)acetic acid ethyl ester (6.17 mmol, 0.862 mL, 1.031 g) in DCM (5 mL) was added slowly and the solution was stirred for 2 h at RT. The mixture was poured into 1M HCl and extracted twice with EtOAc. The organic layer was washed with sat. NaCl, dried over MgSO$_4$, filtered and concentrated in vacuo. The crude was purified by flash chromatography (heptane/EtOAc: 10 to 80%) yielding 2.6 g oil which was a mixture of the desired product A2 and an unknown related product. MS (ES) C$_{26}$H$_{38}$N$_2$O$_8$ requires: 506. found: 507.2 [M+H]$^+$.

Step 3: 9-tert-butyl 4-methyl 2-(4-methoxybenzyl)-3,5-dioxo-2,9-diazaspiro[5.5]undecane-4,9-dicarboxylate (A3)

The mixture from Step 2 was dissolved in anhydrous MeOH (50 mL), sodium methoxide (25.6 mmol, 1.384 g) was added and then the suspension was stirred for 15 h at 60° C. The reaction mixture was concentrated in vacuo, taken up in 2 N HCl and extracted with DCM. The organic layer was dried over MgSO$_4$, filtered and concentrated in vacuo yielding the desired product A3 (2.02 g) as an oil. MS (ES) C$_{24}$H$_{32}$N$_2$O$_7$ requires: 460. found: 461.2 [M+H]$^+$.

Step 4: tert-butyl 2-(4-methoxybenzyl)-3,5-dioxo-2,9-diazaspiro[5.5]undecane-9-carboxylate (A4)

Crude product A3 was dissolved in acetonitrile (50 mL) and water (50 mL) and stirred for 4 h at 80° C. The acetonitrile was evaporated off and the solids were filtered off, washed with water and taken up in DCM. The organic phase was dried over Na$_2$SO$_4$ and concentrated in vacuo. The product A4 (1.57 g) was obtained as a white solid. Overall yields (A2 to A4) are 70%. $^1$H NMR (400 MHz, CDCl$_3$, 300K): δ=1.23 (2H, m), 1.41 (9H, s), 1.76 (2H, m), 3.13 (2H, m), 3.26 (2H, s), 3.37 (2H, m), 3.39 (2H, s), 3.81 (3H, s), 4.58 (2H, s), 6.87 (2H, d, J=8.6 Hz), 7.22 (d, J=8.6 Hz). $^{13}$C NMR (100 MHz, CDCl$_3$, 300K): δ=28.8, 30.0, 46.3, 47.1, 49.8, 51.7, 55.7, 80.2, 114.6, 128.4, 130.5, 154.9, 159.8, 166.4, 206.8. MS (ES) C$_{22}$H$_{30}$N$_2$O$_5$ requires: 402. found: 425.2 [M+Na]$^+$.

Step 5: tert-butyl 2'(2-chloropyrimidin-4-yl)-5'-(4-methoxybenzyl)-4'-oxo-1',4',5',6'-tetrahydrospiro[piperidine-4,7'-pyrrolo[3,2-c]pyridine]-1-carboxylate (A5)

A4 (3.98 mmol, 1.6 g) and NH$_4$OAc (11.93 mmol, 0.919 g) were solved in EtOH (100 mL) for 15 min. Then 2-bromo-1-(2-chloropyrimidin-4-yl)ethanone (3.98 mmol, 0.936 g) was added and the mixture was stirred overnight at RT. The mixture was evaporated in vacuo. The crude was dissolved in EtOAc (400 mL) and washed twice with 1 N HCl and once with brine. The organic phase was dried over MgSO$_4$ and evaporated in vacuo. Purification by flash chromatography (Hept: 10 to 100% EtOAc) yielded A5 as a yellow solid 1.32 g, 61%). $^1$H NMR (400 MHz, CDCl$_3$, 300K): δ=1.45 (9H, s), 1.64 (2H, m), 1.78 (2H, m), 2.56 (2H, m), 3.13 (1H, m), 3.37 (1H, m), 3.46 (2H, s), 3.80 (3H, s), 4.65 (2H, s), 6.87 (2H, d, J=8.7 Hz), 7.24 (2H, d, J=8.7 Hz), 7.32 (1H, d, J=2.1 Hz), 7.37 (1H, d, J=5.5 Hz), 8.46 (1H, d, J=5.5 Hz), 9.64 (1H, br s). MS (ES) C$_{28}$H$_{32}$ClN$_5$O$_4$ requires: 537. found: 538.2 [M+H]$^+$.

Step 6: tert-butyl 2'-(2-(benzofuran-2-yl)pyrimidin-4-yl)-5'-(4-methoxybenzyl)-4'-oxo-1',4',5',6'-tetrahydrospiro[piperidine-4,7'-pyrrolo[3,2-c]pyridine]-1-carboxylate (A6)

A mixture of tert-butyl 2'-(2-chloropyrimidin-4-yl)-5'-(4-methoxybenzyl)-4'-oxo-1',4',5',6'-tetrahydrospiro[piperidine-4,7'-pyrrolo[3,2-c]pyridine]-1-carboxylate (A5) (4.5 g, 8.36 mmol), 2-benzofuranboronic acid (4.06 g, 25.09 mmol) and potassium phosphate tribasic heptahydrate (8.49 g, 25.09 mmol) was dissolved in anhydrous dioxane (105 mL). The resulting solution was purged with nitrogen, followed by addition of 1,1'-bis(diphenylphosphino)ferrocene palladium (II)chloride (676 mg, 0.836 mmol). The resulting mixture was again purged with nitrogen and stirred at 140° C. for 45 min in the microwave. After cooling to room temperature, the reaction mixture was diluted with EtOAc, washed three times with aqueous NaHCO$_3$, once with brine, dried over Na$_2$SO$_4$, filtered and concentrated under vacuum. The crude product was triturated with toluene which gave tert-butyl 2'-(2-(benzofuran-2-yl)pyrimidin-4-yl)-5'-(4-methoxybenzyl)-4'-oxo-1',4',5',6'-tetrahydro spiro [piperidine-4,7'-pyrrolo[3,2-c]pyridine]-1-carboxylate (A6) as a white solid (3.60 g, 70%). $^1$H NMR (400 MHz, DMSO-D6, 300K): δ=1.42 (9H, s), 1.55 (2H, br d, J=13.0 Hz), 2.08 (2H, br dt, J=13.4 Hz), 2.65 (2H, br s), 3.56 (2H, br s), 3.74 (3H, s), 3.80 (2H, br s), 4.57 (2H, br s), 6.92 (2H, d, J=8.6 Hz), 7.31 (2H, d, J=8.6 Hz), 7.35 (1H, t, J=7.6 Hz), 7.43 (1H, s), 7.46 (1H, t, J=7.8 Hz), 7.75 (1H, d, J=8.2 Hz), 7.80 (1H, d, J=5.5 Hz), 7.82 (1H, d, J=7.7 Hz), 8.03 (1H, s), 8.77 (1H, d, J=5.4 Hz), 11.75 (1H, s). MS (ES) $C_{36}H_{37}N_5O_5$ requires: 619. found: 620.2 [M+H]$^+$.

Step 7: Example 1_1: 2'(2-(benzofuran-2-yl)pyrimidin-4-yl)-5',6'-dihydrospiro[piperidine-4,7'-pyrrolo[3,2-c]pyridin]-4'(1'H)-one A6 (3.60 g, 5.81 mmol) was dissolved in TFA (29.0 mL). The mixture was stirred at 140° C. for 40 min in the microwave. After cooling to room temperature, the reaction mixture was concentrated under vacuum. The crude product was purified by Strong Cation Exchange (SCX) with MeOH as eluent, followed by rinsing with 0.7 N NH$_3$ in MeOH to obtain the pure free base as yellow solid (2.22 g). $^1$H NMR (400 MHz, DMSO-D6, 300K): δ=1.64 (2H, d, J=12.8 Hz), 2.15 (2H, br dt, J=13.0 Hz), 2.71 (2H, t, J=11.9 Hz), 2.89 (2H, d, J=11.2 Hz), 3.46 (2H, s), 4.12 (1H, br s), 7.24 (1H, s), 7.35 (1H, t, J=7.4 Hz), 7.37 (1H, s), 7.46 (1H, t, J=7.4 Hz), 7.75 (1H, d, J=8.2 Hz), 7.81 (1H, d, J=5.6 Hz), 7.83 (1H, d, J=8.6 Hz), 8.09 (1H, s), 8.76 (1H, d, J=5.4 Hz), 11.78 (1H, br s); MS (ES) $C_{23}H_{21}N_5O_2$ requires: 399. found: 400.1 [M+H]$^+$.

The following example(s) were prepared according to this method:

Example 1_2

2'-(2'-amino-2,5'-bipyrimidin-4-yl)-5',6'-dihydrospiro[piperidine-4,7'-pyrrolo[3,2-c]pyridin]-4'(1'H)-one The title compound was prepared following the general procedure reported for Example 1_1 using 2-aminopyrimidin-5-ylboronic acid and was purified by semi-preparative HPLC (method B). MS (ES) $C_{19}H_{20}N_8O$ requires: 376. found: 377.2 [M+H]$^+$.

Example 1_3

2'-(2-(5-methoxypyridin-3-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 5-methoxypyridin-3-ylboronic acid and was purified by semi-preparative HPLC (method B). MS (ES) $C_{21}H_{22}N_6O_2$ requires: 390. found: 391.2 [M+H]$^+$.

Example 1_4

2'-(2-(2-fluorophenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 2-fluorophenylboronic acid and was purified by semi-preparative HPLC (method B). MS (ES) $C_{21}H_{20}FN_5O$ requires: 377. found: 378.2 [M+H]$^+$.

Example 1_5

2'-(2-(3-fluorophenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-fluorophenylboronic acid and was purified by semi-preparative HPLC (method B). MS (ES) $C_{21}H_{20}FN_5O$ requires: 377. found: 378.1 [M+H]$^+$.

Example 1_6

2'-(2-(4-acetylphenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 4-acetylphenylboronic acid, purified by semi-preparative HPLC (method A) and isolated as a TFA-salt. $^1$H NMR (400 MHz, DMSO-D6, 300K): δ=1.91 (2H, br d, J=14.1 Hz), 2.33 (2H, dt, J1=14.1 Hz, J2=3.9 Hz), 2.66 (3H, s), 3.12 (2H, q, 12.2 Hz), 3.53 (2H, d, J=2.0 Hz), 7.43 (2H, m), 7.88 (1H, d, J=5.5 Hz), 8.11 (2H, d, J=8.3 Hz), 8.37 (1H, m), 8.72 (2H, d, J=8.3 Hz), 8.73 (1H, m), 8.85 (1H, d, J=5.5 Hz), 11.83 (1H, s); MS (ES) $C_{23}H_{23}N_5O_2$ requires: 401. found: 402.3 [M+H]$^+$.

Example 1_7

2'-(2-(benzo[d][1,3]dioxol-5-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3,4-methylendioxybenzeneboronic acid, purified by semi-preparative HPLC (method A) and isolated as a TFA-salt. $^1$H NMR (400 MHz, DMSO-D6, 300K): δ=1.91 (2H, d, J=14.1 Hz), 2.31 (2H, br t, J=14.1 Hz), 3.12 (2H, q, J=12.2 Hz), 3.31 (2H, m), 6.17 (2H, s), 7.07 (1H, d, J=8.3 Hz), 7.35 (1H, d, J=1.8 Hz), 7.40 (1H, br s), 7.73 (1H, d, J=5.5 Hz), 8.15 (1H, d, J=1.2 Hz), 8.20 (1H, dd, J1=8.3 Hz, J2=1.2 Hz), 8.27 (1H, br s), 8.71 (1H, br s), 8.72 (1H, d, J=5.5 Hz), 11.74 (1H, s); MS (ES) $C_{22}H_{21}N_5O_3$ requires: 403. found: 404.3 [M+H]$^+$.

Example 1_8

N-(5-(4-(4'-oxo-1',4',5',6'-tetrahydrospiro[piperidine-4,7'-pyrrolo[3,2-c]pyridine]-2'-yl)pyrimidin-2-yl)pyridin-2-yl)acetamide The title compound was prepared following the general procedure reported for Example 1_1 step 6, using 2-amino-5-(4,4,5,5-tetramethyl-1,3,2-dioxaborolan-2-yl)pyridine. To a solution of this intermediate Suzuki product (0.053 mmol, 25 mg) in DCM (800 μL) and pyridine (200 μL) was added acetyl chloride (0.053 mmol, 3.75 μL) at 0° C. The reaction mixture was stirred at ambient temperature overnight. Additional aliquots of acetyl chloride (4 eq. in total) were added between 24 and 36 h, until the reaction was complete. The reaction mixture was diluted in EtOAc en washed once with water. The organic layer was washed with brine and dried over $MgSO_4$. After filtration and evaporation the crude mixture was purified by flash column chromatography on silica gel, eluting with DCM/MeOH. Evaporation of pure fractions gave the N-acetylated intermediate as a white solid. The intermediate (0.028 mmol, 14.5 mg) was N-Boc deprotected in MeOH with 4 N HCl in dioxane (1 mL). The reaction mixture was stirred at ambient temperature for 2 h. Evaporation in vacuo afforded the title compound as the di-HCl salt. MS (ES) $C_{22}H_{23}N_7O_2$ requires: 417. found: 418.2 $[M+H]^+$.

Example 1_9

N-(5-(4-(4'-oxo-1',4',5',6'-tetrahydrospiro[piperidine-4,7'-pyrrolo[3,2-c]pyridine]-2'-yl)pyrimidin-2-yl)pyridin-2-yl)propionamide The title compound was prepared following the general procedure reported for Example 1_13 using propionyl chloride, and isolated as the di-HCl salt. MS (ES) $C_{23}H_{25}N_7O_2$ requires: 431. found: 432.2 $[M+H]^+$.

Example 1_10

2'-(2-(3-chloro-4-(trifluoromethyl)phenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-chloro-4-(trifluoromethyl)phenylboronic acid, purified by semi-preparative HPLC (method A) and isolated as a TFA-salt. $^1$H NMR (400 MHz, DMSO-D6, 300K): δ=1.92 (2H, br d, J=13.4 Hz), 2.32 (2H, m), 3.12 (2H, m), 3.53 (2H, d, J=2.0 Hz), 7.44 (1H, br s), 7.46 (1H, d, J=2.0), 7.93 (1H, d, J=5.1 Hz), 8.04 (1H, d, J=8.3 Hz), 8.72 (1H, br s), 8.86 (1H, d, J=5.1 Hz), 8.89 (1H, s), 11.91 (1H, s); MS (ES) $C_{22}H_{19}ClF_3N_5O$ requires: 461. found: 461.1 $[M+H]^+$.

Example 1_11

2'-(2-(3,4-dihydro-2H-benzo[b][1,4]dioxepin-7-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3,4-dihydro-2H-benzo[b][1,4]dioxepin-7-ylboronic acid, purified by semi-preparative HPLC (method A) and isolated as a TFA-salt. $^1$H NMR (400 MHz, DMSO-D6, 300K): δ=1.90 (2H, br d, J=14.1 Hz), 2.17 (2H, quint, J=5.5 Hz), 2.31 (2H, m), 3.11 (2H, m), 3.52 (2H, d, J=2.0 Hz), 4.22 (4H, q, J=5.5 Hz), 7.10 (1H, d, J=8.3 Hz), 7.35 (1H, d, J=2.4 Hz), 7.40 (1H, br s), 7.74 (1H, d, J=5.5 Hz), 8.18 (1H, dd, J1=8.3 Hz, J2=2.0 Hz), 8.21 (1H, d, J=2.0 Hz), 8.30 (1H, m), 8.73 (1H, d, J=5.5 Hz), 8.74 (br s), 11.80 (1H, s); MS (ES) $C_{24}H_{25}N_5O_3$ requires: 431. found: 431.2 $[M+H]^+$.

Example 1_12

2'-(2-(biphenyl-4-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using (1,1'-biphenyl-4-yl)boronic acid, purified by semi-preparative HPLC (method A) and isolated as a TFA-salt. MS (ES) $C_{27}H_{25}N_5O$ requires: 435. found: 436.2 $[M+H]^+$.

Example 1_13

2'-(2-(3,4-dichlorophenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3,4-dichlorophenylboronic acid, purified by semi-preparative HPLC (method A) and isolated as a TFA-salt. MS (ES) $C_{21}H_{19}Cl_2N_5O$ requires: 427. found: 428.1 $[M+H]^+$.

Example 1_14

2'-(2-(3-isopropylphenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-isopropylbenzeneboronic acid, purified by semi-preparative HPLC (method A) and isolated as a TFA-salt. MS (ES) $C_{24}H_{27}N_5O$ requires: 401. found: 402.2 $[M+H]^+$.

Example 1_15

2'-(2-(4-phenoxyphenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 4-phenoxyphenylboronic acid, purified by semi-preparative HPLC (method A) and isolated as a TFA-salt. MS (ES) $C_{27}H_{25}N_5O_2$ requires: 451. found: 452.2 $[M+H]^+$.

Example 1_16

2'-(2-(3-(trifluoromethoxy)phenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-(trifluoromethoxy)phenylboronic acid, purified by semi-preparative HPLC (method A) and isolated as a TFA-salt. MS (ES) $C_{22}H_{20}F_3N_5O_2$ requires: 443. found: 444.2 $[M+H]^+$.

Example 1 17

2'-(2-(4-(trifluoromethyl)phenyl)pyrimidin-4-yl)-5', 6'-dihydrospiro[piperidine-4,7'-pyrrolo[3,2-c]pyridin]-4'(1'H)-one

The title compound was prepared following the general procedure reported for Example 1_1 using 4-trifluoromethylbenzeneboronic acid, purified by semi-preparative HPLC (method A) and isolated as a TFA-salt. MS (ES) $C_{22}H_{20}F_3N_5O$ requires: 427. found: 428.1 $[M+H]^+$.

Example 1 18

2'-(2-(4-cyclohexylphenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 4-cyclohexylphenylboronic acid, purified by semi-preparative HPLC (method A) and isolated as a TFA-salt. $^1$H NMR (400 MHz, DMSO-D6, 300K): δ=1.21-1.53 (6H, m), 1.69-1.95 (7H, m), 2.30 (2H, m), 3.12 (2H, m), 3.30 (2H, m), 3.52 (2H, d, J=2.0 Hz), 7.38 (4H, m), 7.77 (1H, d, J=5.5 Hz), 8.28 (1H, m), 8.49 (2H, d, J=8.6 Hz), 8.71 (1H, m), 8.77 (1H, d, J=5.5 Hz), 11.76 (1H, s); MS (ES) $C_{27}H_{31}N_5O$ requires: 441. found: 442.4 $[M+H]^+$.

Example 1 19

2'-(2-(3-tert-butyl-5-methylphenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 3-tert-butyl-5-methylphenylboronic acid, purified by semi-preparative HPLC (method A) and isolated as a TFA-salt. $^1$H NMR (400 MHz, DMSO-D6, 300K): δ=1.36 (9H, s), 1.92 (2H, br d, J=13.8 Hz), 2.28 (2H, dt, J1=13.8 Hz, J2=3.5 Hz), 2.44 (3H, s), 3.12 ((2H, q, J=11.8 Hz), 3.34 (2H, m), 3.52 (2H, d, J=2.0 Hz), 7.36 (1H, d, J=2.0 Hz), 7.41 (1H, br d, J=5.9 Hz), 7.80 (1H, d, J=5.9 Hz), 8.26 (1H, s), 8.31 (1H, m), 8.33 (1H, s), 8.75 (1H, br d, J=11.0 Hz), 8.80 (1H, d, J=5.1 Hz), 11.83 (1H, s); MS (ES) $C_{26}H_{31}N_5O$ requires: 429. found: 430.4 $[M+H]^+$.

Example 1 20

2'-(2-(4-hydroxy-3-methoxyphenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 4-(benzyloxy)-3-methoxyphenylboronic acid, purified by semi-preparative HPLC (method A) and isolated as a TFA-salt. $^1$H NMR (400 MHz, DMSO-D6, 300K): δ=1.90 (2H, br d, J=13.8 Hz), 2.29 (2H, dt, J1=13.8 Hz, J2=3.5 Hz), 3.11 (2H, q, J=11.8 Hz), 3.32 (2H, m), 3.51 (2H, br s), 3.89 (3H, s), 7.77 (1H, d, J=1.2 Hz), 7.40 (1H, br s), 7.69 (1H, d, J=5.5 Hz), 8.07 (1H, d, J=1.2 Hz), 8.14 (1H, d, J=8.3 Hz), 8.29 (1H, m), 8.71 (1H, d, J=5.5 Hz), 8.72 (1H, br s), 9.56 (1H, br s), 11.75 (1H, s); MS (ES) $C_{22}H_{23}N_5O_3$ requires: 405. found: 406.2 $[M+H]^+$.

Example 1 21

2'-(2-(quinolin-3-yl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using quinolin-3-ylboronic acid and was purified by semi-preparative HPLC (method B). MS (ES) $C_{24}H_{22}N_6O$ requires: 410. found: 411.2 $[M+H]^+$.

Example 1 22

2'-(2-(4-tert-butylphenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 4-tert-butylphenylboronic acid, purified by semi-preparative HPLC (method A) and isolated as a TFA-salt. MS (ES) $C_{25}H_{29}N_5O$ requires: 415. found: 416.2 $[M+H]^+$.

Example 1 23

2'-(2-(4-isobutylphenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 4-isobutylphenylboronic acid, purified by semi-preparative HPLC (method A) and isolated as a TFA-salt. MS (ES) $C_{25}H_{29}N_5O$ requires: 415. found: 416.2 $[M+H]^+$.

Example 1 24

2'-(2-(naphthalen-2-yl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using naphthalen-2-ylboronic acid, purified by semi-preparative HPLC (method A) and isolated as a TFA-salt. MS (ES) $C_{25}H_{23}N_5O$ requires: 409. found: 410.2 $[M+H]^+$.

Example 1 25

2'-(2-(3,5-dichlorophenyl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 3,5-dichlorophenylboronic acid (50% in THF/water (9:1), purified by semi-preparative HPLC (method A) and isolated as a TFA-salt. MS (ES) $C_{21}H_{19}Cl_2N_5O$ requires: 427. found: 428.1 $[M+H]^+$.

Example 1 26

2'-(2-(dibenzo[b,d]furan-2-yl)pyrimidin-4-yl)-5',6'-dihydrospiro[piperidine-4,7'-pyrrolo[3,2-c]pyridin]-4'(1'H)-one

The title compound was prepared following the general procedure reported for Example 1_1 using 2-(dibenzo[b,d]

furan-2-yl)-4,4,5,5-tetramethyl-1,3,2-dioxaborolane, purified by semi-preparative HPLC (method A) and isolated as a TFA-salt. MS (ES) $C_{27}H_{23}N_5O_2$ requires: 449. found: 450.2 $[M+H]^+$.

Example 1 27

2'-(2-(4-isobutoxyphenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 4-isobutoxyphenylboronic acid, purified by semi-preparative HPLC (method A) and isolated as a TFA-salt. MS (ES) $C_{25}H_{29}N_5O_2$ requires: 431. found: 432.2 $[M+H]^+$.

Example 1 28

2'-(2-(benzo[b]thiophen-2-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using benzo[b]thiophen-2-ylboronic acid, purified by semi-preparative HPLC (method A) and isolated as a TFA-salt. $^1$H NMR (400 MHz, DMSO-D6, 300K): δ=1.93 (2H, br d, J=13.8 Hz), 2.33 (2H, dt, J1=14.2 Hz, J2=3.5 Hz), 3.13 (2H, m), 3.54 (2H, d, J=2.3 Hz), 7.40-7.49 (4H, m), 7.81 (1H, d, J=5.4 Hz), 7.96 (1H, m), 8.05 (1H, m) 8.41 (1H, m) 8.57 (1H, s), 8.74 (1H, br s), 8.77 (1H, d, J=5.4 Hz), 11.81 (1H, s); MS (ES) $C_{23}H_{21}N_5OS$ requires: 415. found: 416.2 $[M+H]^+$.

Example 1 29

3-(4-(4'-oxo-1',4',5',6'-tetrahydrospiro[piperidine-4,7'-pyrrolo[3,2-c]pyridine]-2'-yl)pyrimidin-2-yl)benzamide The title compound was prepared following the general procedure reported for Example 1_1 using 3-acetylphenylboronic acid, purified by semi-preparative HPLC (method A) and isolated as a TFA-salt. $^1$H NMR (400 MHz, DMSO-D6, 300K): δ=1.92 (2H, d, J=14.2 Hz), 2.31 (2H, dt, J1=14.2 Hz, J2=3.8 Hz), 3.12 (2H, q, J=11.9 Hz), 3.32 (2H, m), 7.42 (1H, d, 1.9 Hz), 7.48 (1H, s), 7.63 (1H, t, J=7.7 Hz), 7.85 (1H, d, J=5.4 Hz), 8.03 (1H, d, J=8.0 Hz), 8.15 (1H, s), 8.36 (1H, m), 8.74 (1H, br s) 8.77 (1H, d, J=8.0 Hz), 8.84 (1H, d, J=5.4 Hz), 8.98 (1H, s), 11.81 (1H, s); MS (ES) $C_{22}H_{22}N_6O_2$ requires: 402. found: 403.3 $[M+H]^+$.

Example 1 30

2'-(2-(3-acetylphenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-acetylphenyl-boronic acid, purified by semi-preparative HPLC (method A) and isolated as a TFA-salt. $^1$H NMR (400 MHz, DMSO-D6, 300K): δ=1.92 (2H, br d, J=13.8 Hz), 2.30 (2H, dt, J1=13.8 Hz, J2=3.5 Hz), 3.12 (2H, q, J=12.1 Hz), 3.53 (2H, d, J=2.1 Hz), 7.41 (1H, d, J=2.1 Hz), 7.43 (1H, m), 7.72 (1H, t, J=7.7 Hz), 7.87 (1H, d, J=5.4 Hz), 8.16 (1H, d, J=7.7 Hz), 8.32 (1H, m), 8.73 (1H, m), 8.85 (1H, d, J=5.4 Hz), 8.89 (1H, d, J=8.0 Hz), 9.05 (1H, s), 11.86 (1H, s); MS (ES) $C_{23}H_{23}N_5O_2$ requires: 401. found: 402.2 $[M+H]^+$.

Example 1 31

2-chloro-N-cyclohexyl-4-(4-(4'-oxo-1',4',5',6'-tetrahydrospiro[piperidine-4,7'-pyrrolo[3,2-c]pyridine]-2'-yl)pyrimidin-2-yl)benzamide The title compound was prepared following the general procedure reported for Example 1_1 using 3-chloro-4-(cyclohexylcarbamoyl)phenylboronic, purified by semi-preparative HPLC (Method A) and was isolated as TFA-salt. $^1$H NMR (400 MHz, DMSO-D6, 300K): δ=1.15 (1H br t, J=12.0 Hz), 1.30 (4H, m, J=10.1 Hz), 1.59 (1H, d, J=12.6 Hz), 1.72 (1H, d, J=2.4 Hz), 1.75 (1H, d, J=4.0 Hz), 1.88 (3H, m, J=9.3 Hz), 1.94 (1H, s), 2.33 (2H, dt, J1=4.0 Hz, J2=14.2 Hz), 3.12 (2H, q, J=11.7 Hz), 3.33 (2H, d, J=11.9 Hz), 3.53 (2H, s), 3.75 (1H, br s), 7.43 (1H, m, J=2.3 Hz), 7.54 (1H, d, J=8.1 Hz), 7.87 (1H, d, J=5.4 Hz), 8.38 (1H, br d, J=10.8 Hz), 8.45 (1H, d, J=7.7 Hz), 8.57 (1H, d, J=1.4 Hz), 8.68 (1H, d, J=1.6 Hz), 8.78 (1H, br d, J=10.5 Hz), 8.82 (1H, d, J=5.4 Hz), 11.89 (1H, s); MS (ES) $C_{28}H_{31}N_6O_2$ requires: 519. found: 519.2 [M].

Example 1 32

2'-(2-(4-chloro-2-fluorophenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 4-chloro-2-fluorophenylboronic acid, purified by semi-preparative HPLC (Method A) and isolated as TFA-salt. $^1$H NMR (400 MHz, DMSO-D6, 300K): δ=1.89 (2H, d, J=14.3 Hz), 2.27 (2H, dt, J1=3.6 Hz, J2=15.0 Hz), 3.10 (2H, q, J=10.7 Hz), 3.30 (2H, d, J=12.0 Hz), 3.51 (2H, s), 7.36 (1H, d, J=2.3 Hz), 7.42 (1H, br s), 7.46 (1H, dd, J1=1.5 Hz, J2=8.7 Hz), 7.61 (1H, dd, J1=1.5 Hz, J2=10.8 Hz), 7.87 (1H, d, J=5.1 Hz), 8.26 (2H, t, J=8.7 Hz), 8.74 (1H, d, J=10.7 Hz), 8.84 (1H, d, J=5.6 Hz), 11.76 (1H, s); MS (ES) $C_{21}H_{19}ClFN_5O$ requires: 411. found: 412.1 $[M+H]^+$.

Example 1 33

2'-(2-(biphenyl-3-yl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using biphenyl-3-ylboronic acid, purified by semi-preparative HPLC (Method A) and was isolated as TFA-salt. $^1$H NMR (400 MHz, DMSO-D6, 300K): δ=1.92 (2H, d, J=13.7 Hz), 2.31 (2H, dt, J1=4.7 Hz, J2=14.1 Hz), 3.12 (2H, q, J=12.5 Hz), 3.32 (2H, d, J=12.1 Hz), 3.53 (2H, d, J=2.3 Hz), 7.40 (1H, d, J=2.3 Hz), 7.43 (1H, t, J=7.4 Hz), 7.54 (1H, t, J=7.8 Hz), 7.66 (1H, t, J=7.8 Hz), 7.78 (2H, d, J=7.0 Hz), 7.85 (2H, d, J=5.5 Hz), 8.36 (1H, br d, J=9.3 Hz), 8.65 (1H, d, J=7.8 Hz), 8.77 (2H, s), 8.84 (1H, d, J=5.5 Hz), 11.84 (1H, s); MS (ES) $C_{27}H_{25}N_5O$ requires: 435. found: 436.2 $[M+H]^+$.

Example 1 34

2'-(2-(3,5-bis(trifluoromethyl)phenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3,5-bis(trifluoromethyl)phenylboronic acid, purified by semi-preparative HPLC (method A) and isolated as a TFA-salt. ¹H NMR (400 MHz, DMSO-D6, 300K): δ=1.94 (2H, d, J=14.0 Hz), 2.31 (2H, dt, J1=14.0 Hz, J2=4.0 Hz), 3.13 (2H, q, J=11.9 Hz), 3.34 (2H, br d, J=11.9 Hz), 3.54 (2H, d, J=2.1 Hz), 7.45 (1H, m), 7.46 (1H, d, J=2.1 Hz), 7.97 (1H, d, J=5.4 Hz), 8.34 (1H, s), 8.46 (1H, m), 8.82 (1H, d, J=10.2 Hz), 8.89 (1H, d, J=5.4 Hz), 9.15 (1H, s), 12.00 (1H, s); MS (ES) $C_{23}H_{19}F_6N_5O$ requires: 495. found: 496.1 $[M+H]^+$.

Example 1 35

2'-(2-(3-(trifluoromethyl)phenyl)pyrimidin-4-yl)-5',6'-dihydrospiro[piperidine-4,7'-pyrrolo[3,2-c]pyridin]-4'(1'H)-one The title compound was prepared following the general procedure reported for Example 1_1 using 3-(trifluoromethyl)phenylboronic acid, purified by semi-preparative HPLC (Method A) and was isolated as TFA-salt. ¹H NMR (400 MHz, DMSO-D6, 300K): δ=1.92 (2H, d, J=14.5 Hz), 2.32 (2H, dt, J1=3.9 Hz, J2=14.5 Hz), 2.98 (1H, br s), 3.13 (2H, q, J=12.1 Hz), 3.33 (2H, d, J=12.1 Hz), 3.53 (1H, d, J=2.3 Hz), 7.43 (2H, s), 7.81 (1H, t, J=7.8 Hz), 7.89 (1H, d, J=5.5 Hz), 7.94 (1H, d, J=7.8 Hz), 8.40 (1H, br d, J=10.6 Hz), 8.76 (1H, br d, J=10.2 Hz), 8.85 (2H, d, J=5.0 Hz)—8.94 (1H, d, J=8.2 Hz), 11.88 (1H, s); MS (ES) $C_{22}H_{20}F_3N_5O$ requires: 427. found: 428.1 $[M+H]^+$.

Example 1 36

N-cyclohexyl-4-(4-(4'-oxo-1',4',5',6'-tetrahydrospiro[piperidine-4,7'-pyrrolo[3,2-c]pyridine]-2'-yl)pyrimidin-2-yl)benzamide The title compound was prepared following the general procedure reported for Example 1_1 using N-cyclohexyl-4-(4,4,5,5-tetramethyl-1,3,2-dioxaborolan-2-yl)benzamide, purified by semi-preparative HPLC (Method A) and was isolated as TFA-salt. MS (ES) $C_{28}H_{32}N_6O_2$ requires: 484. found: 485.1 $[M+H]^+$.

Example 2 1

Synthesis of 2'-(2-(benzofuran-2-yl)pyrimidin-4-yl)-1-methyl-5',6'-dihydrospiro[piperidine-4,7'-pyrrolo[3,2-c]pyridin]-4'(1'H)-one derivatives

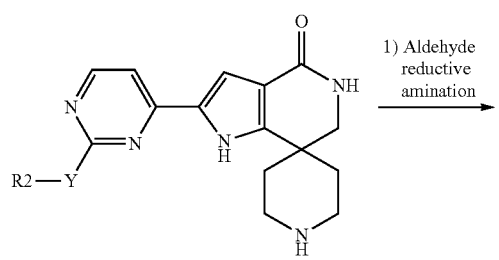

1) Aldehyde reductive amination →

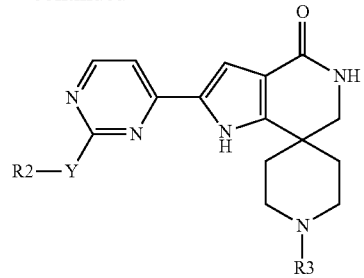

Example 2 1

2'-(2-(benzofuran-2-yl)pyrimidin-4-yl)-1-methyl-5',6'-dihydrospiro[piperidine-4,7'-pyrrolo[3,2-c]pyridin]-4'(1'H)-one Example 1_1 (76.9 mg, 0.193 mmol) was suspended in acetonitrile (6 mL). Formaldehyde (37%, 0.101 mL, 1.348 mmol), sodium cyanoborohydride (36.3 mg, 0.578 mmol) and some drops of acetic acid were added to the suspension and the mixture was stirred 15 h at room temperature. The reaction mixture was brought onto a SCX-column and was rinsed with MeOH. The product was washed off the column using 0.7M $NH_3$ in MeOH. After concentration of the product under vacuum the residue was purified by semi-preparative HPLC (Method A) and isolated as TFA-salt. ¹H NMR (400 MHz, DMSO-D6, 300K): δ=1.99 (2H, d, J=14.0 Hz), 2.45 (2H, dt, J1=3.3 Hz, J2=14.2 Hz), 2.87 (3H, d, J=4.4 Hz), 3.20 (2H, q, J=13.0 Hz), 3.46 92H, d, J=12.1 Hz), 3.57 (2H, d, J=2.3 Hz), 7.36 (1H, t, J=7.7 Hz), 7.41 (1H, s), 7.47 (1H, t, J=7.7 Hz), 7.54 (1H, br s), 7.74 (1H, d, J=8.2 Hz), 7.78 (1H, d, J=7.7 Hz), 7.83 (1H, d, J=5.6 Hz), 8.07 (1H, s), 8.80 (1H, d, J=5.6 Hz), 9.66 (1H, br s), 11.76 (1H, s); MS (ES) $C_{24}H_{23}N_5O_2$ requires: 413. found: 414.0 $[M+H]^+$.

The following example(s) were prepared according to this method:

Example 2 2

2'-(2-(benzofuran-2-yl)pyrimidin-4-yl)-1-ethyl-5',6'-dihydrospiro[piperidine-4,7'-pyrrolo[3,2-c]pyridin]-4(1'H)-one The title compound was prepared following the general procedure reported for Example 2_1 using acetaldehyde, purified by semi-preparative HPLC (Method A) and isolated as TFA-salt. ¹H NMR (400 MHz, DMSO-D6, 300K): δ=1.28 (3H, t, J=7.2 HZ), 1.83 (1H, d, J=14.5 Hz), 2.00 (2H, d, J=14.5 Hz), 3.13 (2H, q, J=12.9 Hz), 3.20 (2H, m), 3.39 (1H, m), 3.53 (2H, t, J=3.5 Hz), 3.57 (2H, s), 7.36 (1H, t, J=7.4 Hz), 7.42 (1H, d, J=2.3 Hz), 7.46 (1H, dt, J1=1.1 Hz, J2=7.4 Hz), 7.52 (1H, s), 7.75 (2H, t, J=9.4 Hz), 7.85 (1H, d, J=5.5 Hz), 8.14 (1H, s), 8.79 (1H, d, J=5.5 Hz), 9.61 (1H, br s), 11.68 (1H, s); MS (ES) $C_{25}H_{25}N_5O_2$ requires: 427. found: 428.0 $[M+H]^+$.

Example 2 3

1-(2-aminoethyl)-2'-(2-(benzofuran-2-yl)pyrimidin-4-yl)-5',6'-dihydrospiro[piperidine-4,7'-pyrrolo[3,2-c]pyridin]-4'(1'H)-one The title compound was prepared following the general procedure reported for Example 2_1, using (2-oxo-ethyl)- carbamicacid tert-butyl ester. The crude product was dissolved in a 1:1 mixture of DCM and TFA and stirred at room temperature for 1 h. The reaction mixture was concentrated under vacuum, purified by semi-preparative HPLC (Method A) and isolated as TFA-salt. $^1$H NMR (400 MHz, DMSO-D6, 300K): δ=2.02 (2H, br d, J=12.5 Hz), 2.59 (2H, br s), 2.73 (1H, s), 2.89 (1H, s), 3.37 (2H, br s), 3.59 (4H, br s), 7.36 (1H, t, J=7.4 Hz), 7.43 (1H, d, J=2.0 Hz), 7.46 (1H, t, J=7.4 Hz), 7.54 (1H, br s), 7.73 (2H, d, J=8.2 Hz), 7.83 (1H, d, J=5.5 Hz), 8.08 (3H, br s), 8.19 (1H, s), 8.79 (1H, d, J=5.5 Hz), 11.57 (1H, s); MS (ES) $C_{25}H_{26}N_6O_2$ requires: 442. found: 443.1 [M+H]$^+$.

Example 3_1

Synthesis of N-(2-(2'-(2-(benzofuran-2-yl)pyrimidin-4-yl)-4'-oxo-1',4',5',6'-tetrahydrospiro[piperidine-4,7'-pyrrolo[3,2-c]pyridine]-1-yl)ethyl)acetamide derivatives

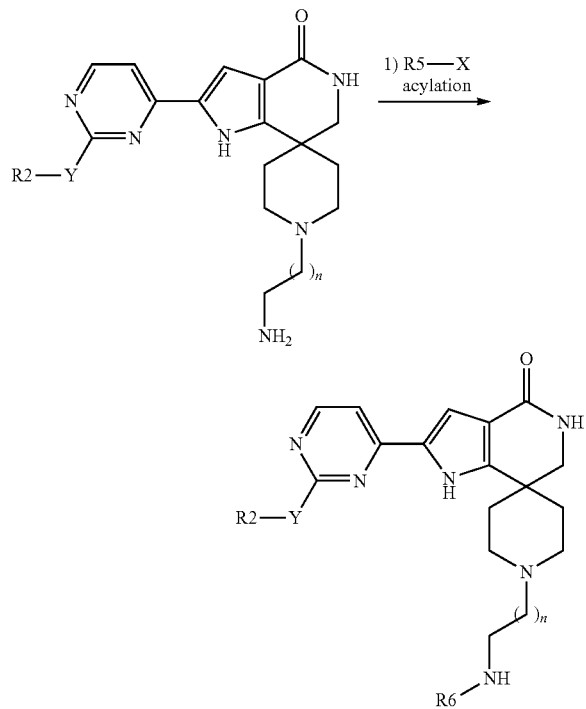

n = 1, 2

Example 3_1

N-(2-(2'-(2-(benzofuran-2-yl)pyrimidin-4-yl)-4'-oxo-1',4',5',6'-tetrahydrospiro[piperidine-4,7'-pyrrolo[3,2-c]pyridine]-1-yl)ethyl)acetamide Example 2_3 (19.5 mg, 0.025 mmol) was suspended in a DCM (2 mL). Acetyl chloride (2.6 μL, 0.037 mmol) and triethylamine (8.6 μL, 0.062 mmol) were added to the mixture and was stirred overnight at room temperature. The reaction was quenched with a few drops of water and concentrated in vacuo giving the crude product. The crude product was dissolved in MeOH and was brought onto a SCX-column followed by rinsing with MeOH. The product was washed off the column using 0.7 M NH$_3$ in MeOH. After concentration of the product under vacuum the residu was purified by semi-preparative HPLC (Method A) and isolated as TFA-salt. MS (ES) $C_{27}H_{28}N_6O_3$ requires: 484. found: 485.1 [M+H]$^+$.

The following example(s) were prepared according to this method:

Example 3_2

N-(3-(2'-(2-(benzofuran-2-yl)pyrimidin-4-yl)-4'-oxo-1',4',5',6'-tetrahydrospiro[piperidine-4,7'-pyrrolo[3,2-c]pyridine]-1-yl)propyl)acetamide Example 1_1 (85.5 mg, 0.136 mmol) was dissolved in a mixture of acetonitrile (5 mL) and water (2 mL). $K_2CO_3$ (37.7 mg, 0.273 mmol) and 3-(Boc-amino)propyl bromide 64.9 mg, 0.273 mmol) were added to the solution and was stirred overnight at 90° C. The reaction mixture was cooled to room temperature was brought onto a SCX-column followed by rinsing with MeOH. The product was washed off the column using 0.7 M NH$_3$ in MeOH. After concentration of the product under vacuum the residu was purified by semi-preparative HPLC (Method A) yielding 1-(3-aminopropyl)-2'-(2-(benzofuran-2-yl)pyrimidin-4-yl)-5',6'-dihydrospiro [piperidine-4,7'-pyrrolo[3,2-c]pyridin]-4'(1'H)-one as the TFA-salt. $^1$H NMR (400 MHz, DMSO-D6, 300K): δ=2.03 (4H, d, J=13.0), 2.62 (2H, dt, J1=3.1 Hz, J2=14.9 Hz), 2.94 (2H, m), 3.13-3.17 (4H, m), 3.53 (2H, d), 3.58 (2H, s), 7.36 (1H, t, J=7.0 Hz), 7.43 (1H, d, J=2.0 Hz), 7.46 (1H, t, J=9.4 Hz), 7.52 (1H, s), 7.73 (2H, d, J=8.6 Hz), 7.83 (1H, d, J=5.5 Hz), 7.91 (3H, br s), 8.20 (1H, s), 8.79 (1H, d, J=5.5 Hz), 10.10 (1H, br s), 11.62 (1H, s); MS (ES) $C_{26}H_{28}N_6O_2$ requires: 456. found: 457.3 [M+H]$^+$. The intermediate amine was acetylated following the general procedure reported for Example 3_1 using acetyl chloride. The crude product was purified by semi-preparative HPLC (Method A) and isolated as TFA-salt. $^1$H NMR (400 MHz, DMSO-D6, 300K): δ=1.86 (5H, m), 1.99 (2H, d, J=14.1 Hz), 3.05-3.22 (6H, m), 3.26-3.47 (2H, m), 3.51 (2H, m), 3.57 (2H, d, J=1.6 Hz), 7.36 (1H, t, J=7.8 Hz), 7.41 (1H, d, J=2.3 Hz), 7.47 (1H, dt, J1=1.1 Hz, J2=8.1 Hz), 7.52 (1H, br s), 7.74 (1H, d, J=7.4 Hz), 7.78 (1H, d, J=7.8 Hz), 7.85 (1H, d, J=5.5 Hz), 8.08 (1H, s), 8.12 (1H, t, J=5.9 Hz), 8.80 (1H, d, J=5.1 Hz)— 9.61 (1H, br s), 11.77 (1H; MS (ES) $C_{28}H_{30}N_6O_3$ requires: 498. found: 499.3 [M+H]$^+$.

Example 4_1

Synthesis of 2'-(2-(benzofuran-2-yl)-5-fluoropyrimidin-4-yl)-5',6'-dihydrospiro[piperidine-4,7'-pyrrolo[3,2-c]pyridin]-4'(1'H)-one derivatives (B3)

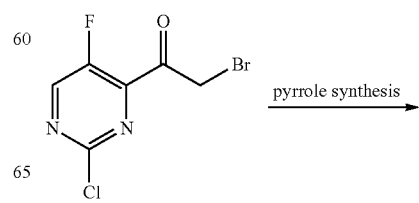

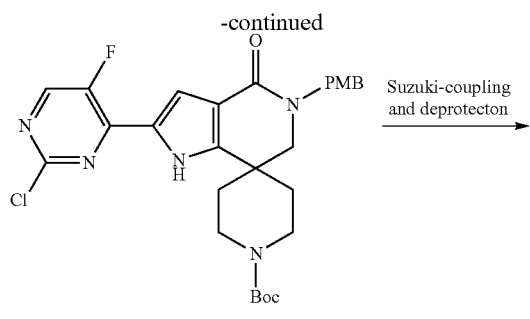

B1

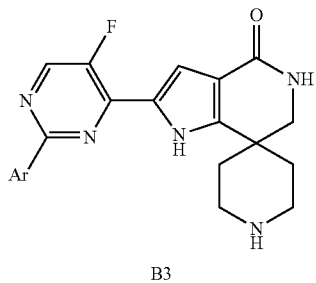

B3

Step 1: tert-butyl 2'-(2-chloro-5-fluoropyrimidin-4-yl)-5'-(4-methoxybenzyl)-4'-oxo-1',4',5',6'-tetrahydrospiro[piperidine-4,7'-pyrrolo[3,2-c]pyridine]-1-carboxylate (B1)

The title compound was prepared following the general procedure reported for Example 1_1 using 2-bromo-1-(2-chloro-5-fluoropyrimidin-4-yl)ethanone. Purification was effected by semi-preparative HPLC. (20-95%; acetonitrile, water, TFA; 60 min.). Fractions were collected, concentrated to a small volume and quenched with aq. NaHCO$_3$. The mixture was extracted twice with EtOAc. The organic layers were combined, dried over Na$_2$SO$_4$ and evaporated to dryness to give the title compound (200 mg, 23%). MS (ES) C$_{28}$H$_{31}$ClFN$_5$O$_4$ requires: 555. found: 556.3 [M+H]$^+$.

Example 4_1

2'-(2-(benzofuran-2-yl)-5-fluoropyrimidin-4-yl)-5',6'-dihydrospiro[piperidine-4,7'-pyrrolo[3,2-c]pyridin]-4'(1'H)-one The title compound was prepared following the general procedure reported in Example 1_1 step 6 and 7, using B1. The crude was purified by semi-preparative HPLC (method A) and isolated as a TFA-salt: 0 to 60% acetonitrile in water+TFA to yield (5 mg, 35%). MS (ES) C$_{23}$H$_{20}$FN$_5$O$_2$ requires: 417. found: 418.2 [M+H]$^+$.

The following example(s) were prepared according to the previous method:

Example 4_2

2'-(2-(benzo[d][1,3]dioxol-5-yl)-5-fluoropyrimidin-4-yl)-5',6'-dihydrospiro[piperidine-4,7'-pyrrolo[3,2-c]pyridin]-4'(1'H)-one The title compound was prepared following the general procedure reported in Example 4_1 using benzo[d][1,3]dioxol-5-ylboronic acid. The crude was purified by semi-preparative HPLC (method A) and isolated as a TFA-salt. MS (ES) C$_{22}$H$_{20}$FN$_5$O$_3$ requires: 421. found: 422.1 [M+H]$^+$.

Example 4_3

2'-(5-fluoro-2-(quinolin-3-yl)pyrimidin-4-yl)-5',6'-dihydrospiro[piperidine-4,7'-pyrrolo[3,2-c]pyridin]-4'(1'H)-one The title compound was prepared following the general procedure reported for Example 4_1 using quinolin-3-ylboronic acid, purified by semi-preparative HPLC (method A) and isolated as a TFA-salt. $^1$H NMR (400 MHz, DMSO-D6, 300K): δ=1.95 (2H, br d, J=14.2 Hz), 2.39 (4H, m), 2.50 (2H, m), 3.15 (2H, m), 3.34 (2H, br d, J=13.9 Hz), 3.57 (2H, s), 7.23 (1H, s), 7.54 (1H, s), 7.72 (1H, dd, J1=7.6 Hz, J2=15.0 Hz), 7.88 (1H, dd, J1=7.6 Hz, J2=15.4 Hz) 8.12 (2H, br d, J=8.5 Hz), 8.25 (1H, br s), 8.75 (1H, br s), 9.01 (1H, s), 9.45 (1H, s), 10.10 (1H, s, J=2.1 Hz), 12.01 (1H, s); MS (ES) C$_{24}$H$_{21}$FN$_6$O requires: 428. found: 429.2 [M+H]$^+$.

Example 4_4

4-(5-fluoro-4-(4'-oxo-1',4',5',6'-tetrahydrospiro[piperidine-4,7'-pyrrolo[3,2-c]pyridine]-2'-yl)pyrimidin-2-yl)-N-methylbenzamide The title compound was prepared following the general procedure reported for Example 4_1 using 4-(methylcarbamoyl)phenylboronic acid. The crude was purified by flash chromatrography on silica gel eluting with DCM:MeOH 100:0 to 80:20 followed by SCX-2 column eluted with MeOH:ammonia=100:0 to 99:1. $^1$H NMR (400 MHz, DMSO-D6, 300K): δ 1.63 (2H, br d, J=13.3 Hz), 2.25 (2H, dt, J1=13.3 Hz, J2=4.1 Hz), 2.73 (2H, t, J=12.0 Hz), 2.83 (3H, d, J=4.1 Hz), 2.91 (2H, br d, 12.0 Hz), 3.17 (1H, d, J=4.1 Hz), 3.47 (2H, d, J=2.1), 7.16 (1H, d, J=4.1 Hz), 7.31 (1H, s), 7.99 (2H, d, J=8.7 Hz), 8.58 (1H, q, J=5.0 Hz), 8.70 (2H, d, J=8.7 Hz), 8.88 (1H, d, 3.3 Hz), 11.90 (1H, s); MS (ES) C$_{23}$H$_{23}$FN$_6$O$_2$ requires: 434. found: 435.1 [M+H]$^+$.

Example 4_5

2'-(2-(4-chloro-2-fluorophenyl)-5-fluoropyrimidin-4-yl)-5',6'-dihydrospiro[piperidine-4,7'-pyrrolo[3,2-c]pyridin]-4'(1'H)-one The title compound was prepared following the general procedure reported in Example 4_1 using 4-chloro-2-fluorophenylboronic acid. The crude was purified by semi-preparative HPLC (method A) and isolated as a TFA-salt. $^1$H NMR (400 MHz, DMSO-D6, 300K): δ=1.89 (2H, br d, J=14.2 Hz), 2.32 (2H, m), 3.11 (2H, m), 3.30 (2H, m), 3.53 (2H, d, J=2.4 Hz), 7.17 (1H, s), 7.48 (2H, br m), 7.65 (1H, d, J=10.8 Hz), 8.21 (1H, br s), 8.27 (1H, dd, J1=8.5 Hz, J2=16.9 Hz), 8.74 (1H, br s), 8.95 (1H, s), 11.86 (1H, s); MS (ES) C$_{21}$H$_{18}$ClF$_2$N$_5$O requires: 429. found: 430.2 [M+H]$^+$.

Example 5_1

Synthesis of 2'-(2-(benzofuran-2-yl)pyrimidin-4-yl)-5',6'-dihydrospiro[piperidine-3,7'-pyrrolo[3,2-c]pyridin]-4'(1'H)-one derivatives (C8)

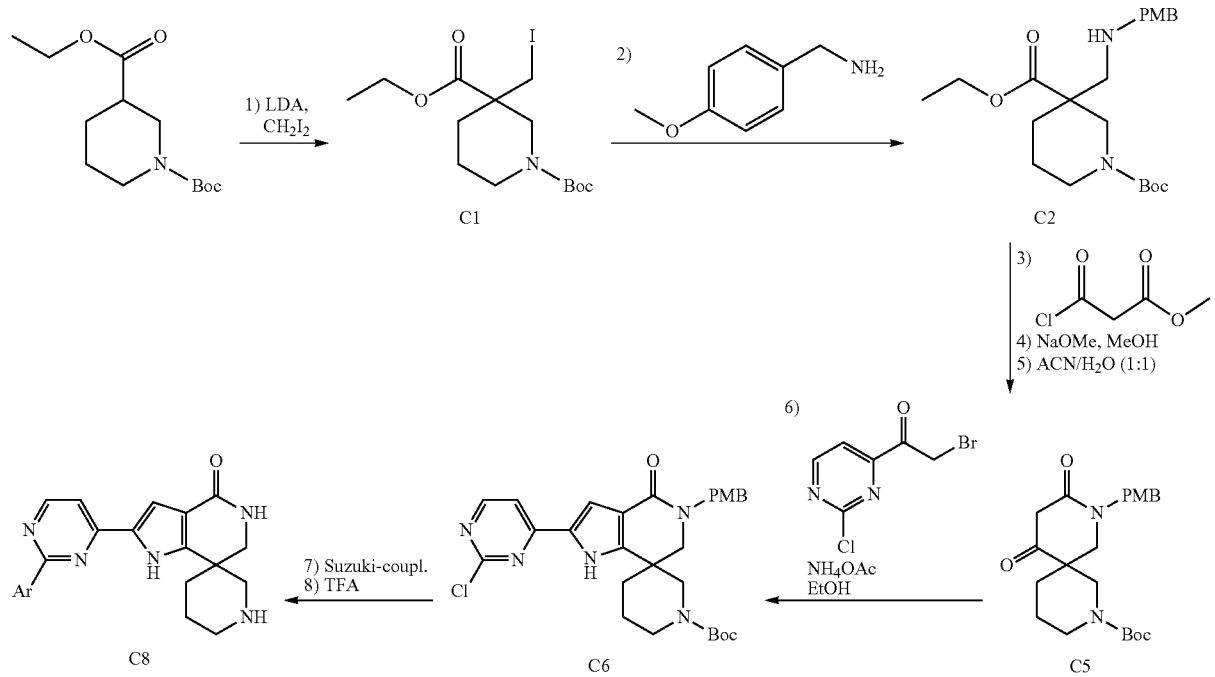

Step 1: 1-tert-butyl 3-ethyl 3-(iodomethyl)piperidine-1,3-dicarboxylate (C1)

A solution of diisopropylamine (14.6 mmol, 2.05 mL) in THF (15 mL) was cooled to −78° C. N-butyllithium (1.6 M in hexane) (16 mmol, 10 ml) was added dropwise and the solution was stirred for 30 minutes at 0° C. After cooling to −78° C. a solution of 1-tert-butyl 3-ethyl piperidine-1,3-dicarboxylate (14.6 mmol, 3.75 g) in 20 ml THF was added and the solution was stirred for 3 h at −78° C. A solution of diiodomethane (16 mmol, 1.3 mL) in THF (10 mL) was added and the solution was stirred for 2 days at room temperature. The reaction was quenched by the addition of water and extracted twice with EtOAc. The organic layers were washed with brine, dried over $MgSO_4$, filtered and concentrated in vacuo. The crude was purified by flash chromatography (heptane/EtOAc: 10 to 50%) yielding the title compound (C1) (4.5 g, 74%). MS (ES) $C_{14}H_{24}INO_4$ requires: 397. found: 420.1 $[M+Na]^+$.

Step 2: 1-tert-butyl 3-ethyl 3-((4-methoxybenzylamino)methyl)piperidine-1,3-dicarboxylate (C2)

1-tert-butyl 3-ethyl 3-(iodomethyl)piperidine-1,3-dicarboxylate (C1) (4.13 mmol, 1.64 g) was dissolved in THF (5 mL), (4-methoxyphenyl)methanamine (6.19 mmol, 0.81 mL) and cesium carbonate (6.19 mmol, 2.02 g) were added and the mixture was heated for 8 h at 145° C. in the microwave. The mixture was filtered over a PE-filter and concentrated in vacuo. The crude was purified by flash chromatography (heptane/EtOAc: 0 to 45%) yielding the title compound (C2) (340 mg, 20%). $^1$H NMR (400 MHz, DMSO, 300K): δ=1.23 (3H, t, J=7.2 Hz), 1.43 (9H, s), 1.55 (2H, m), 1.67 (1H, m), 1.89 (1H, m), 2.64 (1H, d, J=11.9 Hz), 2.77 (1H, d, J=11.9 Hz), 3.21 (1H, m), 3.51 (2H, m), 3.62 (1H, m), 3.70 (2H, m), 3.79 (3H, s), 4.14 (2H, q, J=7.2 Hz), 6.84 (2H, d, J=8.6 Hz), 7.20 (2H, d, J=8.6 Hz).

Step 3: 1-tert-butyl 3-ethyl 34(3-methoxy-N-(4-methoxybenzyl)-3-oxopropanamido)methyl)piperidine-1,3-dicarboxylate (C3)

The title compound was prepared following the general procedure reported for Example 1_1, step 2 using tert-butyl 8-(4-methoxybenzyl)-9-oxo-2,8-diazaspiro[5.5]undecane-2-carboxylate (C2). The crude was purified by flash column chromatography (heptane:EtOAc (1:1) yielding the title compound (C3) (1.7 g, 100%). MS (ES) $C_{26}H_{38}N_2O_8$ requires: 506. found: 507.3 $[M+H]^+$.

Step 4: 2-tert-butyl 10-methyl 8-(4-methoxybenzyl)-9,11-dioxo-2,8-diazaspiro[5.5]undecane-2,10-dicarboxylate (C4)

The title compound was prepared following the general procedure reported for Example 1_1, step 3 using 1-tert-butyl 3-ethyl 3-((3-methoxy-N-(4-methoxybenzyl)-3-oxopropanamido)methyl)piperidine-1,3-dicarboxylate (C3). The crude product (C4) was used as is in the next reaction. MS (ES) $C_{24}H_{32}N_2O_7$ requires: 460. found: 483.3 $[M+Na]^+$.

Step 5: tert-butyl 8-(4-methoxybenzyl)-9,11-dioxo-2,8-diazaspiro[5.5]undecane-2-carboxylate (C5)

The title compound was prepared following the general procedure reported for Example 1_1, step 4 using 2-tert-butyl 10-methyl 8-(4-methoxybenzyl)-9,11-dioxo-2,8-diazaspiro[5.5]undecane-2,10-dicarboxylate (C4). The crude was purified by flashchromatography (heptane/EtOAc: 20 to 60%) yielding C5. MS (ES) $C_{22}H_{30}N_2O_5$ requires: 402. found: 425.2 $[M+Na]^+$.

Step 6: tert-butyl 2'-(2-chloropyrimidin-4-yl)-5'-(4-methoxybenzyl)-4'-oxo-1',4',5',6'-tetrahydrospiro[piperidine-3,7'-pyrrolo[3,2-c]pyridine]-1-carboxylate (C6)

The title compound was prepared following the general procedure reported for Example 1_1, step 5 using tert-butyl 8-(4-methoxybenzyl)-9,11-dioxo-2,8-diazaspiro[5.5]undecane-2-carboxylate (C5). The crude was purified by flash column chromatography (heptane:EtOAc=100:0 to 0:100) yielding the title compound (C6) (403 mg, 60%). MS (ES) $C_{28}H_{32}ClN_5O_4$ requires: 537. found: 538.1 [M+H]$^+$.

Example 5_1

2'-(2-(benzofuran-2-yl)pyrimidin-4-yl)-5',6'-dihydrospiro[piperidine-3,7'-pyrrolo[3,2-c]pyridin]-4'(1'H)-one The title compound was prepared following the general procedure reported for the preparation of Example 1_1 step 6 and 7, using C6. The crude was purified by semi-preparative HPLC (method A) and isolated as a TFA-salt. $^1$H NMR (400 MHz, DMSO-D6, 300K): δ 1.74 (1H, m), 1.89 (2H, br d, J=12.8 Hz), 2.28 (1H, m), 2.84 (br q, J=11.6 Hz), 3.37 (2H, m), 3.48 (2H, m), 3.63 (1H, dd, J1=12.8 Hz, J2=2.9 Hz), 7.36 (1H, t, J=7.9 Hz), 7.43 (1H, d, J=2.1 Hz), 7.47 (2H, m), 7.74 (1H, d, 8.3 Hz), 7.84 (2H, m), 7.97 (1H, s), 8.52 (1H, m), 8.81 (1H, d, J=5.0 Hz), 9.14 (1H, br d, 10.9 Hz), 11.9 (1H, s); MS (ES) $C_{23}H_{21}N_5O_2$ requires: 399. found: 400.2 [M+H]$^+$.

The following example(s) were prepared according to the previous method:

Example 5_2

2'-(2-(benzo[d][1,3]dioxol-5-yl)pyrimidin-4-yl)-5',6'-dihydrospiro[piperidine-3,7'-pyrrolo[3,2-c]pyridin]-4'(1'H)-one The title compound was prepared following the general procedure reported for the preparation of Example 5_1 using benzo[d][1,3]dioxol-5-ylboronic acid. The crude was purified by semi-preparative HPLC (method A) and isolated as a TFA-salt. MS (ES) $C_{22}H_{21}N_5O_3$ requires: 403. found: 404.2 [M+H]$^+$.

Example 6_1

Synthesis of 2'-(2-(quinolin-3-yl)pyrimidin-4-yl)-5',6'-dihydrospiro[pyrrolidine-3,7'-pyrrolo[3,2-c]pyridin]-4'(1'H)-one derivatives (D9)

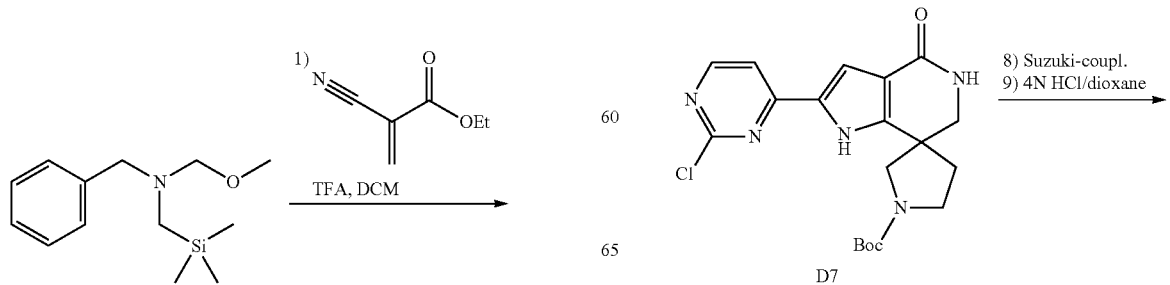

-continued

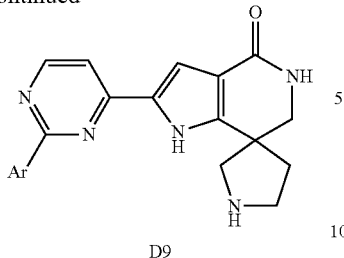

D9

Step 1: ethyl 1-benzyl-3-cyanopyrrolidine-3-carboxylate (D1)

TFA (4.31 mmol, 0.49 g) was added to a solution of ethyl 2-cyanoacrylate (17.58 mmol, 2.20 g) in DCM (100 mL) under nitrogen atmosphere. Subsequently, a solution of N-benzyl-1-methoxy-N-((trimethylsilyl)methyl)methanamine (21.49 mmol, 5.10 g) in DCM (50 mL) was added dropwise while cooling with an ice-bath in order to keep the reaction temperature at room temperature (exothermic reaction). The reaction mixture was stirred overnight at room temperature. Then the mixture was washed with saturated aqueous NaHCO$_3$ (100 mL). The aqueous phase was extracted with DCM (100 mL). The combined organic phase was dried over MgSO$_4$ and evaporated in vacuo. The crude product was purified by flash silicagel chromatography (100% heptane to 50% EtOAc) yielding 4.27 g of a colorless oil (94%). $^1$H-NMR (400 MHz, CDCl$_3$, 300K): δ=1.32 (3H, t, J=7.1 Hz), 2.44 (1H, m), 2.59 (1H, m), 2.69 (1H, m), 2.89 (1H, m), 2.99 (1H, d, J=9.8 Hz), 3.17 (1H, d, J=9.8 Hz), 3.69 (2H, s), 4.27 (2H, q, J=7.1 Hz), 7.29 (5H, m).

Step 2: methyl 3-(aminomethyl)-1-benzylpyrrolidine-3-carboxylate (D2)

50% Raney Nickel in water (5.84 mmol, 1.00 g) was suspended in MeOH and decanted. This procedure was done a second time. Eventually, the Raney Nickel was added as a suspension in MeOH (5 mL) to a solution of D1 (2.05 mmol, 0.53 g) in MeOH (10 mL). The reaction mixture was shaken in the Parr Apparatus (3.2 bar H$_2$) for 2 hours at room temperature. The Raney Nickel was filtered off. The filtrate was concentrated and co-evaporated with dioxane to give 0.48 g of a colorless oil which was a mixture of the desired product and its corresponding ethyl ester analogue according to $^1$H-NMR.

Step 3: methyl 1-benzyl-3-(3-ethoxy-3-oxopropanamido)methyl)pyrrolidine-3-carboxylate (D3)

A solution of D2 (22.15 mmol, 5.50 g) and triethylamine (71.80 mmol, 7.26 g) in DCM (60 mL) was cooled to 0° C. Then, a solution of ethyl 3-chloro-3-oxopropanoate (32.60 mmol, 4.91 g) in DCM (40 mL) was added dropwise. The mixture was allowed to reach room temperature for 21 hours. Extra triethylamine (22.15 mmol, 2.24 g) and ethyl 3-chloro-3-oxopropanoate (11.08 mmol, 1.67 g) were added at 0° C. and the mixture was allowed to reach room temperature for another 60 minutes in order to drive the reaction to completion. The reaction mixture was washed with water (80 mL). The aqueous phase was extracted with DCM (65 mL). The combined organic phase was washed with brine (80 mL), dried over MgSO$_4$ and evaporated in vacuo. The crude product was purified by flash silicagel chromatography (100% DCM to 10% MeOH) yielding 9.58 g of a yellow oil which was a mixture of the desired product and its corresponding diethyl ester analogue according to $^1$H-NMR.

Step 4: 1-tert-butyl 3-methyl 3-((3-ethoxy-3-oxopropanamido)methyl)pyrrolidine-1,3-dicarboxylate (D4)

D3 (14.43 mmol, 5.23 g) and di-tert-butyl dicarbonate (17.32 mmol, 3.78 g) were dissolved in EtOAc (180 mL). Then 10% palladium on activated carbon (0.909 mmol, 1.077 g) was added and hydrogenation was performed by bubbling H$_2$—gas through the mixture at room temperature for 21 hours. The mixture was filtered and evaporated in vacuo. The crude product was purified by flash silicagel chromatography (heptane/EtOAc=9/1 to 100% EtOAc) yielding 3.02 g as a yellow oil which was a mixture of the desired product and its corresponding diethyl ester analogue according to $^1$H-NMR. MS (ES) C$_{17}$H$_{28}$N$_2$O$_7$ requires: 372. found: 373.4 [M+H]$^+$.

Step 5: 2-tert-butyl 9-methyl 8,10-dioxo-2,7-diazaspiro[4.5]decane-2,9-dicarboxylate (D5)

A fresh solution of sodium methoxide was prepared using sodium (31.60 mmol, 0.73 g) and MeOH (8.45 mL). A solution of D4 (4.10 mmol, 1.53 g) in MeOH (4.48 mL) was added dropwise. The reaction mixture was stirred overnight at 65° C. Then the mixture was cooled to room temperature. THF was added and the mixture was brought to pH 7 with 3% aqueous citric acid. Subsequently, the aqueous phase was saturated with NaCl. After separation of the two layers the aqueous phase was extracted with THF for a second time. The combined organic phase was dried over MgSO$_4$ and evaporated in vacuo. The crude product was purified by flash silicagel chromatography (100% DCM to 10% MeOH) to give 0.62 g of a yellow oil (46%). MS (ES) C$_{15}$H$_{22}$N$_2$O$_6$ requires: 326. found: 327.3 [M+H]$^+$.

Step 6: tert-butyl 8,10-dioxo-2,7-diazaspiro[4.5]decane-2-carboxylate (D6)

A solution of D5 (1.90 mmol, 0.62 g) in 40 mL acetonitrile/water (1/1) was refluxed for 5 hours. The reaction mixture was evaporated in vacuo. The crude product was purified by flash silicagel chromatography (DCM/MeOH=95/5) yielding 0.34 g of a yellow oil (66%). $^1$H-NMR (400 MHz, CDCl$_3$, 300K): δ=1.46 (9H, s), 1.88 (1H, m), 2.26 (1H, m), 3.50 (8H, m), 6.70 (1H, br d, 34.8 Hz); MS (ES) C$_{13}$H$_{20}$N$_2$O$_4$ requires: 268. found: 269.4 [M+H]$^+$.

Step 7: tert-butyl 2'-(2-chloropyrimidin-4-yl)-4'-oxo-1',4',5',6'-tetrahydrospiro[pyrrolidine-3,7'-pyrrolo[3,2-c]pyridine]-1-carboxylate (D7)

A solution of 2-bromo-1-(2-chloropyrimidin-4-yl)ethanone (1.04 mmol, 0.24 g), D6 (1.04 mmol, 0.28 g) and ammonium acetate (4.15 mmol, 0.32 g) in EtOH (20 mL) was stirred at room temperature for 1 hour. The reaction mixture was concentrated. The residue was taken up in water (20 mL) and brought to pH 7 with 5% aqueous NaHCO$_3$. The precipitate was filtered off and purified by flash silicagel chromatography (100% DCM to 10% MeOH) yielding 0.11 g of a yellow solid (26%). $^1$H-NMR (400 MHz, CDCl$_3$, 300K): δ=1.49 (9H, s), 2.28 (2H, m), 3.55 (6H, m), 5.70 (1H, br s), 7.30 (1H, s), 7.39 (1H, d, J=5.3 Hz), 8.50 (1H, d, J=5.3 Hz), 9.84 (1H, br s); MS (ES) C$_{19}$H$_{22}$ClN$_5$O$_3$ requires: 403. found: 404.2 [M+H]$^+$.

Step 8 and 9: Example 6_1: 2'-(2-(quinolin-3-yl)pyrimidin-4-yl)-5',6'-dihydrospiro[pyrrolidine-3,7'-pyrrolo[3,2-c]pyridin]-4'(1'H)-one A mixture of quinolin-3-ylboronic acid (53.2 µmol, 9.2 mg), D7 (53.2 µmol, 21.5 mg), 2 N aqueous $K_2CO_3$ (106 µL), toluene (837 µL) and EtOH (209 µL) was purged with nitrogen. Then tetrakis(triphenylphosphine)palladium(0) (2.7 µmol; 3.1 mg) was added. The reaction mixture was stirred for 15 minutes at 140° C. in the microwave. The mixture was washed with water (1 mL). Brine (1 mL) was added to the aqueous phase, followed by an extraction with EtOAc (2×2 mL). The combined organic phase was concentrated. The residue was treated with 4N HCl in dioxane (2 mL) at room temperature for 30 minutes. The mixture was centrifuged and decanted. Subsequently, the residue was suspended in diethyl ether, centrifuged and decanted for another 2 times. The residue was dried in vacuo and purified by semi-preparative HPLC (method A), which obtained 10.1 mg of the desired product as a TFA salt (37%). $^1$H NMR (400 MHz, DMSO-D6, 300K): δ=2.21 (1H, m), 2.55 (1H, m), 3.50 (6H, m), 7.50 (1H, d, J=2.2 Hz), 7.56 (1H, br s), 7.73 (1H, m), 7.90 (1H, m), 7.91 (1H, d, J=5.4 Hz); 8.14 (1H, br d, J=8.6 Hz), 8.23 (1H, br d, J=8.2 Hz), 8.90 (1H, d, J=5.4 Hz), 9.10 (1H, br s), 9.25 (1H, br s), 9.49 (1H, d, J=2.1 Hz), 10.08 (1H, d, 2.1 Hz), 12.02 (1H, br s); MS (ES) $C_{23}H_{20}N_6O$ requires: 396. found: 397.3 $[M+H]^+$.

The following examples were prepared according to the previous method:

Example 6_2

2'-(2-(benzo[d][1,3]dioxol-5-yl)pyrimidin-4-yl)-5',6'-dihydrospiro[pyrrolidine-3,7'-pyrrolo[3,2-c]pyridin]-4'(1'H)-one The title compound was prepared following the general procedure reported for Example 6_1 using benzo[d][1,3]dioxol-5-ylboronic acid and was purified by semi-preparative HPLC (method A). The product was obtained as a TFA salt. MS (ES) $C_{21}H_{19}N_5O_3$ requires: 389. found: 390.3 $[M+H]^+$.

Example 6_3

2'-(2-p-tolylpyrimidin-4-yl)-5',6'-dihydrospiro[pyrrolidine-3,7'-pyrrolo[3,2-c]pyridin]-4'(1'H)-one The title compound was prepared following the general procedure reported for Example 6_1 using p-tolylboronic acid and was purified by semi-preparative HPLC (method A). The product was obtained as a TFA salt. MS (ES) $C_{21}H_{21}N_5O$ requires: 359. found: 360.3 $[M+H]^+$.

Example 6_4

2'-(2-(3-fluorophenyl)pyrimidin-4-yl)-5',6'-dihydrospiro[pyrrolidine-3,7'-pyrrolo[3,2-c]pyridin]-4'(1'H)-one The title compound was prepared following the general procedure reported for Example 6_1 using 3-fluorophenylboronic acid and was purified by semi-preparative HPLC (method A). The product was obtained as a TFA salt. MS (ES) $C_{20}H_{18}FN_5O$ requires: 363. found: 364.3 $[M+H]^+$.

Example 6_5

2'-(2-(benzofuran-2-yl)pyridin-4-yl)-5',6'-dihydrospiro[pyrrolidine-3,7'-pyrrolo[3,2-c]pyridin]-4'(1'H)-one The title compound was prepared following the general procedure reported for the preparation of Example 6_1 using benzofuran-2-ylboronic acid, except that in step 7 2-bromo-1-(2-chloropyridin-4-yl)ethanone was used. The crude material was purified by semi-preparative HPLC (method A) and isolated as a TFA-salt. MS (ES) $C_{23}H_{20}N_4O_2$ requires: 384. found: 385.3 $[M+H]^+$.

Example 7_1

Synthesis of 2'-(2-(benzofuran-2-yl)pyrimidin-4-yl)-5',6'-dihydrospiro[morpholine-2,7'-pyrrolo[3,2-c]pyridin]-4'(1'H)-one derivatives (E10)

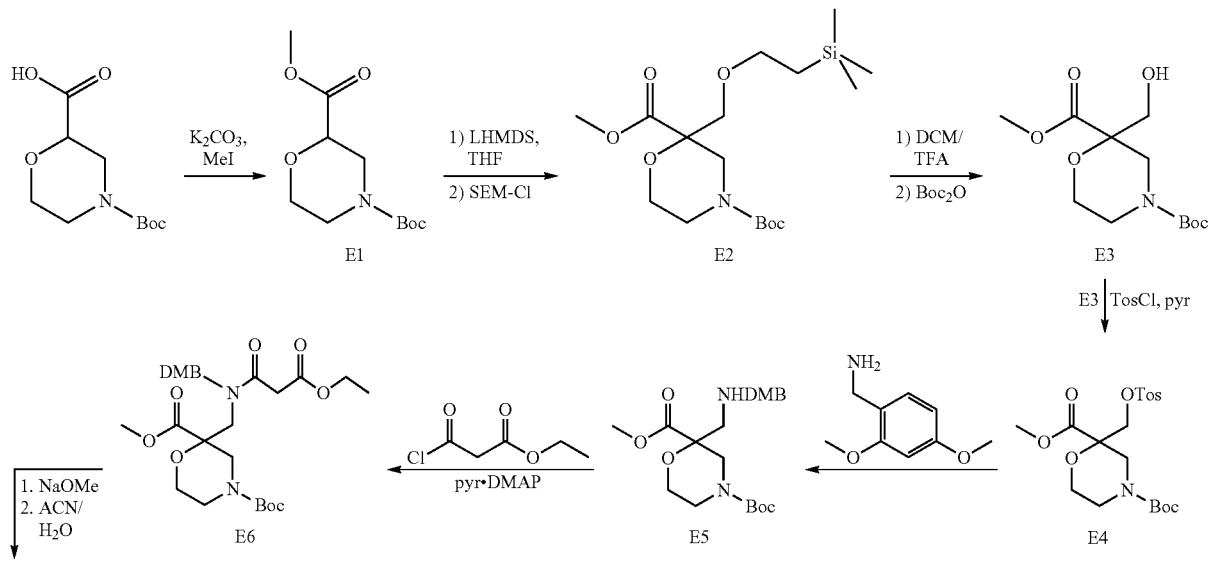

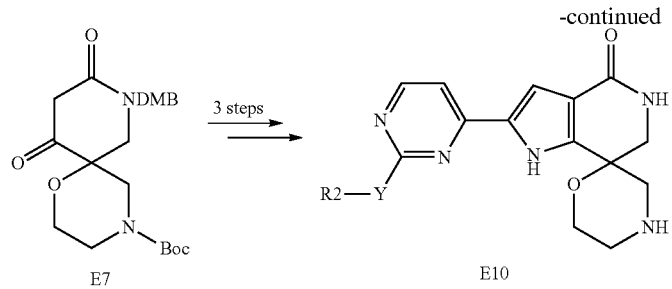

Step 1: 4-tert-butyl 2-methyl morpholine-2,4-dicarboxylate (E1)

4-Tert-butyl 2-methyl morpholine-2,4-dicarboxylate (5 g, 21.62 mmol) was dissolved in DMF (60 mL), K$_2$CO$_3$ (9.10 g, 64.9 mmol) and iodomethane (4.98 mL, 80 mmol) were added and the suspension was stirred for 15 h at 60° C. The reaction mixture was cooled to room temperature, poured into saturated NH$_4$Cl and extracted with EtOAc. The organic layer was washed with saturated NH$_4$Cl and brine, dried over MgSO$_4$, filtered and concentrated in vacuo. The residue was purified through a short column of silica (heptane:EtOAc 100:0 to 50:50) to yield 4-tert-butyl 2-methyl morpholine-2,4-dicarboxylate (5.09 g, 96%) as a white solid. MS (ES) C$_{11}$H$_{19}$NO$_5$ requires: 245. found: 268.2 [M+Na]$^+$.

Step 2: 4-tert-butyl 2-methyl 2-(2-(trimethylsilyl)ethoxy)methyl)morpholine-2,4-dicarboxylate (E2)

E1 (5.0 g 20.39 mmol) was dissolved in THF (45 mL) and cooled to −78° C. LHMDS (1 M in hexane/ethylbenzene) (40.8 mL, 40.8 mmol) was added in 30 minutes and the solution was stirred for 35 min at −78° C. (2-(Chloromethoxy)ethyl)trimethylsilane (10.02 mL, 56.5 mmol) was added and the reaction mixture was allowed to warm to room temperature overnight. The reaction mixture was quenched with saturated NH$_4$Cl and extracted twice with EtOAc. The organic layer was washed with brine, dried over MgSO$_4$, filtered and concentrated in vacuo. The residue was purified by flash column chromatography (heptane:EtOAc=100:0 to 70:30) yielding the title compound (6.09 g, 80%). $^1$H NMR (400 MHz, CDCl$_3$, 300K): δ 0.00 (3H, s), 0.92 (2H, t, J=7.5 Hz), 1.47 (9H, s), 3.02 (2H, d, J=13.3 Hz), 3.55 (4H, m), 3.78 (3H, s), 3.83 (3H, m), 4.34 (1H, d, J=13.3 Hz). MS (ES) C$_{17}$H$_{33}$NO$_6$Si requires: 375. found: 398.2 [M+Na]$^+$.

Step 3: 4-tert-butyl 2-methyl 2-(hydroxymethyl)morpholine-2,4-dicarboxylate (E3)

E2 (6.09 g, 16.22 mmol) was dissolved in DCM (100 mL), TFA (26.5 mL, 357 mmol) was added and the solution was stirred for 3 days at RT. The reaction mixture was concentrated and the residue was dissolved in DCM (100 mL). N-ethyl-N-isopropylpropan-2-amine (15 mL, 86 mmol) and di-tert-butyl dicarbonate (10.62 g, 48.7 mmol,) were added and the solution was stirred for 2 h at RT. Water was added and the mixture was extracted twice with DCM. The organic layer was washed with brine, dried over MgSO$_4$, filtered and concentrated in vacuo. The residue was purified by flash column chromatography from toluene:acetone 100:0 to 50:50 which gave the title compound (3.22 g, 72%). $^1$H NMR (400 MHz, CDCl$_3$, 300K): δ 1.46 (9H, s), 2.24 (1H, m), 3.05 (2H, m), 3.64-4.14 (7H, m), 4.32 (1H, d, J=13.7 Hz); MS (ES) C$_{12}$H$_{21}$NO$_6$ requires: 275. found: 298.2 [M+Na]$^+$.

Step 4: 4-tert-butyl 2-methyl 2-(tosyloxymethyl)morpholine-2,4-dicarboxylate (E4)

E3 (3.2 g, 11.62 mmol) was dissolved in pyridine (75 mL), p-toluenesulfonyl chloride (2.66 g, 13.95 mmol) was added in 4 portions in ca. 10 minutes and the solution was stirred for 15 h at RT. The reaction mixture was poured into water and extracted twice with EtOAc. The organic layer was washed with 1 N HCl and brine, dried over MgSO$_4$, filtered and concentrated in vacuo. The crude was purified by flash column chromatography (heptane:EtOAc 100:0 to 40:60) yielding the title compound (4.0 g, 80%). MS (ES) C$_{19}$H$_{27}$NO$_8$S requires: 429. found: 452.1 [M+Na]$^+$.

Step 5: 4-tert-butyl 2-methyl 2-((2,4-dimethoxybenzylamino)methyl)morpholine-2,4-dicarboxylate (E5)

E4 (365 mg, 0.850 mmol) was dissolved in acetonitrile (10 mL), (2,4-dimethoxyphenyl)methanamine (700 μL, 4.66 mmol) was added and the solution was stirred for 15 h at reflux temperature. The reaction mixture was concentrated in vacuo, extracted with water/EtOAc and washed twice with water. The organic layer was washed with brine, dried over MgSO$_4$, filtered and concentrated in vacuo. The residue was purified by flash column chromatography from toluene:EtOAc 100:0 to 20:80 which gave the title compound (115 mg, 32%). MS (ES) C$_{21}$H$_{32}$N$_2$O$_7$ requires: 424. found: 425.2 [M+H]$^+$.

Step 6: 4-tert-butyl 2-methyl 2-((N-(2,4-dimethoxybenzyl)-3-ethoxy-3-oxopropanamido)methyl)morpholine-2,4-dicarboxylate (E6)

The title compound was prepared following the general procedure for the preparation of Example 1__1 Step 2, using E5. The crude was purified by flash column chromatography (toluene:EtOAc 100:0 to 50:50) yielding the title compound (1.72 g, 92%). MS (ES) C$_{26}$H$_{38}$N$_2$O$_{10}$ requires: 538. found: 561.3 [M+Na]$^+$.

Step 7: tert-butyl 8-(2,4-dimethoxybenzyl)-9,11-dioxo-1-oxa-4,8-diazaspiro[5.5]undecane-4-carboxylate (E7)

The title compound was prepared following the general procedure reported for the preparation of Example 1__1 Step 3 and 4, using E6. The crude was purified by flash column chromatography (toluene:EtOAc 100:0 to 0:100) yielding the title compound (772 mg, 66%). $^1$H NMR (400 MHz, CDCl$_3$, 300K): δ1.46 (9H, s), 3.04-3.36 (4H, m), 3.41-3.67 (4H, m), 3.80 (3H, m), 3.81 (3H, s), 4.62 (1H, m), 6.46 (2H, m), 7.22 (1H, d, J=8.8 Hz). $^{13}$C NMR (100 MHz, CDCl$_3$, 300K): δ

28.71, 44.85, 45.75, 46.34, 50.42, 55.80, 62.97, 81.10, 98.92, 104.9, 116.9, 131.8, 157.0, 159.0, 161.1, 165.9, 201.9. MS (ES) $C_{22}H_{30}N_2O_7$ requires: 434. found: 435.1 $[M+H]^+$. Accurate mass $[M+H]^+$=435.2116.

Step 8: tert-butyl 2'-(2-chloropyrimidin-4-yl)-5'-(4-methoxybenzyl)-4'-oxo-1',4',5',6'-tetrahydrospiro[morpholine-2,7'-pyrrolo[3,2-c]pyridine]-4-carboxylate (E8)

The title compound was prepared following the general procedure reported for the preparation of Example 1_1 Step 5, using E7. The crude was purified by flash column chromatography (toluene:EtOAc 100:0 to 20:80) yielding the title compound (160 mg, 16%). MS (ES) $C_{28}H_{32}ClN_5O_5$ requires: 569. found: 570.2 $[M+H]^+$.

Example 7_1

2'-(2-(benzofuran-2-yl)pyrimidin-4-yl)-5',6'-dihydrospiro[morpholine-2,7'-pyrrolo[3,2-c]pyridin]-4'(1'H)-one The title compound was prepared following the general procedure reported for Example 1_1 using E8 and 2-benzofuraneboronic acid. The crude was purified by semi-preparative HPLC (method A) and isolated as a TFA-salt. MS (ES) $C_{22}H_{19}N_5O_3$ requires: 401. found: 402.1 $[M+H]^+$.

Example 8_1

Synthesis of 2'-(2-(benzofuran-2-yl)pyridin-4-yl)-5',6'-dihydrospiro[piperidine-4,7'-pyrrolo[3,2-c]pyridin]-4'(1'H)-one derivatives (F3)

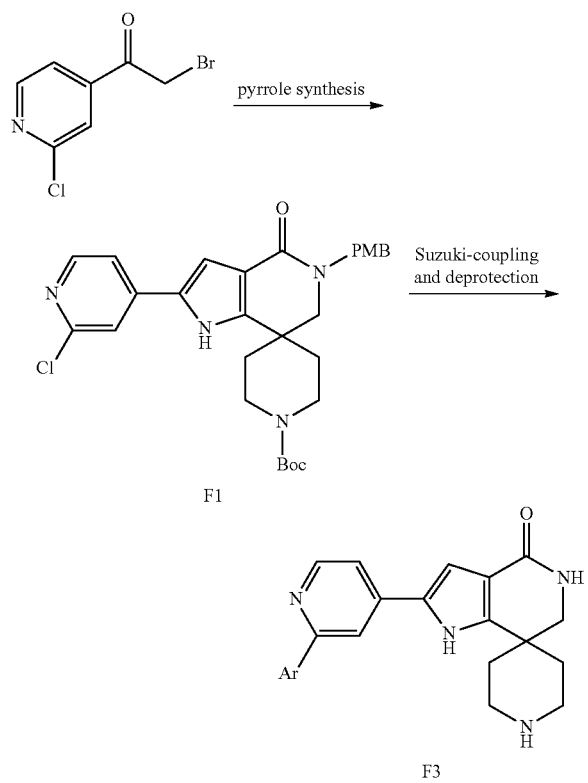

Step 1: tert-butyl 2'-(2-chloropyridin-4-yl)-5'-(4-methoxybenzyl)-4'-oxo-1',4',5',6'-tetrahydrospiro[piperidine-4,7'-pyrrolo[3,2-c]pyridine]-1-carboxylate (F1)

The title compound was prepared following the general procedure reported for the preparation of Example 1_1 step 5, using 2-bromo-1-(2-chloropyridin-4-yl)ethanone. The crude was purified by flash column chromatography (heptane:EtOAc=90:10 to 0:100) yielding the title compound (2.08 g, 52%). A small sample was purified further by semi-preparative HPLC (method A). The desired fractions were taken up in saturated NaHCO₃ and extracted with EtOAc to yield an analytical sample. $^1$H NMR (400 MHz, DMSO-D6, 300K): δ 1.40 (9H, s), 1.52 (2H, br d, J=13.7 Hz), 1.89 (2H, m), 2.62 (2H, br s), 3.52 (2H, s), 3.74 (3H, s), 3.78 (2H, br s), 4.54 (2H, s), 6.91 (2H, d, J=8.7 Hz), 7.21 (1H, d, J=2.1 Hz), 7.29 (2H, d, 8.7 Hz), 7.73 (1H, dd, J1=5.4, J2=1.2 Hz), 7.87 (1H, s), 8.30 (1H, d, J=5.4 Hz), 11.57 (1H, s). $^{13}$C NMR (100 MHz, DMSO-D6, 300K): ∂ 28.47, 31.73, 34.38, 48.13, 51.42, 55.45, 60.11, 79.17, 108.9, 114.2, 115.4, 117.6, 117.8, 128.5, 130.0, 130.5, 142.5, 146.1, 150.3, 151.5, 154.0, 158.8, 162.8. MS (ES) $C_{29}H_{33}ClN_4O_4$ requires: 536. found: 537.1 $[M+H]^+$.

Example 8_1

2'-(2-(benzofuran-2-yl)pyridin-4-yl)-5',6'-dihydrospiro[piperidine-4,7'-pyrrolo[3,2-c]pyridin]-4'(1'H)-one (F3)

The title compound was prepared following the general procedure reported for the preparation of Example 1_1 step 6+7, using F1. The crude was purified by semi-preparative HPLC (method A) and isolated as a TFA-salt. $^1$H NMR (400 MHz, DMSO-D6, 300K): δ=1.93 (2H, br d, J=14.1 Hz), 2.26 (2H, dt, J1=13.9 Hz, J2=3.7 Hz), 3.12 (2H, br. q, 12.0 Hz), 3.33 (2H, br d, 12.8 Hz), 3.52 (2H, d, J=1.9 Hz), 7.21 (1H, d, J=2.1 Hz), 7.35 (2H, m), 7.43 (1H, dt, J1=7.5 Hz, J2=1.0 Hz), 7.67 (1H, s), 7.71 (1H, d, J=8.3 Hz), 7.78 (2H, m), 8.38 (1H, s), 8.48 (1H, m), 8.61 (1H, d, J=5.0 Hz), 8.85 (1H, br d, J=9.9 Hz), 11.84 (1H, s). MS (ES) $C_{24}H_{22}N_4O_2$ requires: 398. found: 399.1 $[M+H]^+$.

The following example(s) were prepared according to the previous method:

Example 8_2

2'-(2-(quinolin-3-yl)pyridin-4-yl)-5',6'-dihydrospiro[piperidine-4,7'-pyrrolo[3,2-c]pyridin]-4'(1'H)-one The title compound was prepared following the general procedure reported for Example 8_1 using quinolin-3-ylboronic acid and was purified by semi-preparative HPLC (method B). MS (ES) $C_{25}H_{23}N_5O$ requires: 409. found: 410.2 $[M+H]^+$.

Example 8_3

2'-(2-(benzo[d][1,3]dioxol-5-yl)pyridin-4-yl)-5',6'-dihydrospiro[piperidine-4,7'-pyrrolo[3,2-c]pyridin]-4'(1'H)-one The title compound was prepared following the general procedure reported for the preparation of Example 8_1 using benzo[d][1,3]dioxol-5-ylboronic acid, purified by semi-preparative HPLC (method A) and isolated as a TFA-salt. MS (ES) $C_{23}H_{22}N_4O_3$ requires: 402. found: 403.1 $[M+H]^+$.

Example 9_1

Synthesis of 2'-(2-(benzo[d]thiazol-2-yl)pyridin-4-yl)-5',6'-dihydrospiro[piperidine-4,7'-pyrrolo[3,2-c]pyridin]-4'(1'H)-one derivatives

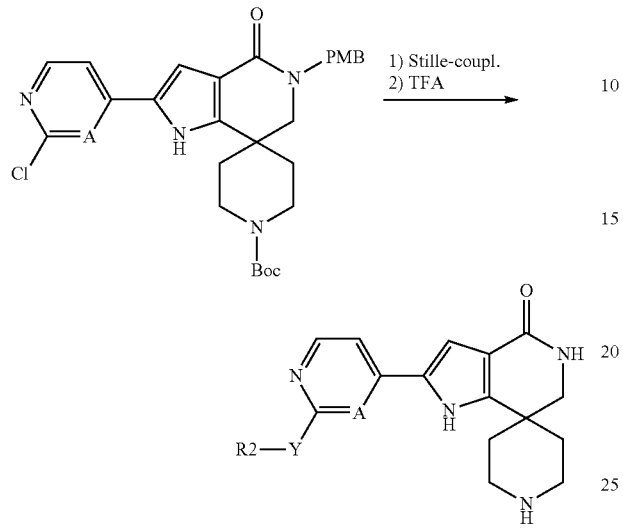

Example 9_1

2'-(2-(benzo[d]thiazol-2-yl)pyridin-4-yl)-5',6'-dihydrospiro[piperidine-4,7'-pyrrolo[3,2-c]pyridin]-4'(1'H)-one A mixture of F1 (Example 8_1 step 1) (150 mg, 0.14 mmol) and 2-(tributylstannyl)benzo[d]thiazole (89 mg, 0.209 mmol) were dissolved in toluene (4 mL) and NMP (0.1 mL). The resulting solution was purged with nitrogen, followed by addition of bis(triphenylphosphine)palladium(II) chloride (20 mg, 0.028 mmol). The resulting mixture was again purged with nitrogen and heated in the microwave for 60 min. at 150° C. After cooling to room temperature, the reaction mixture was poured into sat. NH$_4$Cl and extracted once with EtOAc. The organic layer was washed with sat. aq. NH$_4$Cl and sat. aq. NaCl dried over Na$_2$SO$_4$, filtered and concentrated in vacuo. The residue was taken up in TFA (2 mL) and heated in the microwave for 40 min. at 140° C. The crude was purified by semi-preparative HPLC (method A) and isolated as a TFA-salt. MS (ES) C$_{23}$H$_{21}$N$_5$OS requires: 415. found: 416.1 [M+H]$^+$.

The following example(s) were prepared according to the previous method:

Example 9_2

2'-(2-(benzo[d]thiazol-2-yl)pyrimidin-4-yl)-5',6'-dihydrospiro[piperidine-4,7'-pyrrolo[3,2-c]pyridin]-4'(1'H)-one The title compound was prepared following the general procedure reported for Example 9_1 using A5 and 2-(tributylstannyl)benzo[d]thiazole, purified by semi-preparative HPLC (Method A) and isolated as TFA-salt. $^1$H NMR (400 MHz, DMSO-D6, 300K): δ=1.92 (2H, d J=14.1 Hz), 2.30 (2H, dt, J1=3.9 Hz, J2=14.5 Hz), 3.12 (2H, t, J=12.5 Hz), 3.31 (1H, s), 3.53 (2H, d, J=2.3 Hz), 7.42 (1H, s), 7.45 (1H, s), 7.60 (2H, m), 8.01 (1H, d J=5.5 Hz), 8.21 (2H, t, J=8.6 Hz), 8.91 (1H, d, J=5.5 Hz), 11.93 (1H, s); MS (ES) C$_{22}$H$_{20}$N$_6$OS requires: 416. found: 417.1 [M+H]$^+$.

Example 9_3

2'-(2-(thiazol-2-yl)pyrimidin-4-yl)-5',6'-dihydrospiro[piperidine-4,7'-pyrrolo[3,2-c]pyridin]-4'(1'H)-one The title compound was prepared following the general procedure reported for Example 9_1 using A5 and 2-(tributylstannyl)thiazole, purified by semi-preparative HPLC (Method A) and was isolated as TFA-salt. $^1$H NMR (400 MHz, DMSO-D6, 300K): δ=1.90 (2H, d, J=14.1 Hz), 2.27 (2H, dt, J1=4.3 Hz, J2=14.4 Hz), 3.12 (2H, q, J=11.7 Hz), 3.30 (2H, s), 3.52 (2H, d, J=2.3), 7.36 (1H, d, J=1.9 Hz), 7.44 (1H, br s), 7.92 (1H, d, J=5.5 Hz), 8.01 (1H, d, J=3.1 Hz), 8.10 (1H, d, J=3.1 Hz), 8.26 (1H, br d, J=10.2 Hz), 8.78 (1H, br d, J=9.4 Hz), 8.83 (1H, d, J=5.5 Hz), 11.84 (1H, s); MS (ES) C$_{18}$H$_{18}$N$_6$OS requires: 366. found: 367.1 [M+H]$^+$.

Example 10_1

Synthesis of 1-(2-aminoacetyl)-2'-(2-(benzofuran-2-yl)pyrimidin-4-yl)-5',6'-dihydrospiro[piperidine-4,7'-pyrrolo[3,2-c]pyridin]-4'(1'H)-one derivatives

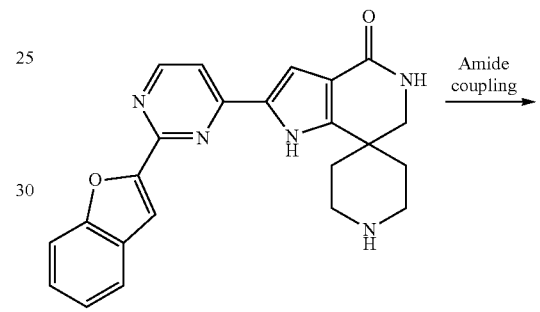

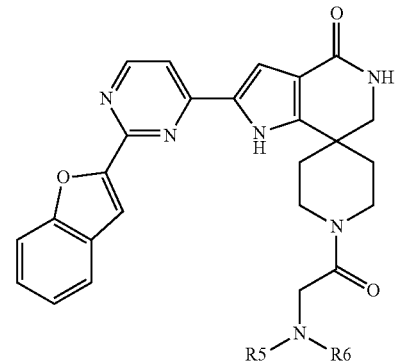

Example 10_1

1-(2-aminoacetyl)-2'-(2-(benzofuran-2-yl)pyrimidin-4-yl)-5',6'-dihydrospiro[piperidine-4,7'-pyrrolo[3,2-c]pyridin]-4'(1'H)-one Example 1_1 (70 mg, 0.11 mmol) was dissolved in a mixture of DCM (4 mL) and DMF (1 mL). Diisopropylethylamine (92 μL, 0.56 mmol), TBTU (90 mg, 0.28 mmol) and boc-aminoxyacetic acid (48.9 mg, 0.28 mmol) were added to the solution and the mixture was stirred overnight at room temperature. The reaction mixture was concentrated in vacuo. The residue was dissolved in MeOH and was brought onto a SCX-column followed by rinsing with MeOH. The product was washed off the column using 0.7 M NH$_3$ in MeOH. After concentration under vacuum, the residue was dissolved in a DCM (2 mL) and TFA (1 mL) and stirred at room temperature for 1 h. The reaction mixture was concentrated under vacuum and was purified by semi-preparative HPLC (Method A). The title compound was isolated as TFA-salt. MS (ES) $C_{25}H_{24}N_6O_3$ requires: 456. found: 457.0 $[M+H]^+$.

Example 11_1

Synthesis of 2'-(2'-(cyclopentylamino)-2,5'-bipyrimidin-4-yl)-5',6'-dihydrospiro[piperidine-4,7'-pyrrolo[3,2-c]pyridin]-4'(1'H)-one derivatives (G4)

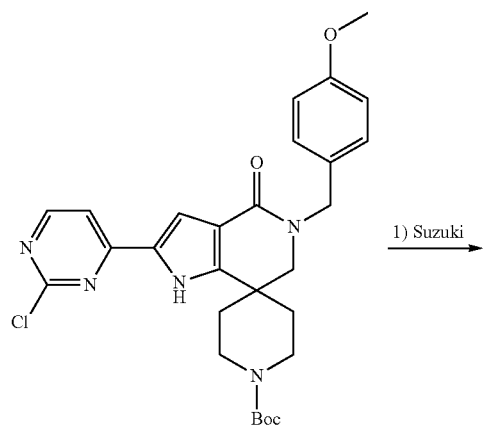

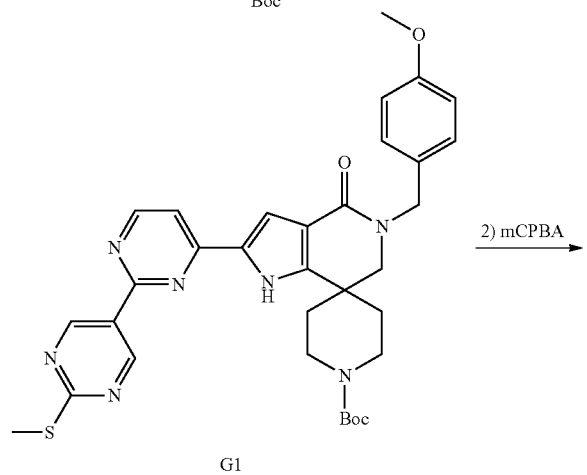

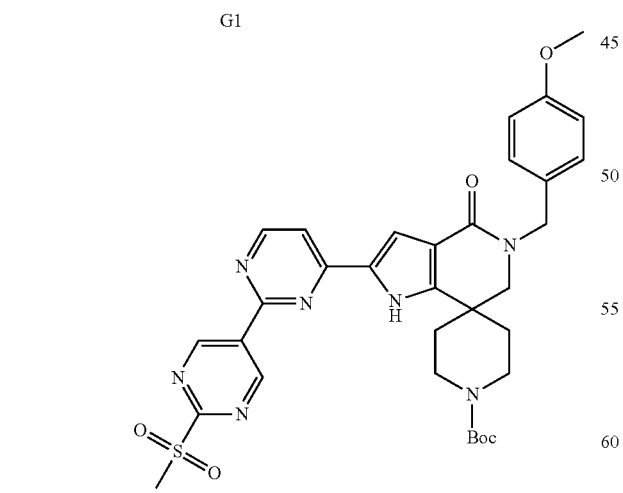

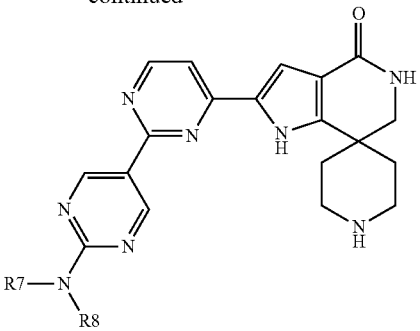

G4

Step 1: tert-butyl 5'-(4-methoxybenzyl)-2'-(2'-(methylthio)-2,5'-bipyrimidin-4-yl)-4'-oxo-1',4',5',6'-tetrahydrospiro[piperidine-4,7'-pyrrolo[3,2-c]pyridine]-1-carboxylate (G1)

The title compound was prepared following the general procedure reported for Example 1_1 step 6, using 2-(methylthio)pyrimidin-5-ylboronic acid. The crude product was dissolved in MeOH and was brought onto a SCX-column followed by rinsing with MeOH. The product was washed off the column using 0.7 M $NH_3$ in MeOH. The crude product G1 was obtained as beige solid. MS (ES) $C_{33}H_{37}N_7O_4S$ requires: 627. found: 628.2 $[M+H]^+$.

Step 2: tert-butyl 5'-(4-methoxybenzyl)-2'-(2'-(methylsulfonyl)-2,5'-bipyrimidin-4-yl)-4'-oxo-1',4',5',6'-tetrahydrospiro[piperidine-4,7'-pyrrolo[3,2-c]pyridine]-1-carboxylate (G2)

G1 (71 mg, 0.11 mmol) was dissolved in anhydrous DCM (2 mL). The solution was cooled to 0° C. After cooling 3-chlorobenzoperoxoic acid (84 mg, 0.34 mmol) was added to the solution. The reaction mixture was allowed to warm to room temperature and stirred overnight. The reaction was quenched with aqueous $NaHCO_3$-solution, followed by an extraction with DCM and aqueous $NaHCO_3$-solution. The organic layers were combined, separated with a phase-extraction filter and concentrated with a rotavapor to give the crude product (74.2 mg, 99%). MS (ES) $C_{33}H_{37}N_7O_6S$ requires: 659. found: 660.2 $[M+H]^+$.

Step 3: tert-butyl 2'-(2'-(cyclopentylamino)-2,5'-bipyrimidin-4-yl)-5'-(4-methoxybenzyl)-4'-oxo-1',4',5',6'-tetrahydrospiro[piperidine-4,7'-pyrrolo[3,2-c]pyridine]-1-carboxylate (G3)

G2 (74.2 mg, 0.11 mmol) was dissolved in N-methyl-2-pyrrolidinone (1 mL). Aminocyclopentane (1 mL, 10.10 mmol) was added to the reaction mixture and the reaction mixture was stirred at 140° C. for 2 h. The reaction was quenched by addition of some water. The reaction mixture was divided in two layers using DCM and aqueous $NH_4Cl$ solution. The organic layer was washed three times with water and once with brine. The organic layers were combined, separated with a phase-extraction filter and concentrated with a rotavapor to give the crude product (75 mg, 100%). MS (ES) $C_{37}H_{44}N_8O_4$ requires: 664. found: 665.4 $[M+H]^+$.

Step 4: Example 11_1: 2'-(2'-(cyclopentylamino)-2, 5'-bipyrimidin-4-yl)-5',6'-dihydrospiro[piperidine-4, 7'-pyrrolo[3,2-c]pyridin]-4'(1'H)-one The title compound was prepared from G3 following the general procedure reported for Example 1_1 step 7, and was purified by semi-preparative HPLC (Method A). The title compound was isolated as TFA-salt. $^1$H NMR (400 MHz, DMSO-D6, 300K): δ=1.56 (4H, m), 1.71 (2H, br s), 1.92 (4H, m), 2.30 (2H, dt, J1=3.9 Hz, J2=14.1 Hz), 2.69 (1H, s), 3.12 (2H, q, J=11.3 Hz), 3.31 (2H, q, J=12.5 Hz), 3.52 (2H, d, J=2.3 Hz), 4.27 (1H, q, J=6.6 Hz), 7.36 (1H, d, J=2.0 Hz), 7.41 (1H, s), 7.70 (1H, d, J=5.5 Hz), 7.82 (1H, d, J=7.0 Hz), 8.32 (1H, br d, J=10.5 Hz), 8.76 (1H, br d, J=10.6 Hz), 9.32 (1H, br s), 9.42 (1H, br s), 11.65 (1H, s); MS (ES) $C_{24}H_{28}N_8O$ requires: 444. found: 445.4 $[M+H]^+$.

Example 12

Synthesis of N-(4-(4'-oxo-1',4',5',6'-tetrahydrospiro [piperidine-4,7'-pyrrolo[3,2-c]pyridine]-2'-yl)pyridin-2-yl)-4-(trifluoromethyl)benzamide derivatives

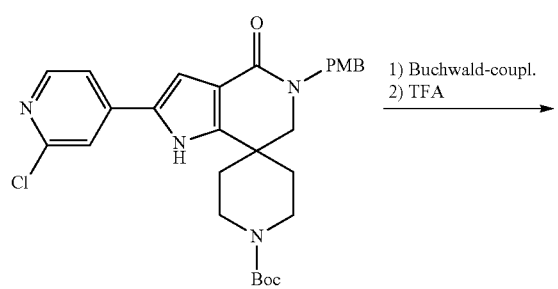

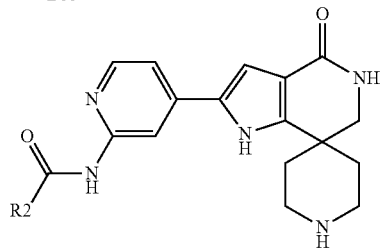

Example 12_1

N-(4-(4'-oxo-1',4',5',6'-tetrahydrospiro[piperidine-4, 7'-pyrrolo[3,2-c]pyridine]-2'-yl)pyridin-2-yl)-4-(trifluoromethyl)benzamide A mixture of F1 (Example 8_1 step 1) (90 mg, 0.168 mmol), 4-(trifluoromethyl)benzamide (70 mg, 0.370 mmol), 4,5-bis(diphenylphosphino)-9,9-dimethylxanthene (26 mg, 0.045 mmol) and sodium tert-butoxide (71 mg, 0.739 mmol) were dissolved in DMF (4 mL). The resulting mixture was purged with nitrogen, followed by addition of palladium(II) acetate (5.1 mg, 0.023 mmol). The resulting mixture was again purged with nitrogen and heated in the microwave for 40 min. at 150° C. After cooling to room temperature, the reaction mixture was loaded on a SCX-2 column and washed with methanol, water and methanol. The product was rinsed off the column with 0.7 N $NH_3$ in methanol and concentrated in vacuo. The residue was dissolved in TFA (1.5 mL) and heated in the microwave for 25 min. at 140° C. The reaction mixture was concentrated in vacuo and the residue was loaded on a SCX-2 column, washed with methanol, water and methanol. The product was rinsed off the column with 0.7 N $NH_3$ in methanol and concentrated in vacuo. The residue was purified by semi-preparative HPLC (method A) and isolated as a TFA-salt. $^1$H NMR (400 MHz, DMSO-D6, 300K): δ=1.84 (2H, br d, J=13.9 Hz), 2.22 (2H, dt, J1=13.9 Hz, J2=4.3 Hz), 3.11 (2H, q, J=12.6 Hz), 3.31 (2H, d, J=12.6 Hz), 3.50 (2H, d, J=1.3 Hz), 6.94 (1H, d, J=3.0 Hz), 7.35 (1H, s), 7.57 (1H, d, J=5.2 Hz), 7.92 (2H, d, J=8.7 Hz), 8.23 (2H, d, J=6.9 Hz), 8.38 (1H, dd, J1=5.2 Hz, J2=1.3 Hz), 8.40 (1H, m), 8.42 (1H, s), 8.80 (1H, d, J=10.4 Hz), 11.13 (1H, s), 11.75 (1H, s); MS (ES) $C_{24}H_{22}F_3N_5O_2$ requires: 469. found: 470.1 $[M+H]^+$.

Example 12_2

3,4-dimethyl-N-(4-(4'-oxo-1',4',5',6'-tetrahydrospiro [piperidine-4,7'-pyrrolo[3,2-c]pyridine]-2'-yl)pyridin-2-yl)benzamide The title compound was prepared following the general procedure reported for Example 12_1 using 3,4-dimethylbenzamide. $^1$H NMR (400 MHz, DMSO-D6, 300K): δ=1.89 (2H, br. d, J=14.4 Hz), 2.21 (2H, dt, J1=14.3 Hz, J2=3.4 Hz), 2.31 (6H, s), 3.11 (2H, q, J=12.4 Hz), 3.31 (2H, d, J=12.4 Hz), 3.50 (2H, s), 6.96 (1H, d, J=1.9 Hz), 7.30 (1H, d, J=7.9 Hz), 7.36 (1H, s), 7.56 (1H, dd, J1=5.3 Hz, J2=1.5 Hz), 7.80 (1H, d, J=7.9 Hz), 7.88 (1H, s), 8.35 (1H, d, J=5.3 Hz), 8.38 (1H, s), 8.40 (1H, m), 8.79 (1H, d, J=10.8 Hz), 10.77 (1H, s), 11.77 (1H, s); MS (ES) $C_{25}H_{27}N_5O_2$ requires: 429. found: 430.2 $[M+H]^+$.

Example 13

Synthesis of N-(4-(4'-oxo-1',4',5',6'-tetrahydrospiro [piperidine-3,7'-pyrrolo[3,2-c]pyridine]-2'-yl)pyrimidin-2-yl)-4-(trifluoromethyl)benzamide derivatives

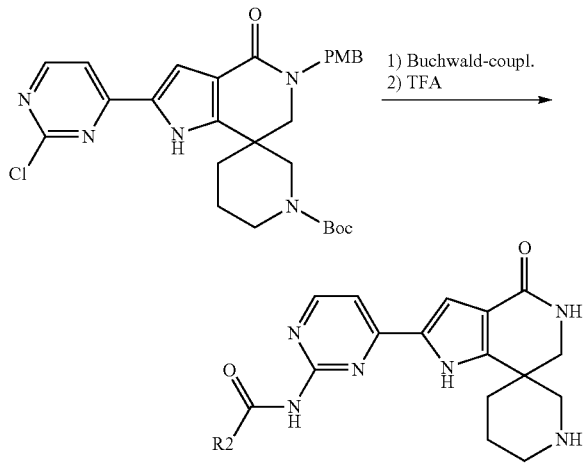

Example 13_1

N-(4-(4'-oxo-1',4',5',6'-tetrahydrospiro[piperidine-3, 7'-pyrrolo[3,2-c]pyridine]-2'-yl)pyrimidin-2-yl)-4-(trifluoromethyl)benzamide A mixture of C6 (Example 5_1 step 6) (80 mg, 0.149 mmol), 4-(trifluoromethyl)benzamide (62 mg, 0.327 mmol), 4,5-bis(diphenylphosphino)-9,9-dimethylxanthene (24 mg, 0.041 mmol) and sodium tert-butoxide (65 mg, 0.676 mmol) were dissolved in DMF (4 mL). The resulting mixture was purged with nitrogen, followed by addition of palladium(II) acetate (4.7 mg, 0.021 mmol). The resulting mixture was again purged with nitrogen and heated in the microwave for 30 min. at 150° C. After cooling to room temperature, the reaction mixture was poured into sat. NH$_4$Cl and extracted once with ethyl acetate. The organic layer was washed with sat. NH$_4$Cl, sat. NaCl dried over Na$_2$SO$_4$, filtered and concentrated in vacuo. The residue was dissolved in TFA (1.5 mL) and heated in the microwave for 25 min. at 140° C. The reaction mixture was concentrated in vacuo and the residue was loaded on a SCX-2 column, washed with methanol, water and methanol. The product was rinsed off the column with 0.7 N NH$_3$ in methanol and concentrated in vacuo. The residue was purified by semi-preparative HPLC (method A) and isolated as a TFA-salt. $^1$H NMR (400 MHz, DMSO-D6, 300K): δ=1.69 (1H, m), 1.82 (2H, d, J=12.1 Hz), 2.17 (1H, dt, J1=13.4 Hz, J2=3.0 Hz), 2.78 (1H, m), 3.24-3.48 (4H, m), 3.60 (1H, d, J=13.0 Hz), 7.29 (1H, s), 7.44 (1H, s), 7.66 (1H, d, J=6.1 Hz), 7.90 (2H, d, J=7.80 Hz), 8.16 (2H, d, J=7.8 Hz), 8.46 (1H, m), 8.67 (1H, d, J=5.2 Hz), 9.06 (1H, d, J=10.4 Hz), 11.17 (1H, s), 11.79 (1H, s); MS (ES) C$_{23}$H$_{21}$F$_3$N$_6$O$_2$ requires: 470. found: 471.1 [M+H]$^+$.

Example 13_2

N-(4-(4'-oxo-1',4',5',6'-tetrahydrospiro[piperidine-3,7'-pyrrolo[3,2-c]pyridine]-2'-yl)pyrimidin-2-yl)-3-(trifluoromethoxy)benzamide The title compound was prepared following the general procedure reported for Example 13_1 using 3-(trifluoromethoxy)benzamide. $^1$H NMR (400 MHz, DMSO-D6, 300K): δ=1.70 (1H, m), 1.83 (2H, d, J=12.1 Hz), 2.18 (1H, dt, J1=13.0 Hz, J2=3.5 Hz), 2.78 (1H, q, J=11.7 Hz), 3.26-3.48 (4H, m), 3.60 (1H, dd, J1=13.4 Hz, J2=2.6 Hz), 7.30 (1H, d, J=2.2 Hz), 7.44 (1H, s), 7.62-7.71 (3H, m), 7.96 (1H, s), 8.04 (1H, d, J=7.4 Hz), 8.48 (1H, m), 8.67 (1H, d, J=5.2 Hz), 9.09 (1H, d, J=8.7 Hz), 11.17 (1H, s), 11.80 (1H, s); MS (ES) C$_{23}$H$_{21}$F$_3$N$_6$O$_3$ requires: 486. found: 487.1 [M+H]$^+$.

Example 14

MK2 Enzyme Activity

MK2 enzyme activity is measured using the IMAP (immobilized metal ion affinity-based fluorescence polarization) assay as outlined below.

The enzyme is diluted to 100 U/mL the day before use in KR buffer (10 mM Tris-HCl, 10 mM MgCl2, 0.01% Tween-20, 0.05% NaN3, 2 mM DTT, pH 7.2) and stored overnight at −20° C.

Serial dilution log 10 from 2 mM to 63.2 nM of test compounds are made in 100% DMSO. The dilutions in DMSO are then diluted 50-fold in KR-buffer of which 5 µl is used in the assay, leading to a final compound concentration range in the assay from 10 µM to 0.316 nM.

5 µL/well of test compound in KR buffer (final DMSO concentration in the assay is 0.5%) is mixed with 5 µl/well of 0.1 U/mL MK2 enzyme (active enzyme (peptide 46-end (Millipore), final concentration in the assay is 25 mU/mL). Test compounds and MK2 enzyme are pre-incubated 30 minutes at room temperature, before adding 5 µl/well of 200 nM Fluorescin labeled substrate peptide (Fluo-betaA-11A NeoMPS final substrate peptide concentration is 50 nM) in KR-buffer. The kinase assay is started by adding 5 L/well of 4 µM ATP in KR-buffer (final ATP concentration is 1 µM ATP, Km ATP in MK2 IMAP assay). Following incubation for 2 h at room temperature the enzyme reaction is stopped by adding 20 µL/well IMAP Progressive Binding Solution (according to suppliers (Molecular Devices) protocol using 100% 1× buffer A with 1:400 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (ΔmPi) of the controls with and without ATP. EC$_{50}$ values are determined by curve fitting of the experimental results using Activity Base. Examples 1_14, 1_18, 1_19, 1_20, 1_26, 1_33, 1_34, 2_2, 2_3, 3_2, 7_1, 9_3, 10_1, 13_1, 13_2 have a pEC50 value of 6.5-7.5.

Examples 1_1, 1_3, 1_4, 1_5, 1_6, 1_7, 1_8, 1_9, 1_10, 1_11, 1_12, 1_13, 1_15, 1_16, 1_17, 1_21, 1_22, 1_23, 1_24, 1_25, 1_27, 1_28, 1_29, 1_30, 1_31, 1_32, 1_35, 1_36, 2_1, 3_1, 4_1, 4_2, 4_4, 4_5, 5_1, 5_2, 6_2, 6_3, 6_4, 6_5, 8_1, 9_1, 9_2, have a pEC50 value of 7.5-8.5.

Examples 1_2, 4_3, 6_1, 8_2, 8_3, 11_1, 12_1, 12_2 have a pEC50 value of ≥8.5

Example 15

Solubility Determination of MK2 Inhibitors

The samples were prepared from 10 mM DMSO stock solutions. For each compound under investigation, a volume (9 µL) of the DMSO stock solution is transferred from the DMSO stock solution into 891 µL of buffer solution (system solution from pION inc.) in a 96 deep well plate, which equates to approximately 1% DMSO, using the Packard Multiprobe II robot liquid handling system. The pH of the buffer is manually adjusted at pH 7.4 by adding NaOH. This procedure is done in duplicate for each sample. After shaking for 24 h on a vortex mixer (Heidolph, Titramax 101) at 450 rpm and at room temperature (21-23° C.), 300 uL of the incubated sample is transferred from the deep well plate to a filter plate (PVDF, 0.45 um) on a vacuum manifold. To the filtrate (150 uL) 1-propanol (50 uL) is added to suppress precipitation and this solution is then analysed by UPLC. The solubility is determined using the calibration line previously prepared.

Preparation of the Standards and Built up of a Calibration Line

The calibration line is built with different concentrations of the test compound (standards), prepared from the same 10 mM DMSO stock solution. A volume (7 uL) from the same DMSO stock solution was diluted with DMSO (273 uL) leading to a solution with concentration of 0.25 mM. From this solution, three different injection volumes (0.2, 1, 1.8 uL) were injected on UPLC. The respective peak areas are plotted against amount of compound to build up the calibration line. The calibration line is used to determine the amount of dissolved compound in each sample, selecting the injection that gave peak areas closest to the peak area range of the calibration standards. This result was then converted to the solubility in mg/L.

The following examples have a solubility of ≥20-50 mg/L: 1_1, 1_2, 1_3, 1_4, 1_5, 1_6, 1_7, 1_12, 1_14, 1_18, 1_21, 1_26, 2_1, 4_1, 4_2, 4_4, 6_1, 6_4, 8_2, 12_1, 13_1, 13_2

The following examples have a solubility of ≥50 mg/L:
1__8, 1__9, 1__10, 1__11, 1__13, 1__15, 1__16, 1__17, 1__19, 1__20, 1__22, 1__23, 1__24, 1__25, 1__27, 1__28, 1__29, 1__30, 1__31, 1__32, 1__33, 1__34, 1__35, 1__36, 2__2, 2__3, 3__1, 3__2, 4__3, 4__5, 5__1, 5__2, 6__2, 6__3, 6__5, 7__1, 8__1, 8__3, 9__1, 9__2, 9__3, 10__1, 11__1, 12__2.

Example 16

Comparison of Structures of Formula (I) with Formula (XV)

Structures of the type (XV) have previously been identified as MK2 inhibitors [WO2004058762]. Examples with formula (XV) have been prepared according to the experimental procedures described in WO2004058762, and tested for MK2 enzyme activity and solubility as described in Example 14 and 15. Subsequently, examples of formula (I) and (XV) were compared head to head for MK2 activity and solubility (Table 1, Examples 16__1-16__8). MK2 inhibitors according to formula (I) according to the present invention, while having otherwise exactly the same substituents R1, R2 and A (Table 1), have improved activity and solubility due to the introduction of an amine-containing spiro ring (V, X and W=—CH$_2$—, and R3=H). Comparable compounds without the spiro modification (XV) have either good solubility, but lower MK2 inhibition or acceptable MK2 inhibition, but poor solubility (Table 1).

Example 17

Comparison of Structures of Formula (I) with Formula (XVI)

Structures of the type (XVI) have been prepared in analogy with the preparation described for structures op the type (I). MK2 enzyme activity and solubility was determined as described in Example 14 and 15. Subsequently, examples of formula (I) and (XVI) were compared head to head for MK2 activity and solubility (Table 2, Examples 17__1-17__4). MK2 inhibitors according to formula (I) according to this invention, while having otherwise exactly the same substituents R1, R2 and A (Table 2), have improved activity and solubility due to the introduction of an amine-containing Spiro ring such as a 4-piperidyl or 3-pyrrolidyl ring). Comparable compounds without the amine have lower solubility, and lower MK2 inhibition (Table 2).

Example 17__1

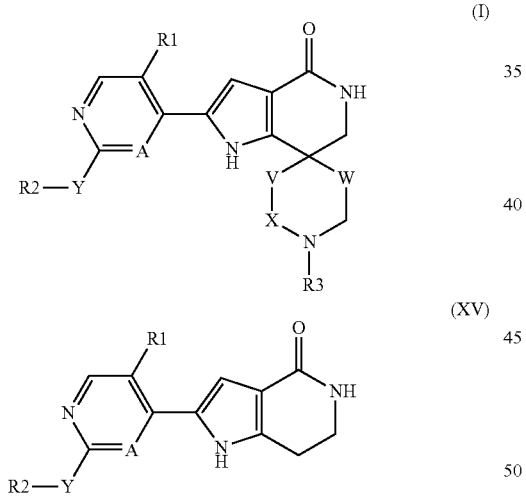

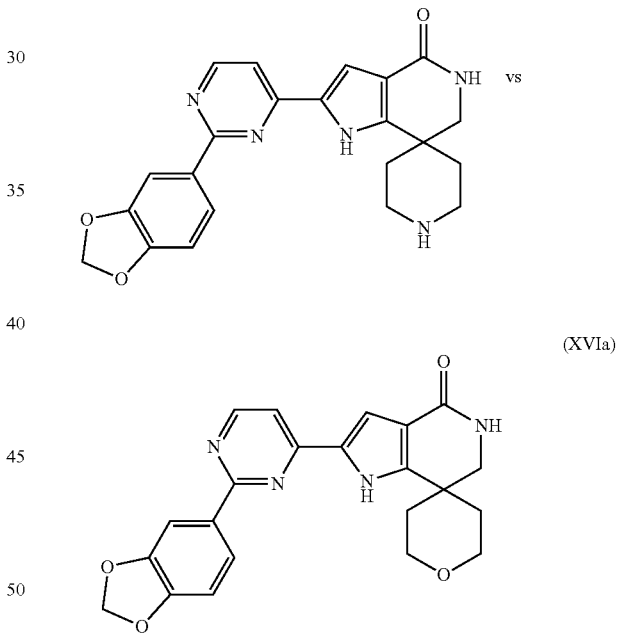

TABLE 1

| | | | | | | Formula (I) | | Formula (XV) | |
|---|---|---|---|---|---|---|---|---|---|
| Example | R1 | R2 | A | Y | Spiro ring | Solubility pH 7.4 (mg/L) | pEC50 | Solubility pH 7.4 (mg/L) | pEC50 |
| 16__1 | H | Quinolin-3-yl | CH | bond | 4-Piperidyl | 35 | 8.9 | 2 | 7.2 |
| 16__2 | H | Quinolin-3-yl | N | bond | 4-Piperidyl | 23 | 8.2 | 0 | 8 |
| 16__3 | H | 3-F-Phenyl | N | bond | 4-Piperidyl | 36 | 8.1 | 32 | 6.3 |
| 16__4 | H | 2-F-Phenyl | N | bond | 4-Piperidyl | 36 | 7.5 | 44 | 6 |
| 16__5 | H | 3,4-Methylen-dioxo-phenyl | N | bond | 4-Piperidyl | 37 | 8.4 | 5 | 6.9 |
| 16__6 | H | Benzofuran-2-yl | N | bond | 4-Piperidyl | 84 | 8.2 | 2 | 7.3 |
| 16__7 | H | Benzofuran-2-yl | CH | bond | 4-Piperidyl | 66 | 8.5 | 2 | 6.9 |
| 16__8 | H | 4-MeCO-phenyl | N | bond | 4-Piperidyl | 35 | 8.2 | 3 | 6.9 |

Example 17_2
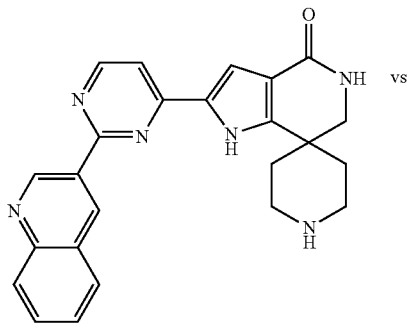
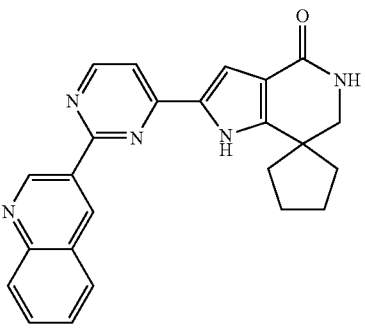
(XVIc)
Example 17_4
(XVIb)
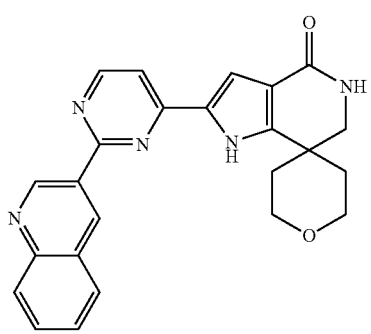
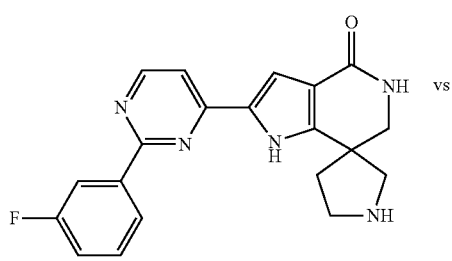
Example 17_3
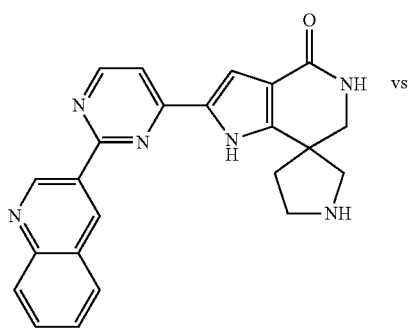
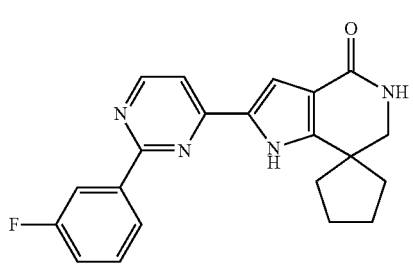
(XVId)
TABLE 2
| | | | | | | Formula (I) | | Formula (XVI) | |
|---|---|---|---|---|---|---|---|---|---|
| Example | R1 | R2 | A | Y | Spiro ring | Solubility pH 7.4 (mg/L) | pEC50 | Solubility pH 7.4 (mg/L) | pEC50 |
| 17_1 | H | 3,4-Methylen-dioxo-phenyl | N | bond | 4-Piperidyl vs 4-THP | 37 | 8.4 | 2 | 6.1 |
| 17_2 | H | Quinolin-3-yl | N | bond | 4-Piperidyl vs 4-THP | 23 | 8.2 | 3 | 6.5 |
| 17_3 | H | Quinolin-3-yl | N | bond | 3-Pyrrolidyl vs Cyclopentyl | 37 | 8.6 | 0 | 6.6 |
| 17_4 | H | 3-F-phenyl | N | bond | 3-Pyrrolidyl vs Cyclopentyl | 48 | 7.9 | 0 | 6.5 |

Example 18

The following compounds were prepared using the synthesis described herein:

- 2'-(2-(6-aminopyridin-3-yl)pyrimidin-4-yl)-5',6'-dihydrospiro[piperidine-4,7'-pyrrolo[3,2-c]pyridin]-4'(1'H)-one;
- 2'-(2-(pyridin-3-yl)pyrimidin-4-yl)-5',6'-dihydrospiro[piperidine-4,7'-pyrrolo[3,2-c]pyridin]-4'(1'H)-one;
- 2'-(2-(pyridin-3-yl)pyrimidin-4-yl)-5',6'-dihydrospiro[piperidine-3,7'-pyrrolo[3,2-c]pyridin]-4'(1'H)-one;
- (S)-2'-(2-(pyridin-3-yl)pyrimidin-4-yl)-5',6'-dihydrospiro[piperidine-3,7'-pyrrolo[3,2-c]pyridin]-4'(1'H)-one;
- (R)-2'-(2-(pyridin-3-yl)pyrimidin-4-yl)-5',6'-dihydrospiro[piperidine-3,7'-pyrrolo[3,2-c]pyridin]-4'(1'H)-one;
- 2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;
- (S)-2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;
- (R)-2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;
- 2'-((5-methoxypyridin-3-yl)pyrimidin-4-yl)-5',6'-dihydrospiro[piperidine-3,7'-pyrrolo[3,2-c]pyridin]-4'(1'H)-one;
- (S)-2'-(2-(5-methoxypyridin-3-yl)pyrimidin-4-yl)-5',6'-dihydrospiro[piperidine-3,7'-pyrrolo[3,2-c]pyridin]-4'(1'H)-one;
- (R)-2'-(2-(5-methoxypyridin-3-yl)pyrimidin-4-yl)-5',6'-dihydrospiro[piperidine-3,7'-pyrrolo[3,2-c]pyridin]-4'(1'H)-one;
- 2'-(2'-(cyclopentylamino)-2,5'-bipyrimidin-4-yl)-5',6'-dihydrospiro[piperidine-4,7'-pyrrolo[3,2-c]pyridin]-4'(1'H)-one;
- 3,4-dimethyl-N-(4-(4'-oxo-1',4',5',6'-tetrahydrospiro[piperidine-4,7'-pyrrolo[3,2-c]pyridine]-2'-yl)pyrimidin-2-yl)benzamide;
- 3,4-dimethyl-N-(4-(4'-oxo-1',4',5',6'-tetrahydrospiro[piperidine-4,7'-pyrrolo[3,2-c]pyridine]-2'-yl)pyridin-2-yl)benzamide;
- 3-fluoro-N-(4-(4'-oxo-1',4',5',6'-tetrahydrospiro[piperidine-4,7'-pyrrolo[3,2-c]pyridine]-2'-yl)pyridin-2-yl)benzamide;
- 3-fluoro-N-(4-(4'-oxo-1',4',5',6'-tetrahydrospiro[piperidine-4,7'-pyrrolo[3,2-c]pyridine]-2'-yl)pyridin-2-yl)benzamide;
- N-(4-(4'-oxo-1',4',5',6'-tetrahydrospiro[piperidine-4,7'-pyrrolo[3,2-c]pyridine]-2'-yl)pyridin-2-yl)picolinamide;
- 4-fluoro-N-(4-(4'-oxo-1',4',5',6'-tetrahydrospiro[piperidine-4,7'-pyrrolo[3,2-c]pyridine]-2'-yl)pyrimidin-2-yl)benzamide;
- 4-fluoro-N-(4-(4'-oxo-1',4',5',6'-tetrahydrospiro[piperidine-4,7'-pyrrolo[3,2-c]pyridine]-2'-yl)pyridin-2-yl)benzamide;
- N-(4-(4'-oxo-1',4',5',6'-tetrahydrospiro[piperidine-4,7'-pyrrolo[3,2-c]pyridine]-2'-yl)pyrimidin-2-yl)-2-naphthamide;
- N-(4-(4'-oxo-1',4',5',6'-tetrahydrospiro[piperidine-4,7'-pyrrolo[3,2-c]pyridine]-2'-yl)pyridin-2-yl)-2-naphthamide;
- N-(4-(4'-oxo-1',4',5',6'-tetrahydrospiro[piperidine-4,7'-pyrrolo[3,2-c]pyridine]-2'-yl)pyrimidin-2-yl)-1-naphthamide;
- N-(4-(4'-oxo-1',4',5',6'-tetrahydrospiro[piperidine-4,7'-pyrrolo[3,2-c]pyridine]-2'-yl)pyridin-2-yl)-1-naphthamide;
- N-(4-(4'-oxo-1',4',5',6'-tetrahydrospiro[piperidine-4,7'-pyrrolo[3,2-c]pyridine]-2'-yl)pyridin-2-yl)biphenyl-4-carboxamide;
- N-(4-(4'-oxo-1',4',5',6'-tetrahydrospiro[piperidine-4,7'-pyrrolo[3,2-c]pyridine]-2'-yl)pyridin-2-yl)-4-(trifluoromethyl)benzamide;
- 3-(dimethylamino)-N-(4-(4'-oxo-1',4',5',6'-tetrahydrospiro[piperidine-4,7'-pyrrolo[3,2-c]pyridine]-2'-yl)pyridin-2-yl)benzamide;
- N-(4-(4'-oxo-1',4',5',6'-tetrahydrospiro[piperidine-4,7'-pyrrolo[3,2-c]pyridine]-2'-yl)pyridin-2-yl)isonicotinamide;
- 6-methoxy-N-(4-(4'-oxo-1',4',5',6'-tetrahydrospiro[piperidine-4,7'-pyrrolo[3,2-c]pyridine]-2'-yl)pyridin-2-yl)picolinamide;
- 3,4-dimethyl-N-(4-(1-methyl-4'-oxo-1',4',5',6'-tetrahydrospiro[piperidine-4,7'-pyrrolo[3,2-c]pyridine]-2'-yl)pyridin-2-yl)benzamide;
- 3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
- (S)-3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
- (R)-3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
- 3,4-dimethyl-N-(4-(4'-oxo-1',4',5',6'-tetrahydrospiro[pyrrolidine-3,7'-pyrrolo[3,2-c]pyridine]-2'-yl)pyridin-2-yl)benzamide;
- N-(4-(1-methyl-4'-oxo-1',4',5',6'-tetrahydrospiro[piperidine-4,7'-pyrrolo[3,2-c]pyridine]-2'-yl)pyridin-2-yl)-3-(trifluoromethoxy)benzamide;
- N-(4-(4'-oxo-1',4',5',6'-tetrahydrospiro[piperidine-3,7'-pyrrolo[3,2-c]pyridine]-2'-yl)pyridin-2-yl)-3-(trifluoromethoxy)benzamide;
- N-(4-(4'-oxo-1',4',5',6'-tetrahydrospiro[pyrrolidine-3,7'-pyrrolo[3,2-c]pyridine]-2'-yl)pyridin-2-yl)-3-(trifluoromethoxy)benzamide;
- 3-fluoro-N-(4-(1-methyl-4'-oxo-1',4',5',6'-tetrahydrospiro[piperidine-4,7'-pyrrolo[3,2-c]pyridine]-2'-yl)pyridin-2-yl)benzamide;
- 3-fluoro-N-(4-(4'-oxo-1',4',5',6'-tetrahydrospiro[piperidine-3,7'-pyrrolo[3,2-c]pyridine]-2'-yl)pyridin-2-yl)benzamide;
- 3-fluoro-N-(4-(4'-oxo-1',4',5',6'-tetrahydrospiro[pyrrolidine-3,7'-pyrrolo[3,2-c]pyridine]-2'-yl)pyridin-2-yl)benzamide;
- N-(4-(4'-oxo-1',4',5',6'-tetrahydrospiro[piperidine-3,7'-pyrrolo[3,2-c]pyridine]-2'-yl)pyridin-2-yl)picolinamide;
- N-(4-(4'-oxo-1',4',5',6'-tetrahydrospiro[pyrrolidine-3,7'-pyrrolo[3,2-c]pyridine]-2'-yl)pyridin-2-yl)picolinamide;
- 4-fluoro-N-(4-(4'-oxo-1',4',5',6'-tetrahydrospiro[piperidine-3,7'-pyrrolo[3,2-c]pyridine]-2'-yl)pyridin-2-yl)benzamide;
- (S)-4-fluoro-N-(4-(4'-oxo-1',4',5',6'-tetrahydrospiro[piperidine-3,7'-pyrrolo[3,2-c]pyridine]-2'-yl)pyridin-2-yl)benzamide;
- (R)-4-fluoro-N-(4-(4'-oxo-1',4',5',6'-tetrahydrospiro[piperidine-3,7'-pyrrolo[3,2-c]pyridine]-2'-yl)pyridin-2-yl)benzamide;

4-fluoro-N-(4-(4'-oxo-1',4',5',6'-tetrahydrospiro[pyrrolidine-3,7'-pyrrolo[3,2-c]pyridine]-2'-yl)pyridin-2-yl)benzamide;

N-(4-(1-methyl-4'-oxo-1',4',5',6'-tetrahydrospiro[piperidine-4,7'-pyrrolo[3,2-c]pyridine]-2'-yl)pyridin-2-yl)-2-naphthamide;

N-(4-(4'-oxo-1',4',5',6'-tetrahydrospiro[piperidine-3,7'-pyrrolo[3,2-c]pyridine]-2'-yl)pyridin-2-yl)-2-naphthamide;

(S)—N-(4-(4'-oxo-1',4',5',6'-tetrahydrospiro[piperidine-3,7'-pyrrolo[3,2-c]pyridine]-2'-yl)pyridin-2-yl)-2-naphthamide;

N-(4-(4'-oxo-1',4',5',6'-tetrahydrospiro[pyrrolidine-3,7'-pyrrolo[3,2-c]pyridine]-2'-yl)pyridin-2-yl)-2-naphthamide;

N-(4-(4'-oxo-1',4',5',6'-tetrahydrospiro[piperidine-3,7'-pyrrolo[3,2-c]pyridine]-2'-yl)pyridin-2-yl)-3-(trifluoromethyl)benzamide;

3,5-difluoro-N-(4-(4'-oxo-1',4',5',6'-tetrahydrospiro[piperidine-3,7'-pyrrolo[3,2-c]pyridine]-2'-yl)pyridin-2-yl)benzamide;

N-(4-(4'-oxo-1',4',5',6'-tetrahydrospiro[piperidine-3,7'-pyrrolo[3,2-c]pyridine]-2'-yl)pyridin-2-yl)-1-naphthamide;

N-(4-(4'-oxo-1',4',5',6'-tetrahydrospiro[piperidine-3,7'-pyrrolo[3,2-c]pyridine]-2'-yl)pyridin-2-yl)quinoline-2-carboxamide;

N-(4-(4'-oxo-1',4',5',6'-tetrahydrospiro[piperidine-3,7'-pyrrolo[3,2-c]pyridine]-2'-yl)pyridin-2-yl)isoquinoline-1-carboxamide;

N-(4-(4'-oxo-1',4',5',6'-tetrahydrospiro[piperidine-3,7'-pyrrolo[3,2-c]pyridine]-2'-yl)pyridin-2-yl)-4-(trifluoromethyl)benzamide.

All compounds have a pEC50 of at least 6.5 and a solubility of at least 20 mg/L as determined according to the assay described in examples 14 and 15.

The invention claimed is:

1. A compound of Formula I,

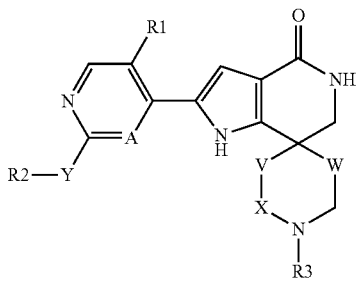

Formula I or a pharmaceutically acceptable salt thereof, wherein
A is CH or N;
Y is a bond, or —C(O)NH—;
X is a bond, —CH$_2$—, —CH$_2$CH$_2$—;
V is —CH$_2$—, O, C(O), —CHF—, or —CF$_2$—, with the proviso that if V is O, X is —CH$_2$CH$_2$— and that if V is C(O), X is —CH$_2$;
W is a bond or —CH$_2$—;
R1 is hydrogen or F;
R2 is a (1-12C)heteroaryl or (6-10C)aryl both optionally substituted with one or more groups independently selected from R4;

R3 is a hydrogen; (3-6C)cycloalkyl; (1-6C)alkyl, —(CH$_2$)$_m$OR5; —(CH$_2$)$_m$NR5R6; or —C(O)CH$_2$NR5R6;

R4 is taken from halogen; OH; SH; nitrile, nitro, NH$_2$; (3-6C)cycloalkyl, (3-6C)cycloalkoxy, (1-6C)alkoxy or (1-6C)alkyl, all optionally substituted with one or more halogen; phenoxy; —O(CH$_2$)$_m$OR5, —O(CH$_2$)$_m$NR7R8, —OC(O)R7 with the proviso that R7 is not hydrogen, —O(1-12C)heteroaryl), —S(1-6C)alkyl); —S(3-6C)cycloalkyl)-; NR7R8; —NR9(CH$_2$)$_m$OR7, —NR9(CH$_2$)$_m$NR7R8; (1-6C)alkylcarbonyl; (3-6C)cycloalkylcarbonyl; —C(O)NR7R8; —C(O)NR9(CH$_2$)$_m$NR7R8, —C(O)NR9(CH$_2$)$_m$OR7, —C(O)OR7, —SO$_2$(1-6C)alkyl), —SO$_2$(3-6C)cycloalkyl); —O(1-6C)alkyl)O— where the oxygens are attached to the (1-12C)heteroaryl or (6-10C)aryl ring on two neighboring carbons; phenyl or (1-12C)heteroaryl;

R5 is hydrogen (3-6C)cycloalkyl; or (1-6C)alkyl;
R6 is hydrogen; (3-6C)cycloalkyl; (1-6C)alkyl; or (1-6C)alkylcarbonyl;
R7 is hydrogen, (1-6C)alkyl or (3-6C)cycloalkyl;
R8 is hydrogen; (3-6C)cycloalkyl; (1-6C)alkyl; or (1-6C)alkylcarbonyl; or
R7 and R8 together with the nitrogen to which they are bonded in NR7R8 can form a 5-7-membered at least one nitrogen containing (4-6C)heterocyclyl ring which optionally contains one additional heteroatom selected from N, O or S;
R9 is hydrogen; (1-6C)alkyl or (3-6)cycloalkyl; and
m is 2 or 3.

2. The compound according to claim 1, wherein
V is —(CH$_2$)— or O, with the proviso that if V is O, X is —CH$_2$CH$_2$—;
R4 is taken from halogen; OH; NH$_2$; (3-6C)cycloalkyl or (1-6C)alkyl, both optionally substituted with one or more halogen; (3-6C)cycloalkoxy; (1-6C)alkoxy; phenoxy; —NR7R8; (1-6C)alkylcarbonyl; (3-6C)cycloalkylcarbonyl; —C(O)NR7R8; —O(1-6C)alkyl)O— where the oxygens are attached to the (1-12C)heteroaryl or (6-10C)aryl ring on two neighboring carbons; phenyl or (1-5C)heteroaryl.

3. The compound according to claim 1, wherein V is —CH$_2$—.

4. The compound according to claim 1, wherein W is —CH$_2$—.

5. The compound according to claim 1, wherein X is —CH$_2$—.

6. The compound according to claim 1, wherein R2 is (1-5C)heteroaryl optionally substituted with one or more groups independently selected from R4 wherein R4 is selected from —NR7R8; NH$_2$ or (1-6C)alkoxy.

7. The compound according to claim 1, wherein R2 is phenyl optionally substituted with one or more groups independently selected from R4 wherein
R4 is taken from halogen; OH; (3-6C)cycloalkyl or (1-6C)alkyl, both optionally substituted with one or more halogen; (1-6C)alkoxy; phenoxy; (1-6C)alkylcarbonyl; (3-6C)cycloalkylcarbonyl; —C(O)NR7R8; —O(1-6C)alkyl)O— where the oxygens are attached to the (hetero)aryl ring on two neighboring carbons or phenyl.

8. The compound according to claim 1, wherein R3 is hydrogen; —(CH$_2$)$_m$NR5R6, or —C(O)CH$_2$NR5R6.

9. The compound according to claim 8 wherein R3 is hydrogen.

10. The compound according to claim 1, wherein R3 is methyl, and Y=—C(O)NH—.

11. The compound according to claim 1, wherein Y is a bond.

12. A pharmaceutical composition which comprises a compound of formula I according to claim 1 or a pharmaceutically acceptable salt thereof and one or more pharmaceutically acceptable excipients.

13. A method of inhibiting MK2 activity comprising contacting a cell with a compound of formula I according to claim 1, or a pharmaceutically acceptable salt thereof.

14. A compound according to claim 1 selected from the group consisting of:

2'-(2-(benzofuran-2-yl)pyrimidin-4-yl)-5',6'-dihydrospiro[piperidine-4,7'-pyrrolo[3,2-c]pyridin]-4'(1'H)-one;

2'-(2'-amino-2,5'-bipyrimidin-4-yl)-5',6'-dihydrospiro[piperidine-4,7'-pyrrolo[3,2-c]pyridin]-4'(1'H)-one;

2'-(2-(5-methoxypyridin-3-yl)pyrimidin-4-yl)-5',6'-dihydrospiro[piperidine-4,7'-pyrrolo[3,2-c]pyridin]-4'(1'H)-one;

2'-(2-(2-fluorophenyl)pyrimidin-4-yl)-5',6'-dihydrospiro[piperidine-4,7'-pyrrolo[3,2-c]pyridin]-4'(1'H)-one;

2'-(2-(3-fluorophenyl)pyrimidin-4-yl)-5',6'-dihydrospiro[piperidine-4,7'-pyrrolo[3,2-c]pyridin]-4'(1'H)-one;

2'-(2-(4-acetylphenyl)pyrimidin-4-yl)-5',6'-dihydrospiro[piperidine-4,7'-pyrrolo[3,2-c]pyridin]-4'(1'H)-one;

2'-(2-(benzo[d][1,3]dioxol-5-yl)pyrimidin-4-yl)-5',6'-dihydrospiro[piperidine-4,7'-pyrrolo[3,2-c]pyridin]-4'(1'H)-one;

N-(5-(4-(4'-oxo-1',4',5',6'-tetrahydrospiro[piperidine-4,7'-pyrrolo[3,2-c]pyridine]-2'-yl)pyrimidin-2-yl)pyridin-2-yl)acetamide;

N-(5-(4-(4'-oxo-1',4',5',6'-tetrahydrospiro[piperidine-4,7'-pyrrolo[3,2-c]pyridine]-2'-yl)pyrimidin-2-yl)pyridin-2-yl)propionamide;

2'-(2-(3-chloro-4-(trifluoromethyl)phenyl)pyrimidin-4-yl)-5',6'-dihydrospiro[piperidine-4,7'-pyrrolo[3,2-c]pyridin]-4'(1'H)-one;

2'-(2-(3,4-dihydro-2H-benzo[b][1,4]dioxepin-7-yl)pyrimidin-4-yl)-5',6'-dihydrospiro[piperidine-4,7'-pyrrolo[3,2-c]pyridin]-4'(1'H)-one;

2'-(2-(biphenyl-4-yl)pyrimidin-4-yl)-5',6'-dihydrospiro[piperidine-4,7'-pyrrolo[3,2-c]pyridin]-4'(1'H)-one;

2'-(2-(3,4-dichlorophenyl)pyrimidin-4-yl)-5',6'-dihydrospiro[piperidine-4,7'-pyrrolo[3,2-c]pyridin]-4'(1'H)-one;

2'-(2-(3-isopropylphenyl)pyrimidin-4-yl)-5',6'-dihydrospiro[piperidine-4,7'-pyrrolo[3,2-c]pyridin]-4'(1'H)-one;

2'-(2-(4-phenoxyphenyl)pyrimidin-4-yl)-5',6'-dihydrospiro[piperidine-4,7'-pyrrolo[3,2-c]pyridin]-4'(1'H)-one;

2'-(2-(3-(trifluoromethoxy)phenyl)pyrimidin-4-yl)-5',6'-dihydrospiro[piperidine-4,7'-pyrrolo[3,2-c]pyridin]-4'(1'H)-one;

2'-(2-(4-(trifluoromethyl)phenyl)pyrimidin-4-yl)-5',6'-dihydrospiro[piperidine-4,7'-pyrrolo[3,2-c]pyridin]-4'(1'H)-one;

2'-(2-(4-cyclohexylphenyl)pyrimidin-4-yl)-5',6'-dihydrospiro[piperidine-4,7'-pyrrolo[3,2-c]pyridin]-4'(1'H)-one;

2'-(2-(3-tert-butyl-5-methylphenyl)pyrimidin-4-yl)-5',6'-dihydrospiro[piperidine-4,7'-pyrrolo[3,2-c]pyridin]-4'(1'H)-one;

2'-(2-(4-hydroxy-3-methoxyphenyl)pyrimidin-4-yl)-5',6'-dihydrospiro[piperidine-4,7'-pyrrolo[3,2-c]pyridin]-4'(1'H)-one;

2'-(2-(quinolin-3-yl)pyrimidin-4-yl)-5',6'-dihydrospiro[piperidine-4,7'-pyrrolo[3,2-c]pyridin]-4'(1'H)-one;

2'-(2-(4-tert-butylphenyl)pyrimidin-4-yl)-5',6'-dihydrospiro[piperidine-4,7'-pyrrolo[3,2-c]pyridin]-4'(1'H)-one;

2'-(2-(4-isobutylphenyl)pyrimidin-4-yl)-5',6'-dihydrospiro[piperidine-4,7'-pyrrolo[3,2-c]pyridin]-4'(1'H)-one;

2'-(2-(naphthalen-2-yl)pyrimidin-4-yl)-5',6'-dihydrospiro[piperidine-4,7'-pyrrolo[3,2-c]pyridin]-4'(1'H)-one;

2'-(2-(3,5-dichlorophenyl)pyrimidin-4-yl)-5',6'-dihydrospiro[piperidine-4,7'-pyrrolo[3,2-c]pyridin]-4'(1'H)-one;

2'-(2-(dibenzo[b,d]furan-2-yl)pyrimidin-4-yl)-5',6'-dihydrospiro[piperidine-4,7'-pyrrolo[3,2-c]pyridin]-4'(1'H)-one;

2'-(2-(4-isobutoxyphenyl)pyrimidin-4-yl)-5',6'-dihydrospiro[piperidine-4,7'-pyrrolo[3,2-c]pyridin]-4'(1'H)-one;

2'-(2-(benzo[b]thiophen-2-yl)pyrimidin-4-yl)-5',6'-dihydrospiro[piperidine-4,7'-pyrrolo[3,2-c]pyridin]-4'(1'H)-one;

3-(4-(4'-oxo-1',4',5',6'-tetrahydrospiro[piperidine-4,7'-pyrrolo[3,2-c]pyridine]-2'-yl)pyrimidin-2-yl)benzamide;

2'-(2-(3-acetylphenyl)pyrimidin-4-yl)-5',6'-dihydrospiro[piperidine-4,7'-pyrrolo[3,2-c]pyridin]-4'(1'H)-one;

2-chloro-N-cyclohexyl-4-(4-(4'-oxo-1',4',5',6'-tetrahydrospiro[piperidine-4,7'-pyrrolo[3,2-c]pyridine]-2'-yl)pyrimidin-2-yl)benzamide;

2'-(2-(4-chloro-2-fluorophenyl)pyrimidin-4-yl)-5',6'-dihydrospiro[piperidine-4,7'-pyrrolo[3,2-c]pyridin]-4'(1'H)-one;

2'-(2-(biphenyl-3-yl)pyrimidin-4-yl)-5',6'-dihydrospiro[piperidine-4,7'-pyrrolo[3,2-c]pyridin]-4'(1'H)-one;

2'-(2-(3,5-bis(trifluoromethyl)phenyl)pyrimidin-4-yl)-5',6'-dihydrospiro[piperidine-4,7'-pyrrolo[3,2-c]pyridin]-4'(1'H)-one;

2'-(2-(3-(trifluoromethyl)phenyl)pyrimidin-4-yl)-5',6'-dihydrospiro[piperidine-4,7'-pyrrolo[3,2-c]pyridin]-4'(1'H)-one;

N-cyclohexyl-4-(4-(4'-oxo-1',4',5',6'-tetrahydrospiro[piperidine-4,7'-pyrrolo[3,2-c]pyridine]-2'-yl)pyrimidin-2-yl)benzamide;

2'-(2-(benzofuran-2-yl)pyrimidin-4-yl)-1-methyl-5',6'-dihydrospiro[piperidine-4,7'-pyrrolo[3,2-c]pyridin]-4'(1'H)-one;

2'-(2-(benzofuran-2-yl)pyrimidin-4-yl)-1-methyl-5',6'-dihydrospiro[piperidine-4,7'-pyrrolo[3,2-c]pyridin]-4'(1'H)-one;

2'-(2-(benzofuran-2-yl)pyrimidin-4-yl)-1-ethyl-5',6'-dihydrospiro[piperidine-4,7'-pyrrolo[3,2-c]pyridin]-4'(1'H)-one;

1-(2-aminoethyl)-2'-(2-(benzofuran-2-yl)pyrimidin-4-yl)-5',6'-dihydrospiro[piperidine-4,7'-pyrrolo[3,2-c]pyridin]-4'(1'H)-one;

N-(2-(2'-(2-(benzofuran-2-yl)pyrimidin-4-yl)-4'-oxo-1',4',5',6'-tetrahydrospiro[piperidine-4,7'-pyrrolo[3,2-c]pyridine]-1-yl)ethyl)acetamide;

N-(3-(2'-(2-(benzofuran-2-yl)pyrimidin-4-yl)-4'-oxo-1',4',5',6'-tetrahydrospiro[piperidine-4,7'-pyrrolo[3,2-c]pyridine]-1-yl)propyl)acetamide;

2'-(2-(benzofuran-2-yl)-5-fluoropyrimidin-4-yl)-5',6'-dihydrospiro[piperidine-4,7'-pyrrolo[3,2-c]pyridin]-4'(1'H)-one;

2'-(2-(benzo[d][1,3]dioxol-5-yl)-5-fluoropyrimidin-4-yl)-5',6'-dihydrospiro[piperidine-4,7'-pyrrolo[3,2-c]pyridin]-4'(1'H)-one;

2'-(5-fluoro-2-(quinolin-3-yl)pyrimidin-4-yl)-5',6'-dihydrospiro[piperidine-4,7'-pyrrolo[3,2-c]pyridin]-4'(1'H)-one;

4-(5-fluoro-4-(4'-oxo-1',4',5',6'-tetrahydrospiro[piperidine-4,7'-pyrrolo[3,2-c]pyridine]-2'-yl)pyrimidin-2-yl)-N-methylbenzamide;

2'-(2-(4-chloro-2-fluorophenyl)-5-fluoropyrimidin-4-yl)-5',6'-dihydrospiro[piperidine-4,7'-pyrrolo[3,2-c]pyridin]-4'(1'H)-one;

2'-(2-(benzofuran-2-yl)pyrimidin-4-yl)-5',6'-dihydrospiro[piperidine-3,7'-pyrrolo[3,2-c]pyridin]-4'(1'H)-one;

2'-(2-(benzo[d][1,3]dioxol-5-yl)pyrimidin-4-yl)-5',6'-dihydrospiro[piperidine-3,7'-pyrrolo[3,2-c]pyridin]-4'(1'H)-one;

2'-(2-(benzo[d][1,3]dioxol-5-yl)pyrimidin-4-yl)-5',6'-dihydrospiro[pyrrolidine-3,7'-pyrrolo[3,2-c]pyridin]-4'(1'H)-one;

2'-(2-p-tolylpyrimidin-4-yl)-5',6'-dihydrospiro[pyrrolidine-3,7'-pyrrolo[3,2-c]pyridin]-4'(1'H)-one;

2'-(2-(3-fluorophenyl)pyrimidin-4-yl)-5',6'-dihydrospiro[pyrrolidine-3,7'-pyrrolo[3,2-c]pyridin]-4'(1'H)-one;

2'-(2-(benzofuran-2-yl)pyrimidin-4-yl)-5',6'-dihydrospiro[pyrrolidine-3,7'-pyrrolo[3,2-c]pyridin]-4'(1'H)-one;

2'-(2-(benzofuran-2-yl)pyrimidin-4-yl)-5',6'-dihydrospiro[morpholine-2,7'-pyrrolo[3,2-c]pyridin]-4'(1'H)-one;

2'-(2-(benzofuran-2-yl)pyrimidin-4-yl)-5',6'-dihydrospiro[piperidine-4,7'-pyrrolo[3,2-c]pyridin]-4'(1'H)-one;

2'-(2-(quinolin-3-yl)pyridin-4-yl)-5',6'-dihydrospiro[piperidine-4,7'-pyrrolo[3,2-c]pyridin]-4'(1'H)-one;

2'-(2-(benzo[d][1,3]dioxol-5-yl)pyridin-4-yl)-5',6'-dihydrospiro[piperidine-4,7'-pyrrolo[3,2-c]pyridin]-4'(1'H)-one;

2'-(2-(benzo[d]thiazol-2-yl)pyridin-4-yl)-5',6'-dihydrospiro[piperidine-4,7'-pyrrolo[3,2-c]pyridin]-4'(1'H)-one;

2'-(2-(benzo[d]thiazol-2-yl)pyrimidin-4-yl)-5',6'-dihydrospiro[piperidine-4,7'-pyrrolo[3,2-c]pyridin]-4'(1'H)-one;

2'-(2-(thiazol-2-yl)pyrimidin-4-yl)-5',6'-dihydrospiro[piperidine-4,7'-pyrrolo[3,2-c]pyridin]-4'(1'H)-one;

1-(2-aminoacetyl)-2'-(2-(benzofuran-2-yl)pyrimidin-4-yl)-5',6'-dihydrospiro[piperidine-4,7'-pyrrolo[3,2-c]pyridin]-4'(1'H)-one;

2'-(2'-(cyclopentylamino)-2,5'-bipyrimidin-4-yl)-5',6'-dihydrospiro[piperidine-4,7'-pyrrolo[3,2-c]pyridin]-4'(1'H)-one;

N-(4-(4'-oxo-1',4',5',6'-tetrahydrospiro[piperidine-4,7'-pyrrolo[3,2-c]pyridine]-2'-yl)pyridin-2-yl)-4-(trifluoromethyl)benzamide;

3,4-dimethyl-N-(4-(4'-oxo-1',4',5',6'-tetrahydrospiro[piperidine-4,7'-pyrrolo[3,2-c]pyridine]-2'-yl)pyridin-2-yl)benzamide;

N-(4-(4'-oxo-1',4',5',6'-tetrahydrospiro[piperidine-3,7'-pyrrolo[3,2-c]pyridine]-2'-yl)pyrimidin-2-yl)-4-(trifluoromethyl)benzamide;

N-(4-(4'-oxo-1',4',5',6'-tetrahydrospiro[piperidine-3,7'-pyrrolo[3,2-c]pyridine]-2'-yl)pyrimidin-2-yl)-3-(trifluoromethoxy)benzamide; 2'-(2-(6-aminopyridin-3-yl)pyrimidin-4-yl)-5',6'-dihydrospiro[piperidine-4,7'-pyrrolo[3,2-c]pyridin]-4'(1'H)-one;

2'-(2-(pyridin-3-yl)pyrimidin-4-yl)-5',6'-dihydrospiro[piperidine-4,7'-pyrrolo[3,2-c]pyridin]-4'(1'H)-one;

2'-(2-(pyridin-3-yl)pyrimidin-4-yl)-5',6'-dihydrospiro[piperidine-3,7'-pyrrolo[3,2-c]pyridin]-4'(1'H)-one;

(S)-2'-(2-(pyridin-3-yl)pyrimidin-4-yl)-5',6'-dihydrospiro[piperidine-3,7'-pyrrolo[3,2-c]pyridin]-4'(1'H)-one;

(R)-2'-(2-(pyridin-3-yl)pyrimidin-4-yl)-5',6'-dihydrospiro[piperidine-3,7'-pyrrolo[3,2-c]pyridin]-4'(1'H)-one;

2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;

(S)-2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;

(R)-2'-(2-(6-(3-methoxypropoxy)pyridin-3-yl)pyrimidin-4-yl)-5',6'-dihydrospiro[piperidine-3,7'-pyrrolo[3,2-c]pyridin]-4'(1'H)-one;

2'-(2-(5-methoxypyridin-3-yl)pyrimidin-4-yl)-5',6'-dihydrospiro[piperidine-3,7'-pyrrolo[3,2-c]pyridin]-4'(1'H)-one;

(S)-2'-(2-(5-methoxypyridin-3-yl)pyrimidin-4-yl)-5',6'-dihydrospiro[piperidine-3,7'-pyrrolo[3,2-c]pyridin]-4'(1'H)-one;

(R)-2'-(2-(5-methoxypyridin-3-yl)pyrimidin-4-yl)-5',6'-dihydrospiro[piperidine-3,7'-pyrrolo[3,2-c]pyridin]-4'(1'H)-one;

2'-(2'-(cyclopentylamino)-2,5'-bipyrimidin-4-yl)-5',6'-dihydrospiro[piperidine-4,7'-pyrrolo[3,2-c]pyridin]-4'(1'H)-one;

3,4-dimethyl-N-(4-(4'-oxo-1',4',5',6'-tetrahydrospiro[piperidine-4,7'-pyrrolo[3,2-c]pyridine]-2'-yl)pyrimidin-2-yl)benzamide;

3,4-dimethyl-N-(4-(4'-oxo-1',4',5',6'-tetrahydrospiro[piperidine-4,7'-pyrrolo[3,2-c]pyridine]-2'-yl)pyrimidin-2-yl)benzamide;

3-fluoro-N-(4-(4'-oxo-1',4',5',6'-tetrahydrospiro[piperidine-4,7'-pyrrolo[3,2-c]pyridine]-2'-yl)pyridin-2-yl)benzamide;

3-fluoro-N-(4-(4'-oxo-1',4',5',6'-tetrahydrospiro[piperidine-4,7'-pyrrolo[3,2-c]pyridine]-2'-yl)pyridin-2-yl)benzamide;

N-(4-(4'-oxo-1',4',5',6'-tetrahydrospiro[piperidine-4,7'-pyrrolo[3,2-c]pyridine]-2'-yl)pyridin-2-yl)picolinamide;

4-fluoro-N-(4-(4'-oxo-1',4',5',6'-tetrahydrospiro[piperidine-4,7'-pyrrolo[3,2-c]pyridine]-2'-yl)pyrimidin-2-yl)benzamide;

4-fluoro-N-(4-(4'-oxo-1',4',5',6'-tetrahydrospiro[piperidine-4,7'-pyrrolo[3,2-c]pyridine]-2'-yl)pyrimidin-2-yl)benzamide;

N-(4-(4'-oxo-1',4',5',6'-tetrahydrospiro[piperidine-4,7'-pyrrolo[3,2-c]pyridine]-2'-yl)pyrimidin-2-yl)-2-naphthamide;

N-(4-(4'-oxo-1',4',5',6'-tetrahydrospiro[piperidine-4,7'-pyrrolo[3,2-c]pyridine]-2'-yl)pyridin-2-yl)-2-naphthamide;

N-(4-(4'-oxo-1',4',5',6'-tetrahydrospiro[piperidine-4,7'-pyrrolo[3,2-c]pyridine]-2'-yl)pyrimidin-2-yl)-1-naphthamide;

N-(4-(4'-oxo-1',4',5',6'-tetrahydrospiro[piperidine-4,7'-pyrrolo[3,2-c]pyridine]-2'-yl)pyridin-2-yl)-1-naphthamide;

N-(4-(4'-oxo-1',4',5',6'-tetrahydrospiro[piperidine-4,7'-pyrrolo[3,2-c]pyridine]-2'-yl)pyridin-2-yl)biphenyl-4-carboxamide;

N-(4-(4'-oxo-1',4',5',6'-tetrahydrospiro[piperidine-4,7'-pyrrolo[3,2-c]pyridine]-2'-yl)pyridin-2-yl)-4-(trifluoromethyl)benzamide;

3-(dimethylamino)-N-(4-(4'-oxo-1',4',5',6'-tetrahydrospiro[piperidine-4,7'-pyrrolo[3,2-c]pyridine]-2'-yl)pyridin-2-yl)benzamide;

N-(4-(4'-oxo-1',4',5',6'-tetrahydrospiro[piperidine-4,7'-pyrrolo[3,2-c]pyridine]-2'-yl)pyridin-2-yl)isonicotinamide;
6-methoxy-N-(4-(4'-oxo-1',4',5',6'-tetrahydrospiro[piperidine-4,7'-pyrrolo[3,2-c]pyridine]-2'-yl)pyridin-2-yl)picolinamide;
3,4-dimethyl-N-(4-(1-methyl-4'-oxo-1',4',5',6'-tetrahydrospiro[piperidine-4,7'-pyrrolo[3,2-c]pyridine]-2'-yl)pyridin-2-yl)benzamide;
3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
(S)-3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
(R)-3,4-dimethyl-N-(4-(4'-oxo-1',4',5',6'-tetrahydrospiro[piperidine-3,7'-pyrrolo[3,2-c]pyridine]-2'-yl)pyridin-2-yl)benzamide;
3,4-dimethyl-N-(4-(4'-oxo-1',4',5',6'-tetrahydrospiro[pyrrolidine-3,7'-pyrrolo[3,2-c]pyridine]-2'-yl)pyridin-2-yl)benzamide;
N-(4-(1-methyl-4'-oxo-1',4',5',6'-tetrahydrospiro[piperidine-4,7'-pyrrolo[3,2-c]pyridine]-2'-yl)pyridin-2-yl)-3-(trifluoromethoxy)benzamide;
N-(4-(4'-oxo-1',4',5',6'-tetrahydrospiro[piperidine-3,7'-pyrrolo[3,2-c]pyridine]-2'-yl)pyridin-2-yl)-3-(trifluoromethoxy)benzamide;
N-(4-(4'-oxo-1',4',5',6'-tetrahydrospiro[pyrrolidine-3,7'-pyrrolo[3,2-c]pyridine]-2'-yl)pyridin-2-yl)-3-(trifluoromethoxy)benzamide;
3-fluoro-N-(4-(1-methyl-4'-oxo-1',4',5',6'-tetrahydrospiro[piperidine-4,7'-pyrrolo[3,2-c]pyridine]-2'-yl)pyridin-2-yl)benzamide;
3-fluoro-N-(4-(4'-oxo-1',4',5',6'-tetrahydrospiro[piperidine-3,7'-pyrrolo[3,2-c]pyridine]-2'-yl)pyridin-2-yl)benzamide;
3-fluoro-N-(4-(4'-oxo-1',4',5',6'-tetrahydrospiro[pyrrolidine-3,7'-pyrrolo[3,2-c]pyridine]-2'-yl)pyridin-2-yl)benzamide;
N-(4-(4'-oxo-1',4',5',6'-tetrahydrospiro[piperidine-3,7'-pyrrolo[3,2-c]pyridine]-2'-yl)pyridin-2-yl)picolinamide;
N-(4-(4'-oxo-1',4',5',6'-tetrahydrospiro[pyrrolidine-3,7'-pyrrolo[3,2-c]pyridine]-2'-yl)pyridin-2-yl)picolinamide;
4-fluoro-N-(4-(4'-oxo-1',4',5',6'-tetrahydrospiro[piperidine-3,7'-pyrrolo[3,2-c]pyridine]-2'-yl)pyridin-2-yl)benzamide;
(S)-4-fluoro-N-(4-(4'-oxo-1',4',5',6'-tetrahydrospiro[piperidine-3,7'-pyrrolo[3,2-c]pyridine]-2'-yl)pyridin-2-yl)benzamide;
(R)-4-fluoro-N-(4-(4'-oxo-1',4',5',6'-tetrahydrospiro[piperidine-3,7'-pyrrolo[3,2-c]pyridine]-2'-yl)pyridin-2-yl)benzamide;
4-fluoro-N-(4-(4'-oxo-1',4',5',6'-tetrahydrospiro[pyrrolidine-3,7'-pyrrolo[3,2-c]pyridine]-2'-yl)pyridin-2-yl)benzamide;
N-(4-(1-methyl-4'-oxo-1',4',5',6'-tetrahydrospiro[piperidine-4,7'-pyrrolo[3,2-c]pyridine]-2'-yl)pyridin-2-yl)-2-naphthamide;
N-(4-(4'-oxo-1',4',5',6'-tetrahydrospiro[piperidine-3,7'-pyrrolo[3,2-c]pyridine]-2'-yl)pyridin-2-yl)-2-naphthamide;
(S)—N-(4-(4'-oxo-1',4',5',6'-tetrahydrospiro[piperidine-3,7'-pyrrolo[3,2-c]pyridine]-2'-yl)pyridin-2-yl)-2-naphthamide;
N-(4-(4'-oxo-1',4',5',6'-tetrahydrospiro[pyrrolidine-3,7'-pyrrolo[3,2-c]pyridine]-2'-yl)pyridin-2-yl)-2-naphthamide;
N-(4-(4'-oxo-1',4',5',6'-tetrahydrospiro[piperidine-3,7'-pyrrolo[3,2-c]pyridine]-2'-yl)pyridin-2-yl)-3-(trifluoromethyl)benzamide;
3,5-difluoro-N-(4-(4'-oxo-1',4',5',6'-tetrahydrospiro[piperidine-3,7'-pyrrolo[3,2-c]pyridine]-2'-yl)pyridin-2-yl)benzamide;
N-(4-(4'-oxo-1',4',5',6'-tetrahydrospiro[piperidine-3,7'-pyrrolo[3,2-c]pyridine]-2'-yl)pyridin-2-yl)-1-naphthamide;
N-(4-(4'-oxo-1',4',5',6'-tetrahydrospiro[piperidine-3,7'-pyrrolo[3,2-c]pyridine]-2'-yl)pyridin-2-yl)quinoline-2-carboxamide;
N-(4-(4'-oxo-1',4',5',6'-tetrahydrospiro[piperidine-3,7'-pyrrolo[3,2-c]pyridine]-2'-yl)pyridin-2-yl)isoquinoline-1-carboxamide; and
N-(4-(4'-oxo-1',4',5',6'-tetrahydrospiro[piperidine-3,7'-pyrrolo[3,2-c]pyridine]-2'-yl)pyridin-2-yl)-4-(trifluoromethyl)benzamide, and
(S)-2'-(2-(benzo[d][1,3]dioxol-5-yl)pyrimidin-4-yl)-5',6'-dihydrospiro[piperidine-3,7'-pyrrolo[3,2-c]pyridin]-4'(1'H)-one,
or a pharmaceutically acceptable salt thereof.

15. A method of treating a disease selected from the group consisting of prostate cancer, skin cancer, bladder cancer, multiple myeloma, and metatstatic melanoma, in a subject in need thereof, comprising administering to the subject a therapeutically effective amount of a compound of formula I according to claim 1 or a pharmaceutically acceptable salt thereof, so as to thereby treat the subject.

16. A method of treating a disease selected from the group consisting of rheumatoid arthritis, psoriasis and inflammatory bowel disease, in a subject in need thereof, comprising administering to the subject a therapeutically effective amount of a compound of formula I according to claim 1 or a pharmaceutically acceptable salt thereof, so as to thereby treat the subject.

* * * * *